(12) United States Patent
Juge et al.

(10) Patent No.: US 9,707,553 B2
(45) Date of Patent: Jul. 18, 2017

(54) P-CHIROGENIC ORGANOPHOSPHORUS COMPOUNDS

(71) Applicants: CENTRE NATIONAL DE LA RECHERCHE SCIENTIFIQUE (CNRS), Paris (FR); UNIVERSITE DE BOURGOGNE, Dijon (FR); UNIVERSITE DE STRASBOURG, Strasbourg (FR); SYNTHELOR SAS, Vandoeuvre-les-Nancy (FR)

(72) Inventors: Sylvain Juge, Dijon (FR); Jerome Bayardon, Dijon (FR); Emmanuelle Remond, Mailleroncourt-Charette (FR); Hugo Laureano, Dijon (FR); Jean-Christophe Henry, Nancy (FR); Frederic Leroux, Herrlisheim (FR); Francoise Colobert, Lampertheim (FR)

(73) Assignees: CENTRE NATIONAL DE LA RECHERCHE SCIENTIFIQUE (CNRS), Paris (FR); UNIVERSITE DE BOURGOGNE, Dijon (FR); UNIVERSITE DE STRASBOURG, Strasbourg (FR); SYNTHELOR SAS, Vandoeuvre-les-Nancy (FR)

( * ) Notice: Subject to any disclaimer, the term of this patent is extended or adjusted under 35 U.S.C. 154(b) by 0 days.

(21) Appl. No.: 14/876,072

(22) Filed: Oct. 6, 2015

(65) Prior Publication Data
US 2016/0023199 A1    Jan. 28, 2016

Related U.S. Application Data

(63) Continuation of application No. 14/232,435, filed as application No. PCT/EP2012/063489 on Jul. 10, 2012.
(Continued)

(30) Foreign Application Priority Data

Jul. 22, 2011    (FR) ..................... 11 56686

(51) Int. Cl.
*C07F 9/50* (2006.01)
*C07B 37/04* (2006.01)
(Continued)

(52) U.S. Cl.
CPC ....... *B01J 31/2409* (2013.01); *B01J 31/2286* (2013.01); *B01J 31/2295* (2013.01);
(Continued)

(58) Field of Classification Search
CPC ........ C07F 9/5045; C07F 9/5022; C07F 9/54; C07F 9/6596; B01J 2231/46; B01J 31/2404; C07B 37/04; C07B 53/00
See application file for complete search history.

(56) References Cited

U.S. PATENT DOCUMENTS 2,922,819 A    1/1960    Chatt et al.

OTHER PUBLICATIONS

Longeau et al. (Tetrahedron Letters, vol. 37, No. 13, p. 2209-2212; (1996)).*

(Continued)

*Primary Examiner* — Valerie Rodriguez-Garcia
(74) *Attorney, Agent, or Firm* — Young & Thompson

(57) ABSTRACT

P-chirogenic organophosphorus compounds of general formula (I), a process for the synthesis of the compounds of formula (I), and intermediate products of general formulae (II), (III) and (IV), as shown below, are involved in the synthesis of compounds (I).

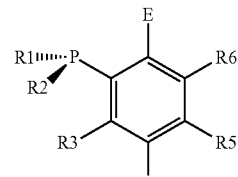

(I)

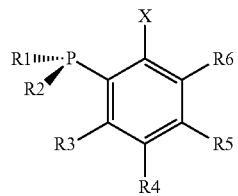

(II)

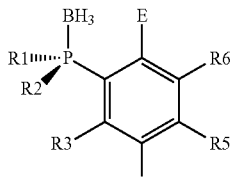

(III)

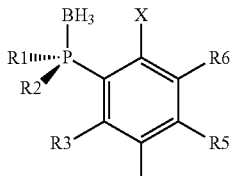

(IV)

Metal complexes comprising compounds (I) as ligands are also described. The compounds and complexes are useful in asymmetric catalysis by transition metal complexes or organocatalysis, especially for asymmetric hydrogenation or allylation. Compounds of general formula (I) may be useful (Continued)

as agrochemical and therapeutic substances, or as reagents or intermediates for fine chemistry.

4 Claims, No Drawings

Related U.S. Application Data

(60) Provisional application No. 61/506,291, filed on Jul. 11, 2011.

(51) Int. Cl.

| | | |
|---|---|---|
| *C07B 53/00* | (2006.01) | |
| *C07F 9/54* | (2006.01) | |
| *B01J 31/24* | (2006.01) | |
| *C07F 15/00* | (2006.01) | |
| *C07F 17/02* | (2006.01) | |
| *B01J 31/22* | (2006.01) | |
| *C07F 9/6596* | (2006.01) | |
| *C07F 17/00* | (2006.01) | |

(52) U.S. Cl.
CPC .............. *C07B 37/04* (2013.01); *C07B 53/00* (2013.01); *C07F 9/50* (2013.01); *C07F 9/5022* (2013.01); *C07F 9/5027* (2013.01); *C07F 9/5045* (2013.01); *C07F 9/5054* (2013.01); *C07F 9/5072* (2013.01); *C07F 9/54* (2013.01); *C07F 9/6596* (2013.01); *C07F 15/00* (2013.01); *C07F 15/0073* (2013.01); *C07F 17/00* (2013.01); *C07F 17/02* (2013.01); *B01J 2231/44* (2013.01); *B01J 2231/645* (2013.01); *B01J 2531/822* (2013.01); *B01J 2531/824* (2013.01)

(56) References Cited

OTHER PUBLICATIONS

Baudin et al. (J. Org. Chem. 2003, 68, 4293-4301).*
Imamoto et al. (Angew. chem. Int. Ed. 2007, 46, 8636-8639).*
Ken Tamura et al., "Enantiopure 1,2-Bis(tert-butylmethylphosphino)benzene as a Highly Efficient Ligand in Rhodium-Catalyzed Asymmetric Hydrogenation", Organic Letters, Oct. 1, 2010, pp. 4400-4403, vol. 12, No. 19.
Tsuneo Imamoto et al., "Rigid P-Chiral Phosphine Ligands with tert-Butylmethylphosphino Groups for Rhodium-Catalyzed Asymmetric Hydrogenation of Functionalized Alkenes", Journal of the American Chemical Society, Jan. 25, 2012, pp. 1754-1769, vol. 134, No. 3.
Alexia Longeau, et al.; "Preparation and Reactions of Functionalized Chlorodiorganophosphine-Borane Complexes Using Organozinc Reagents"; (Tetrahedron Letters, vol. 37, No. 13, p. 2209-2212; (1996).
Christophe Baudin et al.; "Highly Enantiomerically Enriched Chlorophosphine Boranes: Synthesis and Applications as P-Chirogenic Electrophilic Blocks"; (J. Org. Chem. 2003, 68, 4293-4301).
Tsuneo Imamoto et al.; "Synthesis and Enantioselectivity of P-Chiral Phosphine Ligands with Alkynyl Groups"; (Angew. Chem. Int. Ed. 2007, 46, 8636-8639).
Jerry March; "Advanced Organic Chemistry"; Reactions, Mechanisms, and Structure; 1985; Third Edition; Chapter 19; p. 1049.

* cited by examiner

P-CHIROGENIC ORGANOPHOSPHORUS COMPOUNDS

FIELD OF INVENTION

The present invention relates to novel P-chirogenic organophosphorus compounds of general formula (I). The present invention also provides a process for the synthesis of said compounds of formula (I). The present invention also relates to intermediate products of general formulae (II), (III) and (IV), as shown below, which are involved in the synthesis of compounds (I).

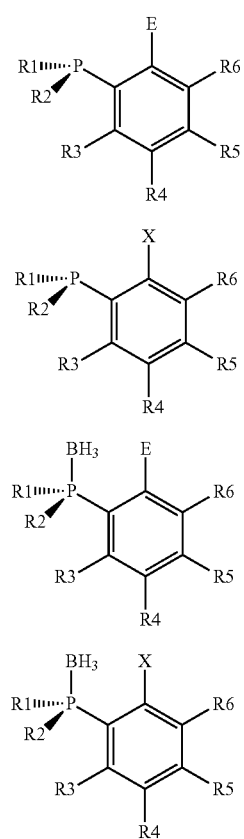

Compounds of general formula (I) may useful as agrochemical and therapeutic substances, or as reagents or intermediates for fine chemistry.

Further, the invention relates to metal complexes comprising compounds (I) as ligands. The novel compounds and complexes of the present invention are useful in asymmetric catalysis by transition metal complexes or organocatalysis, especially for asymmetric hydrogenation or allylation.

BACKGROUND OF INVENTION

During the past decades, asymmetric organocatalysis and organometallic catalysis made a breakthrough and became methodologies of choice for the synthesis of chiral substances on laboratory as well as on industrial scale. Numerous chiral catalysts are formed by complexation of a phosphorus ligand with a transition metal. Sometimes, organophosphorus compounds may also be directly used as organocatalysts. In this latter case, organophosphorus derivatives may be used as counter ions, as organocatalysts in asymmetric reactions under phase transfer conditions or as Lewis bases.

As no "universal" ligand exists for asymmetric catalysis, the synthesis and the study of new chiral ligands remains a field in permanent development.

In most cases, the organophosphorus compounds used in asymmetric reactions derive from naturally occurring substances or easily accessible precursors (for example binaphthol, tartaric acid, amino-acids, carbohydrates . . . ) in which the chirality is on the carbon skeleton. In organophosphorus organometallic catalysts, chirality of the carbon skeleton is transferred to the coordination sphere of the metal through the phosphorus substituents. The most popular chiral organophosphorus compounds used in asymmetric reactions, such as Quinap, Binap, XyliPhos or DuPhos, have axial- or planar-chirality or still chirality due to a cycle.

Organophosphorus compounds bearing the chirality on the phosphorus centers (P-chirogenic), such as Dipamp or MiniPhos, are very interesting from an industrial and stereochemical point of view in organometallic catalysis. In fact, they allow introducing directly a sterically and electronically well-defined architecture around the metal center, depending on the nature of the substituents present on the phosphorus atom. The resulting chiral environment is more efficient than the one obtained by the transfer of chirality from the carbon skeleton.

P-chirogenic organophosphorus compounds are also interesting as organocatalysts. They may be used as phosphonium salts, acido-basic derivatives or conduce to obtain low valence chiral complexes.

However, P-chirogenic organophosphorus compounds are not often used in asymmetric catalysis due to difficulties of synthesis and to delicate procedures of resolution of optically active compounds.

The asymmetric synthesis of organophosphorus ligands has made significant progresses in the last decade due to the introduction of borane as protecting group of the phosphorus atom. Organophosphorus borane complexes are stable, often crystalline compounds, which give clean reactions either on the P-center or on the alpha or beta position of the phosphorus substituents. The borane decomplexation can easily be achieved to give quantitatively the corresponding P(III)-compound with complete retention of configuration on the phosphorus center (Uziel J., Darcel C, Moulin D., Bauduin C and Jugé S., Tetrahedron: Asymmetry, 2001, 12, 1441-1449).

Today, the enantioselective synthesis of P-chirogenic organophosphorus compounds is essentially achieved by two approaches using phosphine boranes acting either as electrophilic or as a nucleophilic reagents.

In the electrophilic approach, phosphinite borane 1 or chlorophosphine borane (VII) may be prepared using a methodology starting from ephedrine (Jugé S., Stephan M., Laffitte J. A. and Gênet J. P., Tetrahedron Lett., 1990, 31, 6357-6360; Bauduin C, Moulin D., Kaloun E. B., Darcel C and Jugé S., J. Org. Chem., 2003, 68, 4293-4301). These electrophilic reagents may then be used to prepare ferrocenyl- and silyl-bridged diphosphines.

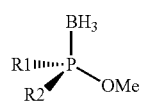

1

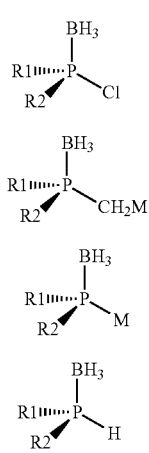

In the nucleophilic approach, carbanions in alpha-position of phosphine boranes 3 can be obtained either by deprotonation of a methylphosphine borane or via a dynamic kinetic resolution of a dimethylphosphine borane in presence of sparteine (Muci A. R., Campos K. R. and Evans D. A., J. Am. Chem. Soc., 1995, 117, 9075-9076; Yamada Y. and Imamoto T., J. Org. Chem., 1999, 64, 2988-2989). The reaction of these carbanions with various electrophiles leads to ethano- or methano-bridged diphosphines.

Another nucleophilic approach uses a dynamic kinetic resolution of racemic secondary phosphine boranes in presence of sparteine. The phosphide lithium borane 4 (M=Li) obtained under these conditions may be used for the synthesis of pincer ligands via the formation of two P—C bonds. The metallophosphide boranes 4 are highly important building-blocks for the synthesis of novel classes of P-chirogenic ligands. However, the preparation of these compounds with high stereoselectivities was restricted until recently to lithiated examples with sterically hindered substituents like t-butyl or adamantly groups (Crépy K. V. L., Imamoto T., Top. Curr. Chem., 2003, 229, 1-40; Imamoto T., J. Synth. Org. Chem., Jpn., 2007, 65, 1060-1069).

Therefore, there remains a need for the development of new methods of synthesis of optically active phosphine ligands. Such methods should be versatile enough to easily lead to broad libraries of optically active phosphine ligands that may be tested for asymmetric synthesis applications.

Recently, the Applicant has developed a new methodology for the preparation of P-chirogenic secondary phosphine boranes (V) starting from chlorophosphine boranes (VII).

This unprecedented methodology is based on halogen/metal exchange reactions at low temperature which proceed with complete retention of configuration on the P-atom (scheme 1). The subsequent protonation of the intermediate phosphide boranes 4 affords secondary phosphine boranes of general formula (V) with excellent enantiomeric excess (ee>90%).

Scheme 1.

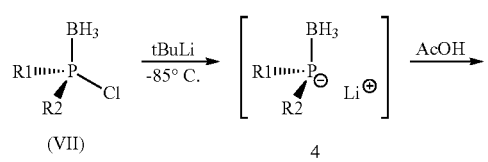

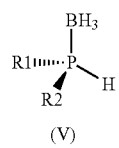

As a result of intensive research conducted for the development of new optically active phosphine compounds, the Applicant found that new classes of ligands or organocatalysts of general formula (1) may be obtained with very high enantiomeric excess starting from chlorophosphine boranes (VII) (scheme 2). The synthetic approach leading to compounds (I) was found to be very versatile, giving access to a wide variety of products and easy modification of their substituents.

Scheme 2.

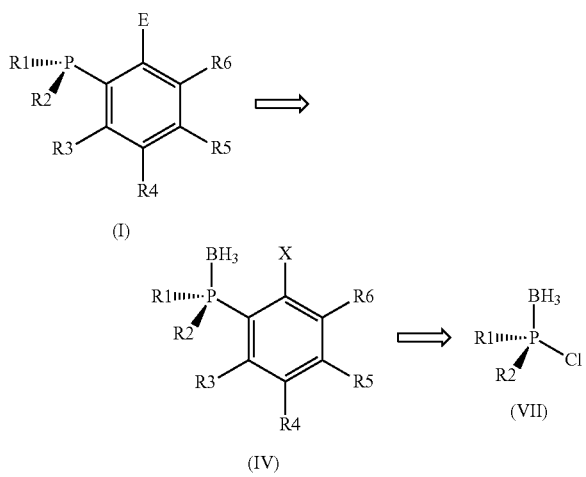

The process developed by the Applicant for producing compounds (I) involves the synthesis of intermediate phosphine boranes of general formula (IV) bearing an activated group in the ortho position (scheme 2).

The process of the invention especially enables the synthesis of enantioenriched ortho-functionalized phosphines, such as for example o-boronate, o-silano phosphines and o-hydroxymethyl.

O-boronates phosphines are ambiphiles, i.e. bearing both Lewis acid and base, and are of particular interest in the fields of synthesis and catalysis for their use as ligand. To the Applicants-s knowledge, no chiral borane or boranate phosphine has been described so far.

Chiral enantiopure o-hydroxymethyl phosphines are also particularly interesting as they can be used both as asymmetric organocatalyst and as ligand in organometallic catalysis. For example, Nakamura reported the use of non-P-chirogenic phosphines bearing a hydroxymethylated chelating chain for Ni-catalyzed coupling reactions (Yoshikai N., Matsuda H. and Nakamura E., J. Am. Chem. Soc. 2009, 131, 9590-9599).

The only example of preparation of P-chirogenic phosphines bearing a hydroxymethylated chelating chain has been reported by Beak et al. (Tollefson M., Li J. and Beak P., J. Am Chem. Soc., 1996, 118, 9052-9061). It involves phosphinite rearrangement and the methods of synthesis is not versatile.

o-hydroxymethyl phosphines may also be used as precursors of o-hydroxymethyl phosphonium salts, which are known to be synthetically useful in Wittig reactions (Marcoux D. and Charette A., Adv. Synth. Catal. 2008, 350, 2967-2974; McNulty J. and Keskar K., Tetrahedron Letters, 2008, 49, 7054-7057). It may also be envisaged to use o-hydroxymethyl phosphonium salts as new interesting organocatalysts.

Applications in asymmetric catalysis of P-chirogenic organophosphorus compounds (I) as ligands have been explored. Especially, compounds (I) may be used as ligands of transition metal, such as rhodium or palladium, and the resulting complexes may be suitable for asymmetric catalyzed hydrogenation, allylation, hydroformylation or carbonylation reactions. Phosphonium salts of compounds (I) may also be used in asymmetric reactions using phase transfer conditions such as fluoration or cyanation.

DEFINITIONS

In the present invention, the following terms have the following meanings:

"P-chirogenic" refers to phosphorus compounds leading to a stereoisomer of the original molecule by interchanging two substituents of the phosphorus center;

"organophosphorus": refers to organic compoundscontaining carbon-phosphorus bonds;

"organocatalysis", refers to a form of catalysis, whereby the rate of a chemical reaction is increased by an organic catalyst referred to as an "organocatalyst" consisting of carbon, hydrogen, sulfur and other non-metal elements found in organic compounds;

"catalysis by transition metal complexes", refers to a form of catalysis, whereby the rate of a chemical reaction is increased by organometallic compounds, i.e. by chemical compounds containing metal-element bounds of a largely covalent character;

"electrophilic coupling" refers to a bond formation, such as P—C, thanks to an electrophilic reagent, such as aryne;

"electrophilic reagent" refers to a reactant which accepts an electron pair from a molecule, with which it forms a covalent bound;

"oxidative coupling" refers to a bond formation thanks to an oxidative process;

"oxidative reagent" refers to a reactant that gains electrons in a redox chemical reaction;

"alkyl", refers to any saturated linear or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl;

"cycloalkyl", refers to a substituted or not substituted cyclic alkyl substituent such as cyclopropyl, cyclopentyl, or cyclohexyl;

"aryl", refers to a mono- or polycyclic system of 5 to 20, and preferably 6 to 12, carbon atoms having one or more aromatic rings (when there are two rings, it is called a biaryl) among which it is possible to cite the phenyl group, the biphenyl group, the 1-naphthyl group, the 2-naphthyl group, the tetrahydronaphthyl group, the indanyl group and the binaphthyl group. The term aryl also means any aromatic ring including at least one heteroatom chosen from an oxygen, nitrogen or sulfur atom. The aryl group can be substituted by 1 to 3 substituents chosen independently of one another, among a hydroxyl group, a linear or branched alkyl group comprising 1, 2, 3, 4, 5 or 6 carbon atoms, in particular methyl, ethyl, propyl, butyl, an alkoxy group or a halogen atom, in particular bromine, chlorine and iodine;

"alcoxy", refers to any O-alkyl or O-aryl group;

"alkyloxy", refers to any O-alkyl group;

"cycloalkyloxy", refers to any O-cycloalkyl group;

"aryloxy", refers to any O-aryl group;

"alkylamino", refers to any N-alkyl group;

"cycloalkylamino", refers to any N-cycloalkyl group;

"arylamino", refers to any N-aryl group;

"acyl chloride" refers to an organic compound with the general formula RCOCl, where R represent a substituted or unsubstituted group selected from alkyl or aryl group;

"aldehyde" refers to an organic compound containing a formyl group with the structure R—CHO, wherein R represent a substituted or unsubstituted group selected from alkyl or aryl group;

"ketone" refers to an organic compound with the structure $RC(=O)R'$, wherein R and R' may be the same or different and represent each a substituted or unsubstituted group selected from alkyl or aryl group;

"halosilane" refers to any halogen substituted silane;

"haloalkane" refers to a chemical compounds derived from an alkane and containing one or more halogens;

"halophosphine" refers to any halogen substituted phosphine;

"metallocenyl" refers to a group comprising a metal sandwiched between two cyclopentadienyl groups or a group comprising a metal bounded to the π-cloud of a cyclopentadienyl or similar substituent;

"boronate reagent" refers to reagents derived from boron, especially borane, borane complexes, boronate esters or haloboranes;

"phosphine borane", refers to a complex between a phosphine and the borane ($BH_3$);

"ortho position" refers, in the present invention, to the position on the aromatic ring that is adjacent to the position of the phosphorus atom;

"transition metal salt" refers to salt of transition-metal ions such as iron, copper, palladium or rhodium associated with chloride, sulfate, nitrate, acetocetonate, tetrafluoroborate, hexafluorophosphate, hexafluoroantimonate, triflate counter anions;

"transition metal complex" refers to a specie consisting of a transition metal coordinated (bonded to) one or more ligands (neutral or anionic non-metal species);

"o-An" represent a o-anisyl group, "o-Tol" represent a o-tolyl group, "cHex" represent a cyclohexyl group, "Fc" represent a ferrocenyl group, "Ph" represent a phenyl group and "i-Pr" represent a iso-propyl group.

SUMMARY

The present invention relates to a selective process of synthesis of P-chirogenic organophosphorus compound of general formula (I), summarized in scheme 3.

Scheme 3.

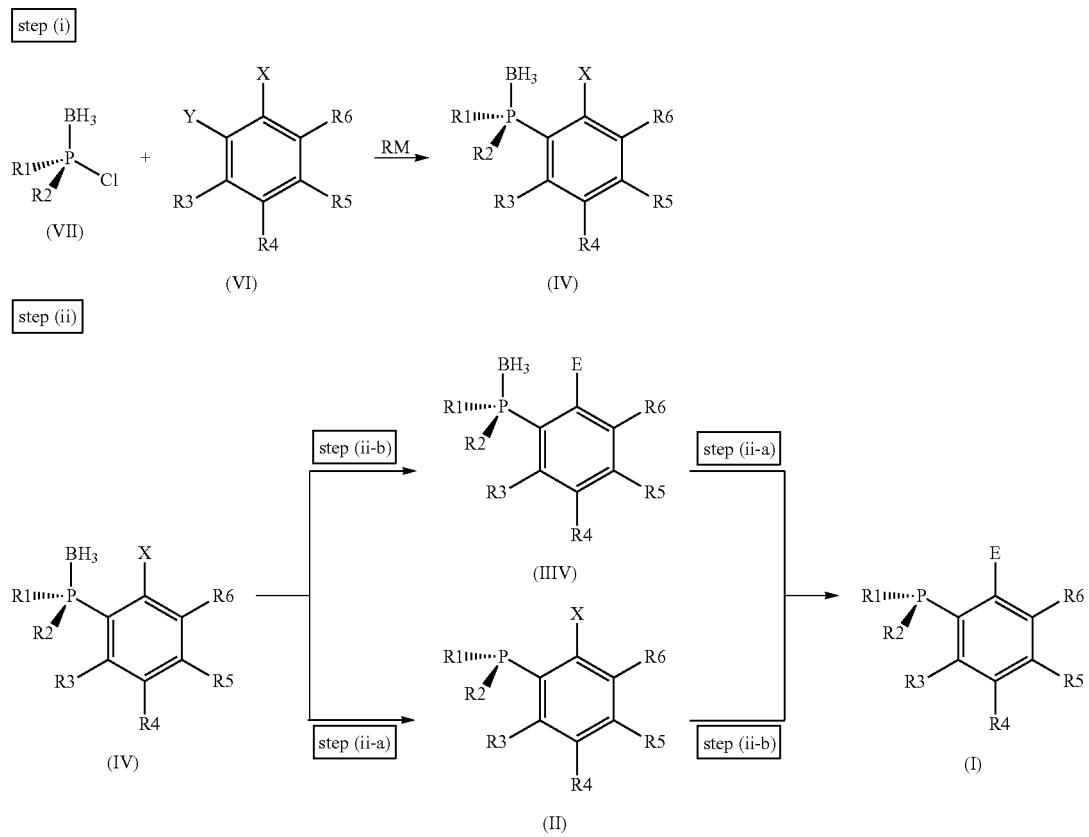

Therefore the present invention relates to a process for producing a compound of formula (I):

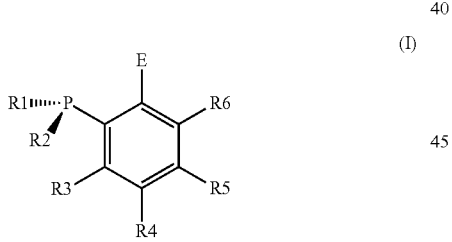

wherein
- R1 and R2 may be the same or different and represent each a substituted or unsubstituted group selected from alkyl, cycloalkyl, aryl, alkyloxy, cycloalkyloxy, aryloxy, alkylamino, cycloalkylamino, arylamino, metallocenyl group;
- R3, R4, R5, R6 may be the same or different and represent each a hydrogen atom or a substituted or unsubstituted group selected from alkyl, cycloalkyl, aryl, alkyloxy, cycloalkyloxy, aryloxy, alkylamino, cycloalkylamino, arylamino;
- E represents a substituted or unsubstituted group selected from PR7R8, P(BH$_3$)R7R8, —C$_6$H$_4$—PR7R8, —C$_6$H$_4$—P(BH$_3$)R7R8, —BR9R10, —CR11R12OH, —COR11, —SiR11R12R13; —SiR11R12-C$_6$H$_4$—PR7R8;

wherein
- R7, R8 may be the same or different and represent each an hydrogen, a substituted or unsubstituted group selected from alkyl, cycloalkyl, aryl, alkyloxy, cycloalkyloxy, aryloxy, alkylamino, cycloalkylamino, arylamino, metallocenyl group,
- R9 and R10 may be the same or different and represent each an halogen, an hydroxyle, a substituted or unsubstituted group selected from alkyloxy, aryloxy, cycloalkyloxy, alkylamino, arylamino, cycloalkylamino, alkyl, cycloalkyl or aryl group; preferably, R9 and R10 are [(CH3)$_2$C—O—]$_2$ or cyclohexyl; in a preferred embodiment, R9 and R10 are the same;
- R11, R12 and R13 may be the same or different and represent each a hydrogen, a substituted or unsubstituted group selected from alkyl, cycloalkyl, aryl, alkyloxy, aryloxy, cycloalkyloxy group;

comprising:
i) reacting chlorophosphine borane (VII)

wherein R1 and R2 are as defined above,
with a reagent RM, in which M is a metal, preferably Li and R is an alkyl or an aryl group; and further reacting the product of this halogen-metal exchange with an aromatic compound of general formula (VI)

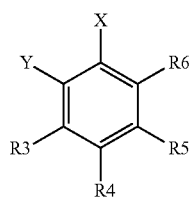
(VI)

wherein X and Y may be the same or different and each represent F, Cl, Br, I, and R3, R4, R5 and R6 are as defines above,
resulting in the corresponding P-chirogenic phosphine borane of formula (IV)

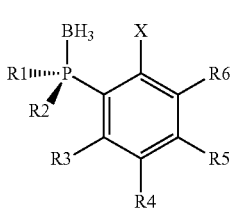
(IV)

wherein X, R1, R2, R3, R4, R5 and R6 are as defined above; and ii) performing two chemical transformations on compound (IV) leading to compound (I), said chemical transformations being a step (ii-a) of removing the borane group and a step (ii-b) of coupling of an electrophilic reagent on the ortho position or of oxidative coupling with an oxidative reagent on the ortho position, optionally followed by an electrophilic coupling on the ortho position; steps (ii-a) and (ii-b) being carried out in any order.

According to one embodiment, in the process of the present invention, compounds (VII), (IV) and (I) are such that when R1 is Me or tBu, then R2 is not tBu or Me respectively.

According to one embodiment, the electrophile is selected from the group comprising boronate reagents, aldehydes, ketones, acyl chlorides, halosilanes, haloalkanes, halophosphines or phosphinites.

According to another embodiment, the oxidative reagent is selected from the group comprising transition metal salts, transition metal complexes, wherein the metal is selected from the group comprising iron, copper.

According to an embodiment, compound (VII) is chiral.

According to an embodiment, compound (IV) first reacts under conditions of step (ii-a) leading to intermediate compound of general formula (II),

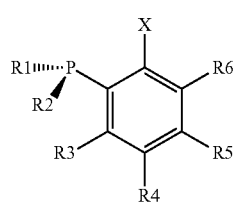
(II)

wherein R1, R2, R3, R4, R5, R6 and X are as defined above.

According to an embodiment, compound (IV) first reacts under conditions of step (ii-b) leading to intermediate compound of general formula (III),

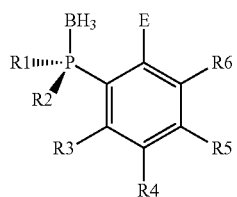
(III)

wherein R1, R2, R3, R4, R5, R6 and E are as defined above.

According to another embodiment, compound (IV) first reacts under conditions of step (ii-a) leading to intermediate compound of general formula (II) and wherein compound (II) then reacts under conditions of step (ii-b) in presence of an oxidative agent and of an excess of compound (II), leading to the compound of homocoupling of general formula (I')

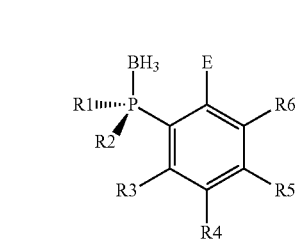
(I')

wherein R1, R2, R3, R4, R5 and R6 are as defined above.

The present invention also relates to a compound of general formula (I)

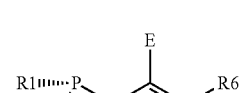
(I)

wherein
E represents a substituted or unsubstituted group selected from PR7R8, P(BH₃)R7R8, —C₆H₄—PR7R8, —C₆H₄—P(BH₃)R7R8, —BR9R10, —CR11R12OH, —COR11, —SiR11R12R13; —SiR11R12-C₆H₄—PR7R8;
wherein
R7, R8 may be the same or different and represent each an hydrogen, a substituted or unsubstituted group selected from alkyl, cycloalkyl, aryl, alkyloxy, cycloalkyloxy, aryloxy, alkylamino, cycloalkylamino, arylamino, metallocenyl group;
R9 and R10 may be the same or different and represent each an halogen, an hydroxyle, a substituted or unsubstituted group selected from alkyloxy, aryloxy, alkylamino, arylamino, cycloalkylamino, alkyl, cycloalkyl or aryl group; preferably, R9 and R10 are [(CH₃)₂C—O—]₂ or cyclohexyl; in a preferred embodiment, R9 and R10 are the same;

R11, R12 and R13 may be the same or different and represent each a hydrogen, a substituted or unsubstituted group selected from alkyl, cycloalkyl, aryl, alkyloxy, aryloxy, cycloalkyloxy group;

R1 and R2 may be the same or different and represent each a substituted or unsubstituted group selected from alkyl, cycloalkyl, aryl, alkyloxy, cycloalkyloxy, aryloxy, alkylamino, cycloalkylamino, arylamino, metallocenyl group, preferably R1 and R2 are different;

R3, R4, R5, R6 may be the same or different and represent each a hydrogen atom or a substituted or unsubstituted group selected from alkyl, cycloalkyl, aryl, alkyloxy, cycloalkyloxy, aryloxy, alkylamino, cycloalkylamino, arylamino;

provided that if E is PR7R8 or P(BH$_3$)R7R8,
when R1 and R2 are Ph and Me or Me and Ph respectively and R3, R4, R5 and R6 are each an hydrogen, R7 and R8 are not Ph and Me respectively;
when R1 and R2 are Me and a $C_2$-$C_6$ alkyl or a $C_2$-$C_6$ alkyl and Me respectively and R3, R4, R5 and R6 are each an hydrogen, R7 and R8 are not Me and a $C_2$-$C_6$ alkyl;
when R1 and R2 are each tBu and R3, R4, R5 and R6 are each an hydrogen, R7 and R8 are not each tBu.

In an embodiment, if E is —C$_6$H$_4$—(PR7R8)$_{ortho}$ and R3, R4, R5 and R6 are each an hydrogen, when {R1, R2} is {Ph, Ph}, {o-Tol, o-Tol}, {Fc, Ph} or {o-An, Ph}, then {R7, R8} is not respectively {Ph, Ph}, {o-Tol, o-Tol}, {Fc, Ph} or {o-An, Ph}.

In an embodiment, if E is CR11R12OH and R3, R4, R5, R6 and R12 are each an hydrogen, then {R1, R2, R11} is not {Fc, Ph, tBu}, {o-An, Ph, t-Bu}, {Fc, Ph, Ph}, {o-An, Ph, Ph}, {Ph, Fc, Ph}, {Ph, Fc, tBu}, {Ph, o-An, Ph}, {Ph, o-An, tBu}.

In an embodiment, if E is CR11R12OH and R3, R4, R5 and R6 are each an hydrogen, then {R1, R2, R11, R12} is not {Ph, Ph, H, H}, {Ph, Ph, Me, H}, {Ph, Ph, Me, Me}, {Ph, Ph, H, —CHMeNBn$_2$}, {Ph, Ph, H, 2-(1-benzyl) pyrrolidinyl}.

In an embodiment, if E is BR9R10 and R3, R4, R5 and R6 are each an hydrogen, then {R1, R2, [R9, R10]} is not {Ph, Ph, [(CH$_3$)$_2$C—O—]$_2$}, {Me, Me, [(CH$_3$)$_2$C—O—]$_2$}, {Ph, Ph, [—O—CH$_2$—C(CH$_3$)$_2$—CH$_2$—O—]}, {Me, Me, [—O—CH$_2$—C(CH$_3$)$_2$—CH$_2$—O—]}, {Ph, Ph, [—O—CH$_2$—CH$_2$—O—]}, {Me, Me, [—O—CH$_2$—CH$_2$—O—]}.

In an embodiment, if E is —SiR11R12R13 and R3, R4, R5 and R6 are each an hydrogen, then {R1, R2, R11, R12, R13} is not {Ph, Ph, Me, Me, Me}, {Me, Me, Me, Me, Me}.

According to one embodiment, groups R1 and R2 are different. In this embodiment, compound (I) is P-chirogenic.

The present invention also relates to the intermediate compound of general formula (II)

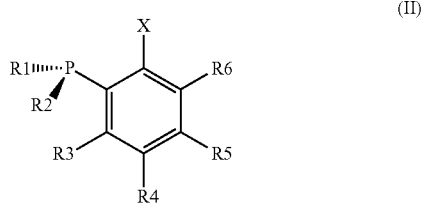

wherein
X represent F, Cl, Br, I; and
R1, R2, R3, R4, R5 and R6 are as defined above,
provided that when X is Br, R3, R4, R5 and R6 are each an hydrogen and R1 is Me or tBu, R2 is not tBu or Me respectively.

In an embodiment, if X is Br and R3, R4, R5 and R6 are each an hydrogen, {R1, R2} are not {Ph, Ph}, {o-Tol, o-Tol}, {Fc, Ph}, {o-An, Ph}, or {Ph, o-An}.

According to one embodiment, groups R1 and R2 are different. In this embodiment, compound (II) is P-chirogenic.

The present invention also relates to the intermediate compound of general formula (III)

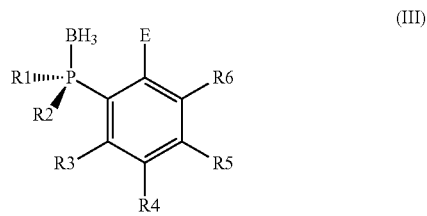

wherein R1, R2, R3, R4, R5, R6 and E are as defined above.

In an embodiment, if E is CR11R12OH and R3, R4, R5 and R6 are each an hydrogen, then {R1, R2, R11, R12} is not {Ph, Ph, H, H}.

According to one embodiment, groups R1 and R2 are different. In this embodiment, compound (III) is chiral.

The present invention also relates to the intermediate compound of general formula (IV)

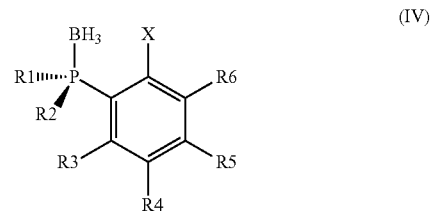

wherein
X represent F, Cl, Br, I; and
R1, R2, R3, R4, R5 and R6 are as defined above,
provided that when X is Br, R3, R4, R5 and R6 are each an hydrogen and R1 is Me or tBu, R2 is not tBu or Me respectively.

In an embodiment, if X is Br; and R3, R4, R5 and R6 are each an hydrogen, then {R1, R2} is not {Ph, Ph}, {o-Tol, o-Tol}, {iPr, iPr}, {cHex, cHex}, {Me, Me}, {o-An, Ph}, {Fc, Ph}, {iPr, Ph}, {cHex, Ph}, {Ph, Fc} or {Ph, o-An}.

In an embodiment, if X is I and R3, R4, R5 and R6 are hydrogens, then {R1, R2} is not {Ph, Ph}, {cHex, cHex}, {Fc, Ph} or {o-An, Ph}.

According to one embodiment, groups R1 and R2 are different. In this embodiment, compound (IV) is P-chirogenic.

The present invention also relates metallic complexes comprising at least one compound of general formula (I), (II), (III) or (IV). In an embodiment, the metallic complexes of the present invention comprise rhodium and one compound of general formula (I), (II), (III) or (IV) as ligand, provided that if the ligand is the compound of general formula (I) in which R1 is Fc, R2 is Ph, R3, R4, R5 and R6 are each an hydrogen and E is —C$_6$H$_4$—(PR7R8)$_{ortho}$, {R7, R8} is not {Ph, Fc} or {Fc, Ph}.

In an embodiment, metallic complexes of the present invention comprise palladium and one compound of the general formula (I), (II), (III) or (IV) as ligand.

DETAILED DESCRIPTION

It is appreciated that in any of the mentioned reactions, any reactive group in the substrate molecules may be protected according to conventional chemical practice. Suitable protecting groups in any of the mentioned reactions are those used conventionally in the art. The methods of formation and removal of such protecting groups are those conventional methods appropriate to the molecule being protected.

Step (i)—Synthesis of Compound (IV) from Chlorophosphine Borane (VII)

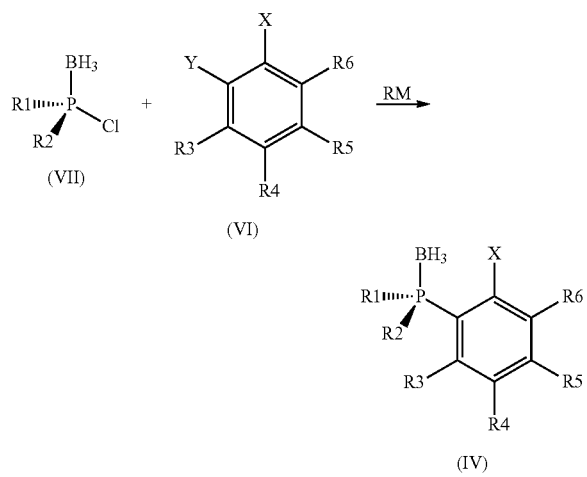

Synthesis of compound (IV), involves a halogen metal exchange that is followed by a reaction with an aromatic compound of general formula (VI):

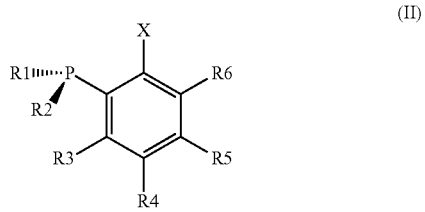

wherein R1, R2, R3, R4, R5, R6 and X are as defined above.

In an embodiment, compound of general formula (VII) is such that R1 is phenyl, cyclohexyl, methyl, i-propyl, o-tolyl, o-anisyl, metallocenyl and R2 is as described above; in a preferred aspect of this embodiment, R2 is also phenyl, cyclohexyl, methyl, i-propyl, o-tolyl, o-anisyl, ferrocenyl, and R1 and R2 are identical or different.

According to a preferred embodiment, reagent RM is t-BuLi.

In another embodiment, compound of general formula (VI) is such that X is Br, or I and Y is Br or I. According to one embodiment, groups X and Y of compound (VI) are the same. According to a preferred embodiment, X and Y are both bromine atoms. According to another embodiment, X and Y are iodine atoms. In these embodiments, R3, R4, R5 and R6 preferably are H or methyl; more preferably, R4 and/or R5 is methyl and the others are H. According to a specific embodiment, compound (VI) is 1,2-dibromobenzene.

In another embodiment, compound of general formula (IV) is such that X is Br or I, preferably Br, R1 is phenyl, cyclohexyl, methyl, i-propyl, o-tolyl, o-anisyl, ferrocenyl and R2 represent each a substituted or unsubstituted group selected from alkyl, cycloalkyl, aryl, alkyloxy, cycloalkyloxy, aryloxy, alkylamino, cycloalkylamino, arylamino, ferrocenyl group, provided that when R1 is Me, R2 is not tBu; preferably R2 is phenyl, cyclohexyl, methyl, i-propyl, o-tolyl, o-anisyl, ferrocenyl; R1 and R2 are identical or different; R3, R4, R5 and R6 preferably are H or methyl; more preferably, R4 and/or R5 is methyl and the others are H.

According to one embodiment, step (i) is carried out under cooling conditions, at a temperature ranging from −110° C. to −10° C., preferably from −90° C. to −60° C., and even more preferably at −78° C.

According to one embodiment, halogen metal exchange is carried out in presence of reagent RM, in which M is a metal, preferably Li and R is an alkyl or an aryl group. In a preferred embodiment, RM reagent is tBuLi.

According to an embodiment, RM reagent is in solution in pentane, heptane or THF. In another embodiment, the concentration of RM reagent is ranging from 1.0 to 2.0M and preferably at 1.6 M.

According to one embodiment, halogen metal exchange is carried out in presence of 2 to 6 equivalents, preferably of 2 to 3 equivalents of RM reagent and even more preferably of 2.4 equivalents of RM reagent.

According to one embodiment, the solvent used during the subsequent addition of aromatic reagent of general formula (VI) is selected from the group comprising tetrahydrofuran, ether, dimethylether, dioxane, benzene, toluene, xylenes, dimethylsulfoxide or a mixture of these ones. According to a preferred embodiment, the solvent used is tetrahydrofuran.

According to an embodiment, compound (IV) is obtained without racemization. According to one embodiment, compound (IV) is obtained with an enantiomeric excess ranging from 0 to 100%, preferably from 85 to 100%.

Synthesis of Chlorophosphine Borane (VII) by Acidolysis of Aminophosphine Borane (VIII)

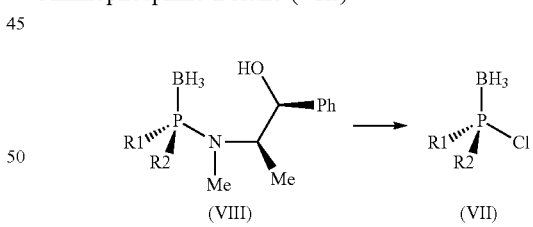

According to one embodiment, compound (VII) may be obtained by an acidolysis of compound of general formula (VIII)

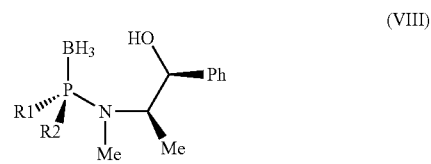

wherein R1 and R2 are as defined above.

In one embodiment, the process of the invention comprises a preliminary step of acidolysis of compound (VIII) leading to compound (VII).

According to one embodiment, the acydolysis of compound (VIII) is carried out in presence of 2 to 20 equivalents, preferably of 4 to 16 equivalents and event more preferably 4.0 equivalent of acid reagent.

According to one embodiment, the solvent used in the acidolysis is selected from the group comprising tetrahydrofuran, ether, dimethylether, dioxane, benzene, toluene, xylenes, dimethylsulfoxide or a mixture of these ones. According to a preferred embodiment, the solvent used in the acidolysis step is toluene.

According to one embodiment, the acid used for the acidolysis is an acid selected from the group comprising $H_2SO_4$/NaCl, HBr gas, HI, MsOH, TsOH, a solution of dry HCl or a mixture thereof.

According to one embodiment, dry HCl is in solution in a solvent selected in the group comprising toluene, diethylether, dioxane, cyclopentylmethyl ether, ethyl acetate, methanol, ethanol, 2-propanol, butanol and acetic acid. In a preferred embodiment, dry HCl is dissolved in toluene.

In an embodiment, the acidolysis is performed preferably at 20° C.

In an embodiment, intermediate compound (VII) is isolated after filtrating the reaction mixture and removing half of the solvent under reduced pressure.

In one embodiment, compound (VII) is obtained without racemization. According to one embodiment, compound (VII) is obtained with an enantiomeric excess ranging from 0 to 100%, preferably from 85 to 100%.

Alternative Route of Synthesis of Compound (IV)

In one embodiment, step (i) further comprises a first intermediate step (a) of protonation of the product of the halogen-metal exchange leading to compound (V)

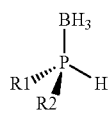

(V)

wherein R1 and R2 may be the same or different and represent each a substituted or unsubstituted group selected from alkyl, cycloalkyl, aryl, alkyloxy, cycloalkyloxy, aryloxy, alkylamino, cycloalkylamino, arylamino, metallocenyl group, provided that when R1 is Me or tBu, R2 is not tBu or Me respectively;

and further comprises a second intermediate step (b) of reaction of compound (V) with a reagent RM in which M is a metal, preferably Li or a magnesium organic compound MgZ wherein Z is halide, and R is an alkyl or an aryl group, before further reacting this intermediate compound with compound (VI).

This alternative step (i) is represented on the scheme below:

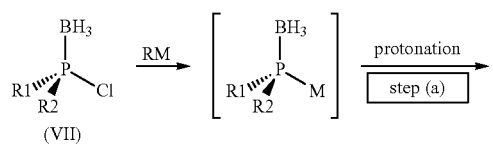

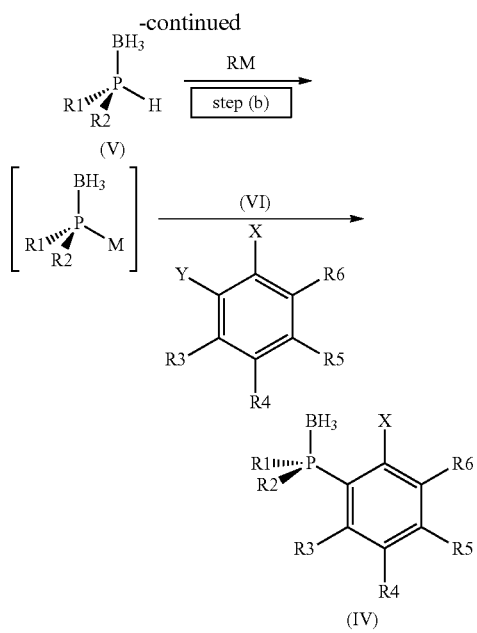

One interest of this alternative route of synthesis is that compound (V) may be purified. This is especially interesting in the case wherein compound (VII) is obtained from compound (VIII) as described above.

According to one embodiment, the process of the present invention comprises further intermediate steps (a) and (b) and compounds (VII), (V), (IV) and (I) are such that when R1 is Me or tBu, then R2 is not tBu or Me respectively.

Without willing to be bound to a theory, it is suggested that compound (VI) forms in situ a benzyne intermediate in presence of the organometallic reagent RM. It is thought that benzyne intermediate is obtained by an exchange between groups X and Y of compound (VI) and the metal M, followed by the elimination of MX and MY. At the same time, compound (V) is deprotonated by the organometallic reagent RM to form the corresponding anion. The very electrophile benzyne then reacts with the deprotonated compound (V) to form the corresponding o-metallated phosphine borane which converts into (IV) by another exchange between metal and group X.

In an embodiment, compound of general formula (V) is such that R1 is phenyl, cyclohexyl, methyl, i-propyl, o-tolyl, o-anisyl, metallocenyl and R2 is as described above; in a preferred aspect of this embodiment, R2 is also phenyl, cyclohexyl, methyl, i-propyl, o-toluene, o-anisyl, ferrocenyl, and R1 and R2 are identical or different.

According to a preferred embodiment, reagent RM is nBuLi.

In another embodiment, compound of general formula (VI) is such that X is Br, or I and Y is Br or I. According to one embodiment, groups X and Y of compound (VI) are the same. According to a preferred embodiment, X and Y are both bromine atoms. According to another embodiment, X and Y are iodine atoms. In these embodiments, R3, R4, R5 and R6 preferably are H or methyl; more preferably, R4 and/or R5 is methyl and the others are H. According to a specific embodiment, compound (VI) is 1,2-dibromobenzene.

In another embodiment, compound of general formula (IV) is such that X is Br or I, preferably Br, R1 is phenyl, cyclohexyl, methyl, i-propyl, o-tolyl, o-anisyl, ferrocenyl and R2 represent each a substituted or unsubstituted group selected from alkyl, cycloalkyl, aryl, alkyloxy, cycloalkyloxy, aryloxy, alkylamino, cycloalkylamino, arylamino, ferrocenyl group, provided that when R1 is MeR2 is not tBu; preferably R2 is phenyl, cyclohexyl, methyl, i-propyl, o-tolyl, o-anisyl, ferrocenyl; R1 and R2 are identical or different; R3, R4, R5 and R6 preferably are H or methyl; more preferably, R4 and/or R5 is methyl and the others are H.

According to one embodiment, step (i) is usually carried out under cooling conditions, at a temperature ranging from −90° C. to 50° C., preferably from −78° C. to −60° C.

According to one embodiment, step (i) is usually carried out in presence of 0.5 to 3 equivalents, preferably of 1.1 to 1.2 equivalents of RM reagent.

According to one embodiment, the solvent used in step (i) is selected from the group comprising tetrahydrofuran, ether, dimethylether, dioxane, benzene, toluene, xylenes, dimethylsulfoxide or a mixture of these ones. According to a preferred embodiment, the solvent used in step (i) is tetrahydrofuran.

According to one embodiment, intermediate compound (IV) is purified by using chromatographic techniques or by recrystallization.

According to one embodiment, compound (IV) is obtained with an enantiomeric excess ranging from 0 to 100%, preferably from 85 to 100%.

According to one embodiment, compound (IV) is obtained without racemization, preferably with an enantiomeric excess of more than 85%, preferably of more than 90%.

Step (ii)—Synthesis of Compound (I) from Compound (IV)
Step (ii-a)—Removing of Borane Group

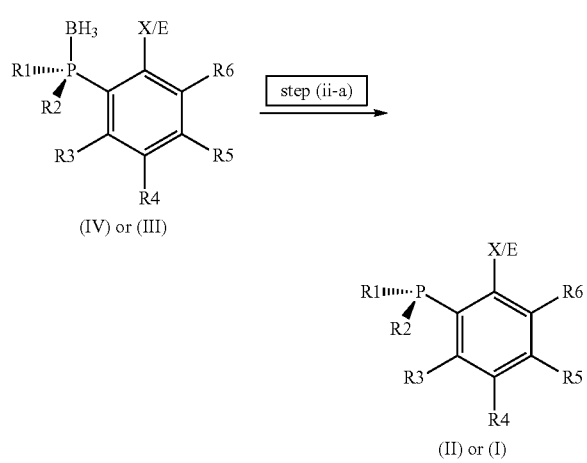

Synthesis of compound (I) from intermediate compound (III) and synthesis of intermediate compound (II) from intermediate compound (IV), by step (ii-a), involve the deprotection of the phosphorus atom by removing of the borane protective group.

According to one embodiment, removing of the borane group by step (ii-a) is carried out by classical methods of removal of the borane group. According to a preferred embodiment, removing of the borane group by step (ii-a) is achieved using 1,4-diazabicyclo[2.2.2]octane (DABCO) as reactive agent according to the procedure described in Brisset H., Gourdel Y., Pellon P. and Le Corre M., Tetrahedron Lett., 1993, 34, 4523-4526. According to another embodiment, removing of the borane group by step (ii-a) is carried out by warming compound (III) in ethanol, amines or olefines, and recrystallizing of the resulting compound (I).

According to one embodiment, removing of the borane group by step (ii-a) occurs without racemization.

In an embodiment, compound (II) is obtained using a one pot procedure starting from compound (VIII), i.e. without isolating intermediate compounds (VII) and (IV).

Step (ii-b)—Electrophilic or Oxidative Coupling

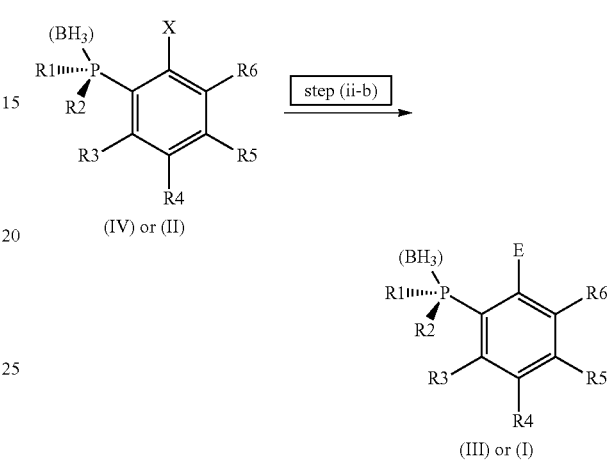

Synthesis of compound (I) from intermediate compound (II) and synthesis of intermediate compound (III) from intermediate compound (IV), by step (ii-b), involve an electrophilic coupling or an oxidative coupling optionally followed by an electrophilic coupling.

According to one embodiment, step (ii-b) involves an organometallic agent RM and an electrophilic agent. According to another embodiment, step (ii-b) involves an organometallic agent RM and an oxidative agent. According to a further embodiment, step (ii-b) involves an organometallic agent RM, an oxidative agent and an electrophilic agent.

According to one embodiment, the organometallic agent RM is selected from the group comprising nBuLi, sBuli, tBuLi, PhLi, Grignard reagents such as i-PrMgCl. According to a preferred embodiment, the organometallic agent RM is nBuLi, According to one embodiment, the electrophilic agent is selected from the group comprising boron reagents, aldehydes, ketones, acyl chlorides, halosilanes, haloalkanes, halophosphines, phosphinites, Michael acceptors such as α,β-insaturated ester, α,β-insaturated ketones, α,β-insaturated phosphine derivatives. According to a preferred embodiment, the electrophilic agent is selected from the group comprising ClB(c-Hex)$_2$, PhCHO, tBuCHO, tBuCOCl, (Me)$_3$SiCl, (Me)$_2$SiCl$_2$, MeI, ClP(Ph)$_2$, ClP(c-Hex)$_2$, ClP(i-Pr)$_2$, ClP(o-Tol)$_2$, ClP(p-Tol)$_2$, ClP(p-CF$_3$Ph)$_2$, PhO—P(Ph)(o-Tol), PhO—P(Ph)(o-An).

According to one embodiment, the oxidative agent is selected from the group comprising transition metal salts, transition metal complexes, wherein the metal is selected from the group comprising iron, copper, cerium, palladium. According to a preferred embodiment, the oxidative agent is selected from the group comprising Fe(acac)$_3$, FeCl$_3$, Cu(AcO)$_2$. Without willing to be bound to a theory, it is suggested that reactive group X of compound (IV) or (II) is exchanged with the metal of the organometallic agent RM. Reaction of the resulting anion with an electrophilic agent then leads to the production of compound of the general formula (I) or (III). The anion may also reacts with a metal salt to produce the transmetallation adduct to afford the homocoupling product (III), (I) or (I') by oxidative coupling, or the ortho-substituted compounds (III) or (I) by reaction with an electrophilic reagent. When the anion obtained from compound (IV) or (II) is first reacted with an oxidative agent with an excess of compound (IV) or (II), homocoupling reaction may occur, leading to diphosphinic derivatives with a biphenyl bridge of formula (I').

According to an embodiment, no homocoupling reaction occurs in the present invention.

According to one embodiment, step (ii-b) is usually carried out at a temperature ranging from −90° C. to 50° C., preferably from −78° C. to 20° C.

According to one embodiment, the solvent used in step (ii-b) is selected from the group comprising tetrahydrofuran, ether, dimethylether, dioxane, benzene, toluene, xylene, dimethylsulfoxide or a mixture of these ones. According to a preferred embodiment, the solvent used in step (ii-b) is tetrahydrofuran.

Use of Compounds (I) in Asymmetric Catalysis

Compounds (I) of the present invention are useful in asymmetric catalysis by transition metal complexes or organocatalysis. Especially, compounds (I) may be used in catalyzed asymmetric reactions such as hydrogenation, allylation, C—C bond formation, hydroformylation or carbonylation reactions.

According to one embodiment, compound (I) is used as a ligand of a transition metal such as rhodium or palladium, ruthenium, iridium. Complexes of transition metal according to this embodiment may be suitable for asymmetric catalyzed reactions, preferably in allylation or hydrogenation reactions.

Intermediates compounds (II), (III) and (IV) may also be useful in asymmetric catalysis by transition metal complexes, organocatalysis or stereoselective synthesis.

EXAMPLES

The present invention is further illustrated by the following examples which are provided by way of illustration only and should not be considered to limit the scope of the invention.

A. Generalities

Material and Methods

All reactions were carried out under an Ar atmosphere in dried glassware. Solvents were dried and freshly distilled under an Ar atmosphere over sodium/benzophenone for THF, diethylether, toluene and benzene, $CaH_2$ for $CH_2Cl_2$. Hexane and isopropanol for HPLC were of chromatography grade and used without further purification. s-Butyllithium (1.4M in cyclohexane), t-butyllithium (1.6M in pentane), isopropyllithium (0.7M in pentane), ferrocene, 2-bromoanisole, methyl iodide, $BH_3.SMe_2$, 1,4-diazabicyclo[2.2.2]octane (DABCO), 2-isopropoxy-4,4,5,5-tetramethyl-1,3,2-dioxaborolane, were purchased from Aldrich, Acros or Alfa Aesar, and used as received. (+)- and (−)-ephedrine were purchased from Aldrich and dried by azeotropic shift of toluene on rotary evaporator. The toluenic HCl solution (0.2-0.4 M) was obtained by bubling HCl gas in toluene and titrated by acidimetry before use. The (2S,4R,5S)-(−)-3,4-dimethyl-2,5-diphenyl-1,3,2-oxazaphospholidine-2-borane and its enantiomer (2R,4S,5R)-(+), were prepared from the appropriate (+)- or (−)-ephedrine, as previously described (S. Jugé, Phosphorus, Sulfur and Silicon & Related Compounds, 2008, 183(2-3), 233-248; Darcel C., Uziel J. and Jugé S., Phosphorus Ligands in Asymmetric Catalysis and Applications, A. Bmrner (Ed.), 208, Wiley-VCH; Chaux F., Frynas S., Laureano H., Salomon C., Morata G., Auclair M-L., Stephan M., Merdés R., Richard P., Ondel M-J., Henry J. C., Bayardon J., Darcel C., Jugé S., C. R. Chimie, 2010, 13, 1213-1226).

Chiral HPLC analysis were performed on SHIMADZU 10-series apparatus, using chiral columns (Chiralcel OD-H, Chiralcel AD, Chiralcel OJ, Lux 5µ-cellulose-2), and with hexane/propan-2-ol mixtures as the mobile phase (Flow rate 1 mL·min$^{-1}$; UV detection λ=254 nm). Thin layer chromatography (TLC) was performed on 0.25 mm E. Merck precoated silica gel plates and exposed by UV, potassium permanganate or iodine treatment. Flash chromatography was performed with the indicated solvents using silica gel 60 A, (35-70 µm; Acros) or aluminium oxide 90 standardized (Merck). All NMR spectra data were recorded on BRUKER AM 250, 300 AVANCE, 500 AVANCE DRX and 600 AVANCE II spectrometers at ambient temperature. Data are reported as s=singlet, d=doublet, t=triplet, q=quartet, m=multiplet, brs=broad singlet, brd=broad doublet, dhept=doublet of heptuplet, coupling constant(s) in Hertz. Melting points were measured on a Kofler bench melting point apparatus and are uncorrected. Optical rotations values were recorded at 20° C. on a Perkin-Elmer 341 polarimeter, using a 10 cm quartz vessel. Infrared spectra were recorded on a Bruker Vector 22 apparatus. Mass and HRMS spectra were recorded on Mass, Bruker ESI micro TOF-Q apparatus, at the Université de Bourgogne (Dijon). The major peak m/z was mentioned with the intensity as a percentage of the base peak in brackets. Elemental analyses were measured with a precision superior to 0.3% at the Microanalysis Laboratories of the Universités P. & M. Curie (Paris) and Bourgogne (EA 1108 CHNS-O FISONS Instrument). X-Ray analyses were performed at the Université de Bourgogne, and the data were collected at 115 K on a Bruker Nonius Apex II CCD system using graphite-monochromated Mo-Kα radiation. The structures were solved by direct methods (SIR92) and refined with full-matrix least-squares methods based on $F^2$ (SHELXL-97) with the aid of the WINGX program. All non-hydrogen atoms were refined with anisotropic thermal parameters. Hydrogen atoms were either included in theirs calculated positions or found in Fourier difference maps ($CH_3$ and $BH_3$).

A.1. Preparation of Aminophosphine Boranes

Preparation of Organolithium Reagents

Aryllithium reagents by metal-halogen exchange: In a two necked-flask equipped with a magnetic stirrer and an argon inlet, 1 equiv. of sec-butyllithium is added. The mixture is cooled to 0° C. and 1 equiv. of 2-bromoanisole is slowly added with a syringe while stirring. After the formation of a white precipitate, the mixture is stirred for 1 h at 0° C. The organolithium reagent is dissolved with a minimum of dry THF before use.

Preparation of Ferrocenyllithium by Deprotonation of the Ferrocene

A 250 mL three-necked flask equipped with a magnetic stirrer under an argon atmosphere was charged with ferrocene (0.74 g, 4 mmol) and THF (10 mL). At 0° C., t-BuLi (2.75 mL, 1.6 M in hexane, 4.4 mmol) was added dropwise, and the reaction mixture was stirred at 0° C. for 1 h, before use.

General procedure

In a 100 mL three-necked flask, equipped with a magnetic stirrer and an argon inlet, 5 mmol of the oxazaphospholidine borane complex were dissolved in 5 mL of anhydrous THF. The mixture was cooled at −78° C. and 2 equiv. (10 mmol)

of the organolithium reagent were slowly added. The resulting mixture was stirred and warmed to 0° C. (or RT) until the starting material had completely reacted. The reaction was monitored by TLC over silica ($CH_2Cl_2$ as eluent), and was finally hydrolyzed at 0° C. with 2 mL of water. The THF was removed under reduced pressure and the aqueous layer was extracted several times with dichloromethane. The combined organic phases were dried over $MgSO_4$ and the solvent was removed. The residue was purified on a short column of silica gel, using a mixture of toluene/AcOEt 95:5 as eluent, to afford the aminophosphine boranes. The aminophosphine boranes can be recrystallized using a mixture hexane/isopropanol 7:3.

The ($S_p$)-(+)-N-methyl-N-[(1R,2S)(1-hydroxy-2-methyl-1-phenyl-2-propyl)]amino-o-anisylphenyl phosphine borane were prepared from the (−)-ephedrine according to the published procedure.

($S_p$)-(+)-N-methyl-N-[(1R,2S)(1-hydroxy-1-phenyl-prop-2-yl]aminoferrocenylphenyl phosphine borane Yield=80%; Orange crystals; $[\alpha]_D^{20}$=+113.9 (c 1.0, $CHCl_3$); $R_f$=0.62 (toluene/EtOAc (9:1)); IR (KBr, ν $cm^{-1}$): 3500 (O—H), 2372 (B—H), 1455, 1437, 1386, 1367, 1217, 1163, 1106, 1063, 1022, 998, 956, 884, 822, 763, 746, 721, 698, 646, 614; $^1$H NMR ($CDCl_3$, 300.13 MHz) δ 0.20-2.00 (m, 3H), 0.91 (d, J=6.3 Hz, 3H), 2.05 (brs, 1H), 2.38 (d, J=8.4 Hz, 3H), 4.16-4.25 (m, 1H), 4.23-4.27 (m, 1H), 4.30 (brs, 5H), 4.51 (d, J=11.7 Hz, 2H), 4.58-4.62 (m, 1H), 4.87 (d, J=5.7 Hz, 1H), 7.28-7.46 (m, 10H); $^{31}$P NMR ($CDCl_3$, 121.5 MHz) δ+70.7 (m); $^{13}$C NMR ($CDCl_3$, 75.0 MHz) δ 13.7, 31.3, 40.3, 58.4 (d, J=10.6 Hz), 70.9, 71.9, 73.0, 79.6, 127.3, 128.4, 128.8, 128.9, 129.1, 131.1, 132.2 (d, J=9.8 Hz), 143.3; Anal. calcd for $C_{26}H_{31}BFeNOP$ (471.17): C, 66.28; H, 6.63; N, 2.97. found: C, 66.33; H, 6.83; N, 3.02.

(Rp)-(−)-N-methyl-[(1R,2S)(2-hydroxy-1-phenyl)ethyl]-aminocyclohexylphenyl-phosphine borane Yield=87%; White crystals; m.p. 98° C.; $[\alpha]_D^{20}$=−28.5 (c=0.7, $CHCl_3$); $R_f$=0.26 (toluene). IR (KBr, ν $cm^{-1}$) 3538 (O—H), 3029-2857 (C—H), 2369 (B—H), 1492, 1452, 1436, 1368, 1257, 1221, 1159, 1109, 1086, 1000, 961, 887, 758, 742, 695; $^1$H NMR ($CDCl_3$) δ (ppm) 0.10-1.60 (m, 3H, $BH_3$), 1.15 (d, 3H, $^3J_{HH}$=6.9, C—$CH_3$), 1.20-1.90 (m, 10H, $CH_2$), 2.27-2.34 (m, 1H, CyH-P), 2.63 (d, 3H, $^3J_{PH}$=7.2, N—$CH_3$), 4.02-4.20 (m, 1H, CHN), 4.80 (d, 1H, $^3J_{HH}$=4.0, CHO), 7.10-7.65 (m, 10H, H arom.); $^{13}$C NMR ($CDCl_3$) δ (ppm) 12.2 (d, $J_{PC}$=3.8, C—$CH_3$), 25.9 ($CH_2$), 26.6-27.0 ($CH_2$), 29.3 (d, $J_{PC}$=3.3, N—$CH_3$), 32.6 (d, $^1J_{PC}$=43.7, CyCH-P), 58.3 (d, $^2J_{PC}$=8.1, CHN), 78.6 (d, $^3J_{PC}$=2.3, CHO), 126.0 (C arom.), 127.4 (C arom.), 128.2 (C arom.), 128.3 (d, $J_{PC}$=9.4, C arom.), 130.5 (d, $J_{PC}$=2.1, C arom.), 130.8 (d, $J_{PC}$=55.7, C arom.), 131.2 (d, $J_{PC}$=9.1, C arom.), 142.5 (C arom.); $^{31}$P NMR ($CDCl_3$) δ (ppm)+73.7 (m); MS (EI) m/z (relative intensity) 368 ($M^+$-H; 100), 356 ($M^+$+H—$BH_3$; 25), 312 (10), 262 (15), 248 (15), 209 (10), 193 (25), 166 (10), 148 (20); HRMS (DCI, $CH_4$) Calcd for $C_{22}H_{32}BNOP$ [$M^+$-H] 368.2315. found: 368.2319; Anal. Calcd for $C_{22}H_{32}BNOP$ (369.2883): C, 71.55; H, 9.01; N, 3.79. found: C, 71.71; H, 9.13; N, 3.67.

($R_p$)-(+)-N-methyl-N-[(1R,2S)(1-hydroxy-1-phenyl-prop-2-yl]aminophenyl-i-propyl phosphine borane Yield=80%; Colorless oil; $[\alpha]_D^{20}$=+31.7 (c 0.6, $CHCl_3$); $R_f$=0.25 ($CH_2Cl_2$); IR (ν $cm^{-1}$): 3510 (O—H), 2974-2874 (C—H), 2380 (B—H), 1453, 1436, 1386, 1220, 1173, 1107, 1071, 1023, 1005, 955, 914, 884, 742, 727, 698, 645, 619, 582; $^1$H NMR ($CDCl_3$, 300.13 MHz) δ 0.10-0.90 (m, 3H), 0.96 (dd, J=17.1 and 7.2 Hz, 3H), 1.03 (d, J=6.9 Hz, 3H), 1.09 (dd, J=15.3 and 7.2 Hz, 3H), 2.50 (d, J=7.2 Hz, 3H), 2.47-2.61 (m, 1H), 3.97-4.09 (m, 1H), 4.68 (d, J=4.8 Hz, 1H), 7.07-7.19 (m, 3H), 7.23-7.37 (m, 5H), 7.46 (m, 2H); $^{31}$P NMR ($CDCl_3$, 121.5 MHz) δ+76.4; $^{13}$C NMR ($CDCl_3$, 75.0 MHz) δ 12.9 (d, J=3.8 Hz), 17.5 (d, J=5.3 Hz), 22.8 (d, J=44.5 Hz), 29.9 (d, J=3.0 Hz), 59.1 (d, J=7.6 Hz), 79.2 (d, J=2.3 Hz), 126.7, 128.1, 128.9, 129.0 (d, J=2.3 Hz), 131.7 (d, J=55.9 Hz), 131.8 (d, J=9.1 Hz), 143.2; MS (EI) m/z (relative intensity) 352 ($M^+$+Na; 100), 338 ($M^+$-$BH_3$+Na; 95); HRMS (ESI) calcd for $C_{19}H_{29}BNNaOP$ [M+Na]$^+$ 352.1962. found: 352.1976.

A.2. Preparation of Secondary Phosphine Boranes (V)
General procedure

In a 250 mL two-necked flask, equipped with a magnetic, an argon inlet, and a rubber septum were introduced 6 mmol of the aminophosphine borane. A solution of HCl in toluene (36 mmol, 10 (ex: i-Pr) −15 (ex: Fc) equiv.) was next added under stirring at room temperature, without previous dissolution of the aminophosphine borane. After 1 to 48 h, the progress of the reaction being monitored by TLC, the precipitate of ephedrine hydrochloride was filtered off with a Millipore 4 μm filter, and the excess of HCl was removed by several vacuum/argon cycles. The tert-butyllithium (12 mmol, 2 equiv.) is added dropwise over 4 minutes at −85° C. to the vigorously stirred toluene solution of the chlorophosphine borane. After stirring for 5 minutes at −85° C., THF (6 mL) is added dropwise over 1 minute and the reaction mixture turned deep yellow. Acetic acid (2.8 mL) was readily added in once. The reaction mixture became bright white and is readily hydrolyzed (50 mL of water). The aqueous phase was extracted several times with $CH_2Cl_2$. The combined organic layers were dried over $MgSO_4$, and the solvent was removed. The residue was purified by chromatography on silicagel to afford the pure secondary phosphine borane (V).

A.2.1. (S)-(−)-o-Anisylphenylphosphine borane (V-f)

Yield=98% (ee=97%); white solid; $R_f$=0.50 (petroleum ether/toluene 1:1); $[\alpha]_D^{20}$=−92 (c 0.4, $CHCl_3$); IR (ν $cm^{-1}$) 3206, 3001-2837 (C—H), 2379 and 2259 (B—H), 1588, 1575, 1477, 1463, 1454, 1438, 1433, 1296, 1278, 1247, 1186, 1159, 1134, 1112, 1084, 1072, 1061, 1042, 1023, 974, 953, 912, 899, 858, 797, 767, 739, 728, 696; $^1$H NMR ($CDCl_3$): δ (ppm) 0.50-1.70 (m, 3H), 3.83 (s, 3H), 6.54 (dq, J=396 Hz, J=6.8 Hz, 1H), 6.93 (dd, J=8.3 Hz, J=3.5 Hz, 1H), 7.04-7.08 (m, 1H) 7.36-7.54 (m, 4H), 7.64-7.80 (m, 3H); $^{13}$C NMR ($CDCl_3$): δ (ppm) 55.9, 110.9 (d, J=3.9 Hz), 114.6 (d, J=55.6 Hz), 121.4 (d, J=12.4 Hz), 126.9 (d, J=58.3 Hz), 128.8 (d, $J_{PC}$=10.4 Hz), 131.2 (d, J=2.3 Hz), 132.9 (d, J=9.5 Hz), 134.0 (d, J=2.2 Hz), 135.0 (d, J=13.6 Hz), 160.7 (d, J=1.1 Hz); $^{31}$P NMR ($CDCl_3$): δ (ppm) −15.3; MS (EI) m/z (relative intensity) 229 ($M^+$-H), 294 ($M^+$-$BH_3$; 100), 226 (15), 217 (50), 186 (55), 170 (10), 121 (20), 56 (10); HRMS (ESI) calcd for $C_{13}H_{16}BNaOP$: 253.0924. Found: 253.0926. The enantiomeric excess of the o-anisylphenylphosphine borane (V-f) was determined by HPLC analysis on a Chiralcel OD-H column, eluent: hexane/isopropyl alcohol 98:2, 1 mL/min, λ=254 nm: (R), $t_R$=9.75 min; (S)-enantiomer, $t_R$=10.50 min.

A.2.2. (S)-Ferrocenylphenylphosphine borane (V-g)

Yield=60% (94% ee); orange oil; $R_f$=0.5 (petroleum ether/toluene 1:1); IR (ν $cm^{-1}$) 3200-3000 (C—H), 2385 and 2346 ($BH_3$), 2253, 1665, 1484, 1437, 1412, 1387, 1366, 1313, 1157, 1133, 1107, 1061, 1027, 1001, 913, 886, 824, 741, 696; $^1$H NMR (CDCl$_3$): δ (ppm) 0.87-1.67 (m, 3H), 4.29 (s, 5H), 4.49-4.54 (m, 4H), 6.23 (qd, J=381 Hz, J=6.7 Hz, 1H), 7.42-7.54 (m, 3H), 7.65-7.71 (m, 2H); $^{13}$C NMR (CDCl$_3$): δ (ppm) 64.1 (d, J=67 Hz), 69.8, 72.1 (td, J=22.3 Hz, J=7.1 Hz), 73.0 (d, J=15 Hz), 128.0 (d, J=57.2 Hz), 128.7 (d, J=10.1 Hz), 131.1 (d, J=2.0 Hz), 132.1 (d, J=9.2 Hz); $^{31}$P NMR (CDCl$_3$): δ (ppm) –6.5. The enantiomeric excess of the ferrocenylphenylphosphine borane (V-g) was determined by HPLC analysis on a Chiralpack AD column, eluent: hexane/isopropylic alcohol 95:5, 1 mL/min, λ=254 nm: (R), $t_R$=8.64 min; (S)-enantiomer, $t_R$=13.06 min.

A.2.3. (R)-(–)-Phenyl-i-propylphosphine borane (V-h)

Yield=41% (ee=95%); colorless oil; $R_f$=0.70 (petroleum ether/ethyl acetate 3/1); $[α]^{20}_D$=–5.0 (c 0.4, CHCl$_3$); IR (ν cm$^{-1}$) 3218, 2966-2873 (C—H), 2386-2348 (B—H), 1439, 1117, 1070, 914, 879, 656; $^1$H NMR (CDCl$_3$): δ (ppm) 0.10-0.90 (m, 3H), 1.19 (ddd, J=16.6 Hz, J=13.8 Hz, J=7.1 Hz, 6H), 2.23-2.28 (m, 1H), 5.26 (ddq, J=365.3 Hz, J=6.8 Hz, J=4.1 Hz, 1H), 7.46-7.56 (m, 3H), 7.66-7.72 (m, 2H); $^{13}$C NMR (CDCl$_3$): δ (ppm) 17.8 (d, J=38.5 Hz), 23.8 (d, J=35.5 Hz), 124.8 (d, J=53.6 Hz), 128.9 (d, J=9.8 Hz), 131.7 (d, J=3.0 Hz), 133.4 (d, J=8.3 Hz); $^{31}$P NMR (CDCl$_3$) δ (ppm): +15.6; MS (EI) m/z (relative intensity) 191 (M-BH$_3$+O+Na$^+$; 100); HRMS (ESI) calcd for C$_9$H$_{16}$BNaP 189.0977. Found: 189.0940. The enantiomeric excess of the Phenyl-i-propylphosphine borane (V-h) was determined by HPLC analysis on a Lux 5µ-cellulose 2 column, eluent: hexane/isopropylic alcohol 99:1, 0.5 mL/min, λ=210 nm: (R), $t_R$=27.06 min; (S)-enantiomer, $t_R$=29.87 min.

A.2.4. (R)-Cyclohexylphenylphosphine borane (V-i)

Yield=91% (95% ee); colorless oil; $R_f$=0.75 (toluene); IR (ν cm$^{-1}$) 3341, 3056, 2930-2854 (C—H), 2388-2251, 1486, 1450, 1437, 1346, 1293, 1272, 1203, 1179, 1123, 1059, 1047, 1028, 1002, 911, 875, 845, 822, 748, 702, 675, 592, 508, 488, 480, 429, 406; $^1$H NMR (CDCl$_3$): δ (ppm) 0.40-1.0 (m, 3H), 1.15-1.40 (m, 5H), 1.68-1.73 (m, 1H), 1.79-1.90 (m, 4H), 1.93-2.02 (m, 1H), 5.23 (dqd, J=365 Hz, J=6.8 Hz, J=4.5 Hz, 1H), 7.47-7.51 (m, 2H), 7.53-7.57 (m, 1H) 7.66-7.70 (m, 2H); $^{13}$C NMR (CDCl$_3$): δ (ppm) 26.0, 26.7-26.8 (m), 28.1, 28.6, 33.7 (d, J=34.8 Hz), 125.2 (d, J=53.1 Hz), 129.2 (d, J=9.6 Hz), 131.9, 133.8 (d, J=7.8 Hz); $^{31}$P NMR (CDCl$_3$) δ (ppm): +11.6; MS (MALDI) m/z (relative intensity) 229 (M+Na$^+$; 100), 215 (M-BH$_3$+Na$^+$; 5), 193 (M-BH$_3$+H$^+$, 15); HRMS (ESI) calcd for C$_{12}$H$_{17}$NaP 215.0960. Found: 215.0953. The enantiomeric excess of the cyclohexylphenylphosphine borane (V-i) was determined by HPLC analysis on a Chiralcel OJ column, eluent: hexane/isopropylic alcohol 99:1, 1 mL/min, λ=210 nm: (R), $t_R$=12.54 min; (S)-enantiomer, $t_R$=13.54 min.

A.2.5. (S)-(–)-Phenyl-o-tolylphosphine borane (V-j)

Yield=83%, (94% ee); white oil; $R_f$=0.58 (petroleum ether/toluene 1:1); IR (ν cm$^{-1}$) 3444, 3058-2854 (C—H), 2391-2345 (B—H), 2252, 1635-1592, 1474, 1454, 1438, 1384, 1285, 1138, 1112, 1060, 1028, 907, 806, 751, 714, 698, 587, 549, 510, 472, 440; $^1$H NMR (CDCl$_3$): δ (ppm) 0.50-1.50 (m, 3H), 2.29 (s, 3H), 6.35 (dq, J=379 Hz, J=6.9 Hz, 1H), 7.18-7.24 (m, 2H), 7.34-7.37 (m, 3H), 7.40-7.43 (m, 1H), 7.50-7.54 (m, 2H), 7.60 (ddd, J=13.8 Hz, J=7.6 Hz, J=0.95 Hz, 1H); $^{13}$C NMR (CDCl$_3$): δ (ppm) 21.4 (d, J=5.4 Hz), 125.2 (d, J=55.8 Hz), 126.3 (d, J=56.1 Hz), 126.9 (d, J=11.8 Hz), 129.4 (d, J=10.2 Hz), 131.4 (d, J=7.7 Hz), 131.8 (d, J=2.8 Hz), 132.3 (d, J=2.6 Hz), 133.1 (d, J=9.3 Hz), 134.7 (d, J=13.8 Hz), 142.1 (d, J=5.3 Hz); $^{31}$P NMR (CDCl$_3$): δ (ppm) –5.4; MS (EI) m/z (relative intensity) 237 (M+Na$^+$, 100), 223 (M-BH$_3$+Na$^+$, 40), 206 (9); HRMS (ESI) calcd for C$_{13}$H$_{16}$BNaP: 237.09749. Found: 237.09772. The enantiomeric excess of the phenyl-o-tolylphoshine borane (V-j) was determined by HPLC analysis on a Chiralcel OD-H column, eluent: hexane/isopropyl alcohol 98:2, 1 mL/min, λ=254 nm: (R), $t_R$=8.29 min; (S)-enantiomer, $t_R$=8.71 min.

B. Synthesis of (S)-(2-Bromophenyl)-(2-Methoxyphenyl)-Phenylphosphine (II-n) In a One Pot Procedure Synthesis of (VII). 11.0 mL (3.30 mmol) of a freshly titrated toluene solution of dry HCl was added to 0.33 g (0.83 mmol) of (Rp)-N-methyl-[(1R,2S)(2-hydroxy-1-phenyl)ethyl]-amino-o-anisylphenylphosphine borane (VIII) and the reaction was stirred at room temperature during one hour. The ephedrine hydrochloride was filtered off using a Millipore 4 µm filter.

Step (i). The resulting solution of o-anisylchlorophenylphosphine borane (VII) was collected, degassed by four vacuum/argon cycles and cooled to –80° C. 1.20 mL (2.00 mmol) of t-BuLi (1.6 M in pentane) was then added dropwise under argon and the reaction mixture was stirred 5 minutes at –80° C. 2 mL of dry THF was slowly added followed by 0.14 mL (1.16 mmol) of 1,2-dibromobenzene (VI) and the resulting solution was stirred during one hour at –78° C. 5 mL of water was then added and the aqueous phase was extracted with dichloromethane (3×10 mL). The combined organic phases were dried over MgSO$_4$, filtered and the solvent evaporated giving a residue (IV-i) which was diluted with 3 mL of dry toluene under argon atmosphere.

Step (ii-a). 0.28 g (2.49 mmol) of DABCO was added and the resulting solution was stirred at room temperature during 2 hours. The solvent was evaporated under vacuum and the crude product (II-i) was purified by column chromatography on silica gel using petroleum ether/ethyl acetate 3:1 as eluent. Analytical pure sample can be obtained by recrystallization in methylene chloride/methyl alcohol. Colorless solid; Overall yield 51% (0.22 g); Enantiomeric excess: 99% by HPLC analysis (chiralpak AD, 0.2 mL·min$^{-1}$, hexane/2-propanol 99:1, $t_R$ (R)=30.8 min, $t_R$ (S)=35.0 min); $R_f$ 0.41 (petroleum ether/ethyl acetate 3:1); mp 128-130° C.; $[α]_D$+20.6 (c 0.5, CHCl3); IR (neat) 3063, 2930, 2833, 1581, 1571, 1553, 1458, 1428, 1298, 1271, 1239, 1162, 1128, 1093, 1069, 1041, 1017, 864, 793, 752 cm$^{-1}$; $^1$H NMR (300 MHz, CDCl$_3$) δ 3.77 (s, 3H), 6.78-6.82 (m, 1H), 6.65-6.70 (m, 1H), 6.87-6.96 (m, 2H), 7.18-7.24 (m, 2H), 7.28-7.43 (m, 6H), 7.58-7.63 (m, 1H); $^{13}$C NMR (75.5 MHz, CDCl$^3$) δ 55.7, 110.3 (d, J=1.5 Hz), 121.2, 124.5 (d, J=12.4 Hz), 127.3, 128.5 (d, J=7.4 Hz), 129.0, 130.0, 130.1 (d, J=32.0 Hz), 130.6, 132.8 (d, J=2.4 Hz), 133.9, 134.1, 134.4, 135.4 (d, J=10.5 Hz), 138.5 (d, J=11.4 Hz), 161.3 (d, J=15.8 Hz); $^{31}$P NMR (121 MHz, CDCl$_3$) δ–15.3 (s); HRMS calcd for C$_{19}$H$_{16}$PBrONa [M+Na]$^+$ 393.0014. found 393.0006; Anal calcd for C$_{19}$H$_{16}$PBrO: C, 61.48; H, 4.34. found: C, 61.37; H, 4.59.

C Synthesis of α-Halogenophenyl Phosphines Boranes (IV) Starting from Secondary Phosphine Boranes (V)

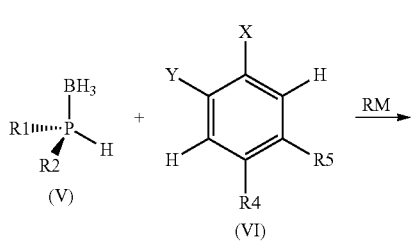

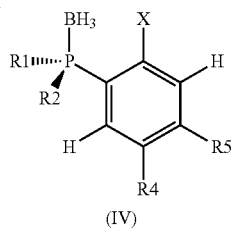

(IV)

TABLE 1

| Synthesis of compounds (IV) (X = Y and R⁴ = R⁵) | | | | | | | | |
|---|---|---|---|---|---|---|---|---|
| R¹R²P(BH₃)H (V) | | | ArXY (VI) | | | R¹R²P(BH₃)o-XAr (IV) | | |
| | R¹ | R² | | X, Y | R⁴, R⁵ | | Rdt (%) | ee (%) |
| (V-a) | Ph | Ph | (VI-a) | Br | H | (IV-a) | 75 | — |
| (V-b) | c-Hex | c-Hex | (VI-a) | Br | H | (IV-b) | 63 | — |
| (V-c) | Me | Me | (VI-a) | Br | H | (IV-c) | 42 | — |
| (V-d) | i-Pr | i-Pr | (VI-a) | Br | H | (IV-d) | 55 | — |
| (V-e) | o-Tol | o-Tol | (VI-a) | Br | H | (IV-e) | 40ᵃ | — |
| (V-a) | Ph | Ph | (VI-b) | Br | Me | (IV-f) | 56 | — |
| (V-a) | Ph | Ph | (VI-c) | I | H | (IV-g) | 50 | — |
| (V-b) | c-Hex | c-Hex | (VI-c) | I | H | (IV-h) | 56 | — |
| (S)-(V-f)ᵇ | o-An | Ph | (VI-a) | Br | H | (R)-(IV-i) | 53 | 95 |
| (R)-(V-f)ᶜ | Ph | o-An | (VI-a) | Br | H | (S)-(IV-i) | " | " |
| (S)-(V-f)ᵇ | o-An | Ph | (VI-c) | I | H | (R)-(IV-j) | 42ᵃ | 95 |
| (S)-(V-g)ᵇ | Fc | Ph | (VI-a) | Br | H | (R)-(IV-k) | 47 | 99 |
| (R)-(V-g)ᶜ | Ph | Fc | (VI-a) | Br | H | (S)-(IV-k) | 50 | 99 |
| (S)-(V-g)ᵇ | Fc | Ph | (VI-c) | I | H | (R)-(IV-l) | 55 | 99 |
| (R)-(V-h)ᵇ | i-Pr | Ph | (VI-a) | Br | H | (S)-(IV-m) | 48 | 95 |
| (S)-(V-h) | Ph | i-Pr | (VI-a) | Br | H | (R)-(IV-m) | " | " |
| (R)-(V-i)ᵇ | c-Hex | Ph | (VI-a) | Br | H | (S)-(IV-n) | 47 | 95 |
| (S)-(V-i)ᶜ | Ph | c-Hex | (VI-a) | Br | H | (R)-(IV-n) | 63 | 95 |
| (R)-(V-j)ᶜ | Ph | o-Tol | (VI-a) | Br | H | (S)-(IV-o) | 66ᵃ | 73 |

ᵃisolated after decomplexation.
ᵇprepared starting from (−)-ephedrine.
ᶜprepared starting from (+)-ephedrine C1. Synthesis of Ortho Bromoarylphosphine Boranes (IV: General procedure To a solution of secondary phosphine borane (V) (0.83 mmol) in dry THF (2 mL) was added dropwise n-BuLi (0.83 mmol) under argon at −78° C The resulting solution was stirred at this temperature during one hour and 1,2-dibromobenzene (VI-a) (1.16 mmol) was then added dropwise followed by n-BuLi (0.17 mmol). After one hour at −78° C., the reaction mixture was quenched with water (10 mL) and extracted with methylene chloride (3×10 mL). The organic phases were dried over MgSO₄, filtered and the solvent evaporated giving a residue which was purified by column chromatography on silica gel and/or by recristallisation.

C1.1. (2-Bromophenyl)-Diphenylphosphine Borane (IV-a)

From secondary phosphine borane (V-a); Purification: column chromatography (elution with 2:1 petroleum ether/ethyl acetate) and/or recristallisation in hexane/methylene chloride. White solid; Yield: 75%; $R_f$ 0.62 (petroleum ether/ethyl acetate 2:1); IR (neat) 3052, 2924, 2854, 2814, 2379, 2340, 1558, 1480, 1436, 1424, 1128, 1106, 1058, 1025, 998, 738, 690 cm⁻¹; ¹H NMR (300 MHz, CDCl₃) δ 7.20-7.31 (m, 3H, Harom), 7.36-7.49 (m, 6H, Harom), 7.57-7.64 (m, 5H, Harom); ¹³C NMR (75.5 MHz, CDCl₃) δ 127.3 (d, J=9.1 Hz, Carom), 128.0 (d, J=5.9 Hz, Carom), 128.1 (d, J=58.7 Hz, Carom), 128.8 (d, J=10.4 Hz, Carom), 130.1 (d, J=57.3 Hz, Carom), 131.3 (d, J=2.4 Hz, Carom), 132.7 (d, J=2.1 Hz, Carom), 133.3 (d, J=9.6 Hz, Carom), 135.1 (d, 5.9 Hz, Carom), 136.6 (d, J=10.1 Hz, Carom); ³¹P NMR (121 MHz, CDCl₃) δ 26.6; HRMS calcd for C₁₈H₁₇PBBrNa (M+Na)⁺ 379.0221. found 379.0197; Anal calcd for C₁₈H₁₇PBBr: C, 60.90; H, 4.83. found: C, 61.06; H, 5.13.

C1.2. (2-Bromophenyl)-dicyclohexylphosphine borane (IV-b)

From secondary phosphine borane (V-b); The same procedure as above was used except that after adding n-BuLi at −78° C., the resulting solution was stirred 30 minutes at this temperature then 30 minutes at room temperature.

Purification: column chromatography (elution with 3:1 petroleum ether/methylene chloride) and/or recristallisation in methyl alcohol/methylene chloride. White solid; Yield: 63%; $R_f$ 0.24 (petroleum ether/methylene chloride 3:1); IR (neat) 2930, 2851, 2379, 1446, 1418, 1274, 1061, 890, 854, 758, 736 cm⁻¹; ¹H NMR (300 MHz, CDCl₃) δ 1.16-1.37 (m, 1OH, cHex), 1.55-1.70 (m, 6H, cHex), 1.80-1.85 (m, 2H, cHex), 1.93-1.97 (m, 2H, cHex), 2.77-2.85 (m, 2H, cHex), 7.27-7.40 (m, 2H, Harom), 7.60 (dt, J=1.8, 7.7 Hz, Harom), 8.07 (ddd, J=1.7, 7.6, 12.6 Hz, Harom); ¹³C NMR (75.5 MHz, CDCl₃) δ 25.7 (d, J=1.3 Hz, CH₂), 26.8 (d, J=9.5 Hz, CH₂), 27.0 (d, J=8.5 Hz, CH₂), 27.8 (CH₂), 28.8 (CH₂), 32.9 (d, J=32.3 Hz, CH), 127.1 (d, J=3.1 Hz, Carom), 127.3 (d, J=10.9 Hz, Carom), 128.0 (d, J=46.3 Hz, Carom), 132.4 (d, J=2.1 Hz, Carom), 134.0 (d, J=4.4 Hz, Carom), 140.1 (d, J=15.0 Hz, Carom); ³¹P NMR (121 MHz, CDCl₃) δ 40.9; HRMS calcd for C₁₈H₂₉PBrBNa (M+Na)⁺ 389.1179. found 389.1157; Anal calcd for C₁₈H₂₉PBrB: C, 58.89; H, 7.96. found: C, 58.68; H, 8.29.

C1.3. (2-bromophenyl)-dimethylphosphine borane (IV-c)

The same procedure as above was used starting from secondary phosphine borane (V-c), except that after adding n-BuLi at −78° C., the resulting solution was stirred 30 minutes at this temperature then 30 minutes at room temperature.

Purification: column chromatography (elution with 3:1 petroleum ether/ethyl acetate). Colorless oil; Yield: 42%; $R_f$ 0.49 (petroleum ether/ethyl acetate 3:1); IR (neat) 3077, 2375, 2360, 2335, 1580, 1559, 1453, 1413, 1302, 1289, 1273, 1256, 1144, 1109, 1071, 1022, 946, 919, 755 cm⁻¹; H NMR (300 MHz, Acetone d$^6$) δ 1.55 (d, J=10.4 Hz, 6H, CH$_3$), 7.24-7.33 (m, 2H, Harom), 7.52-7.59 (m, 1H, Harom), 7.70-7.77 (m, 1H, Harom); $^{13}$C NMR (75.5 MHz, Acetone d$^6$) δ 12.0 (d, J=40.1 Hz, CH$_3$), 127.5 (Carom), 128.6 (d, J=10.9 Hz, Carom), 131.8 (d, J=50.6 Hz, Carom), 134.2 (d, J=2.2 Hz, Carom), 135.4 (d, J=4.7 Hz, Carom), 137.0 (d, J=15.7 Hz, Carom); $^{31}$P NMR (121 MHz, Acetone d$^6$) δ 11.1-12.5 (m); HRMS calcd for C$_8$H$_{13}$PBrBNa (M+Na)$^+$ 252.9925. found 252.9923; Anal calcd for C$_8$H$_{13}$PBrB: C, 41.62; H, 5.68. found: C, 41.29; H, 6.07.

C1.4. (2-bromophenyl)-diisopropylphosphine borane (IV-d)

The same procedure as above was used starting from secondary phosphine borane (V-d), except that after adding n-BuLi at −78° C, the resulting solution was stirred 30 minutes at this temperature then 30 minutes at room temperature.

Purification: column chromatography (elution with 3:1 petroleum ether/methylene chloride). White solid; Yield: 55%; R$_f$ 0.26 (petroleum ether/methylene chloride 3:1); IR (neat) 2974, 2932, 2871, 2393, 2373, 2349, 1574, 1557, 1453, 1422, 1389, 1370, 1261, 1110, 1071, 1046, 1021, 931 cm$^{-1}$; $^1$H NMR (300 MHz, CDCl$_3$) δ 0.86 (dd, J=7.1, 15.9 Hz, 6H, CH$_3$), 1.27 (dd, J=7.0, 15.8 Hz, 6H, CH$_3$), 2.95-3.09 (m, 2H, CH), 7.22-7.35 (m, 2H, Harom), 7.55 (tt, J=1.8, 7.7 Hz, 1H, Harom), 8.04 (ddd, J=1.5, 7.5, 12.6 Hz, 1H, Harom); $^{13}$C NMR (75.5 MHz, CDCl$_3$) δ 18.5 (d, J=2.8 Hz, CH$_3$), 18.7 (CH$_3$), 22.8 (d, J=33.1 Hz, CH) 126.7 (d, J=3.1 Hz, Carom), 127.3 (d, J=10.9 Hz, Carom), 128.7 (d, J=46.6 Hz, Carom), 132.6 (d, J=2.2 Hz, Carom), 134.2 (d, J=4.4 Hz, Carom), 139.8 (d, J=14.8 Hz, Carom); $^{31}$P NMR (121 MHz, CDCl$_3$) δ 48.4-49.9 (m); HRMS calcd for C$_{12}$H$_{21}$PBrBNa (M+Na)$^+$ 309.0552. found 309.0545; Anal calcd for C$_{12}$H$_{21}$PBrB: C, 50.22; H, 7.38. found: C, 50.57; H, 7.53.

C.1.5. (2-bromophenyl)-di(o-tolyl)phosphine borane (IV-e) and free phosphine (II-e)

To a solution of di-(o-tolyl)phosphine borane 37e (0.19 g, 0.83 mmol) in dry THF (2 mL) was added dropwise under argon at −78° C. n-BuLi (0.83 mmol). The resulting solution was stirred at this temperature during one hour and 1,2-dibromobenzene (VI-a) (0.15 mL, 1.16 mmol) was then added dropwise followed by n-BuLi (0.17 mmol). After one hour at −78° C., the reaction mixture was quenched with water (10 mL) and extracted with methylene chloride (3×10 mL). The organic phases were dried over MgSO$_4$, filtered and the solvent evaporated giving the crude (IV-e) which was diluted with dry toluol (5 mL) under argon atmosphere. DABCO (0.28 g, 2.49 mmol) was added and the resulting solution was stirred at room temperature overnight. The solvent was evaporated under vacuo and the crude decomplexed product (II-e) was purified by column chromatography on silica gel using petroleum ether/ethyl acetate 3:1 as eluent. White solid; yield 40%; R$_f$ 0.59 (petroleum ether/ethyl acetate 3:1); IR (neat) 3055, 3002, 2973, 1588, 1554, 1466, 1445, 1422, 1377, 1271, 1250, 1201, 1161, 1130, 1099, 1017, 867, 746, 715 cm$^{-1}$; $^1$H NMR (300 MHz, CDCl$_3$) δ 2.46 (2s, 6H, CH$_3$), 6.76-6.78 (m, 3H, Harom), 7.12-7.14 (m, 2H, Harom), 7.22-7.24 (m, 2H, Harom), 7.27-7.29 (m, 2H, Harom), 7.32 (td, J=1.3, 7.4 Hz, 2H, Harom), 7.64-7.66 (m, 1H, Harom); $^{13}$C NMR (75.5 MHz, CDCl$_3$) δ 21.1 (CH$_3$), 21.3 (CH$_3$), 126.3 (Carom), 127.6 (Carom), 129.0 (Carom), 130.1 (Carom), 130.2 (d, J=4.6 Hz, Carom), 130.6 (d, J=32.5 Hz, Carom), 133.1 (d, J=2.9 Hz, Carom), 133.2 (Carom), 134.0 (d, J=11.4 Hz, Carom), 134.7 (Carom), 137.7 (d, J=10.8 Hz, Carom), 142.8 (d, J=27.4 Hz, Carom); $^{31}$P NMR (121 MHz, CDCl$_3$) δ −19.7; HRMS calcd for C$_{20}$H$_{18}$PBrNa (M+Na)$^+$ 391.0222. found 391.0203; Anal calcd for C$_{20}$H$_{18}$PBr: C, 65.06; H, 4.91. found: C, 65.14; H, 5.00.

C.1.6. (2-bromo-4,5-dimethylphenyl)-diphenylphosphine borane (IV-f)

To a solution of diphenylphosphine borane (V-a) (0.17 g, 0.83 mmol) in dry THF (2 mL) was added dropwise under argon at −78° C. n-BuLi (0.83 mmol). The resulting solution was stirred at this temperature during one hour and 4,5-dibromo-o-xylene (VI-b) (0.31 g, 1.16 mmol) was then added dropwise followed by n-BuLi (0.17 mmol). After one hour at −78° C., the reaction mixture was quenched with water (10 mL) and extracted with methylene chloride (3×10 mL). The organic phases were dried over MgSO$_4$, filtered and the solvent evaporated giving a residue which was purified by column chromatography on silica gel using petroleum ether/methylene chloride 3:1 as eluent. Analytical pure sample can be obtained by recristallisation in methylene chloride/hexane. White solid; yield 56%; R$_f$ 0.45 (petroleum ether/ethyl acetate 3:1); IR (neat) 3050, 2986, 2946, 2917, 2417, 2388, 2357, 1588, 1481, 1471, 1436, 1343, 1136, 1125, 1102, 1062, 1028, 999, 923, 877, 749, 734, 701, 692 cm$^{-1}$; $^1$H NMR (300 MHz, CDCl$_3$) δ 2.17 (s, 3H, CH$_3$), 2.29 (s, 3H, CH$_3$), 7.21 (d, J=12.3 Hz, Harom), 7.43-7.56 (m, 7H, Harom), 7.65-7.72 (m, 4H, Harom); $^{13}$C NMR (75.5 MHz, CDCl$_3$) δ 19.4 (CH$_3$), 19.5 (CH$_3$), 124.7 (d, J=4.4 Hz, Carom), 131.1 (d, J=2.5 Hz, Carom), 133.2 (d, J=9.6 Hz, Carom), 135.9 (d, J=6.1 Hz, Carom), 136.3 (d, J=9.9 Hz, Carom), 137.8 (d, J=11.8 Hz, Carom), 142.6 (d, J=2.2 Hz, Carom); $^{31}$P NMR (121 MHz, CDCl$_3$) δ 25.5; HRMS calcd for C$_{20}$H$_{21}$PBBrNa (M+Na)$^+$ 405.0553. found 405.0563; Anal calcd for C$_{20}$H$_{21}$PBBr: C, 62.71; H, 5.53. found: C, 62.86; H, 5.58.

C.1.7. (R)-(2-bromophenyl)-(2-methoxyphenyl)-phenylphosphine borane (IV-i)

Starting from secondary phosphine borane (S)-(V-f); Purification: column chromatography (elution with 3:1 petroleum ether/ethyl acetate). White solid; Yield: 53%; Enantiomeric excess: 95% by HPLC analysis (chiralpak AD, 0.2 mL·min$^{-1}$, hexane-2-propanol 99:1, t$_R$ (R)=29.4 min, t$_R$ (S)=32.2 min; R$_f$ 0.18 (petroleum ether/ethyl acetate 3:1); [α]$_D$=−1.3 (c 1.6, CHCl$_3$); IR (neat) 3054, 2940, 2838, 2384, 1589, 1575, 1559, 1478, 1454, 1431, 1277, 1265, 1252, 1164, 1134, 1103, 1059, 1021, 854, 802, 733 cm; $^1$H NMR (300 MHz, CDCl$_3$) δ 3.56 (s, 3H, OCH$_3$), 6.94 (dd, J=3.8, 8.3 Hz, 1H, Harom), 7.08 (tdd, J=0.8, 2.1, 7.5 Hz, 1H, Harom), 7.28-7.33 (m, 3H, Harom), 7.44-7.54 (m, 4H, Harom), 7.60-7.64 (m, 1H, Harom), 7.80-7.87 (m, 3H, Harom); $^{13}$C NMR (75.5 MHz, CDCl$_3$) δ 55.4 (OCH$_3$), 111.5 (d, J=4.6 Hz, Carom), 116.5 (d, J=57.8 Hz, Carom), 121.5 (d, J=12.2 Hz, Carom), 126.7 (d, J=6.4 Hz, Carom), 127.0 (d, J=9.2 Hz, Carom), 128.3 (d, J=59.9 Hz, Carom), 128.4 (d, J=10.5 Hz, Carom), 131.0 (d, J=61.4 Hz, Carom), 131.1, (d, J=2.4 Hz, Carom), 131.7 (d, J=2.1 Hz, Carom), 133.8 (d, J=1.9 Hz, Carom), 133.9 (d, J=9.8 Hz, Carom), 134.5, (d, J=6.0 Hz, Carom), 135.0 (d, J=9.8 Hz, Carom), 135.6 (d, J=9.8 Hz, Carom), 161.2 (Carom); $^{31}$P NMR (121 MHz, CDCl$_3$) δ 23.7; HRMS calcd for C$_{19}$H$_{19}$PBrBONa (M+Na)$^+$ 407.0346. found 407.0333; Anal calcd for C$_{19}$H$_{19}$BBrOP: C, 59.27; H, 4.97. found: C, 58.79; H, 5.25.

C.1.8. (R)-Ferrocenyl-(2-bromophenyl)-phenylphosphine borane (IV-k)

Starting from secondary phosphine borane (S)-(V-g); Purification: recristallisation in hexane/methylene chloride. Orange solid; Yield: 47%; Enantiomeric excess: 99% by HPLC analysis (chiralcel OD-H, 0.5 mL·min$^{-1}$, hexane-2-propanol 98:2, t$_R$ (R)=19.6 min, t$_R$ (S)=23.2 min; R$_f$ 0.39

(petroleum ether/ethyl acetate 3:1); $[\alpha]_D$=+162.9 (c 0.5, CHCl$_3$); IR (neat) 3092, 3074, 3054, 2408, 2382, 2350, 1571, 1555, 1483, 1450, 1437, 1417, 1387, 1334, 1308, 1271, 1249, 1169, 1130, 1105, 1060, 1053, 1022, 998, 844, 765, 753, 739, 721 cm$^{-1}$; $^1$H NMR (300 MHz, CDCl$_3$) δ 4.09 (sl, 5H, Cp), 4.14-4.16 (m, 1H, Cp), 4.51-4.53 (m, 1H, Cp), 4.61-4.62 (m, 1H, Cp), 4.84-4.87 (m, 1H, Cp), 7.22-7.31 (m, 3H, Harom), 7.48-7.59 (m, 4H, Harom), 7.73-7.80 (m, 2H, Harom); $^{13}$C NMR (75.5 MHz, CDCl$_3$) δ 69.2 (d, J=70.1 Hz, Cp), 69.9 (Cp), 72.0 (Cp), 72.1 (d, J=5.0 Hz, Cp), 72.2 (d, J=6.7 Hz, Cp), 74.7 (d, J=14.5 Hz, Cp), 126.9 (d, J=8.6 Hz, Carom), 127.0 (d, J=7.2 Hz, Carom), 128.5 (d, J=10.5 Hz, Carom), 129.7 (d, J=61.4 Hz, Carom), 131.1 (d, J=2.4 Hz, Carom), 132.1 (d, J=2.0 Hz, Carom), 132.6 (d, J=9.8 Hz, Carom), 132.9 (d, J=58.1 Hz, Carom), 134.7 (d, J=5.7 Hz, Carom), 135.6 (d, J=8.8 Hz, Carom); $^{31}$P NMR (121 MHz, CDCl$_3$) δ 23.3; HRMS calcd for C$_{22}$H$_{21}$PBrBFeNa (M+Na)$^+$ 484.9905. found 484.9912; Anal calcd for C$_{22}$H$_{21}$PBrBFe: C, 57.08; H, 4.57. found: C, 56.78; H, 4.61.

C.1.9. (S)-(2-bromophenyl)-phenylisopropylphosphine borane (IV-m)

Starting from secondary phosphine borane (R)-(V-h); Purification: column chromatography (elution with 3:1 petroleum ether/ethyl acetate). Colorless oil; Yield: 48%; Enantiomeric excess: 95% by HPLC analysis (lux 5µ-cellulose 2, 0.2 mL·min$^{-1}$, hexane-2-propanol 98:2, $t_R$ (S)=35.2 min, $t_R$ (S)=37.7 min; R$_f$ 0.52 (petroleum ether/ethyl acetate 3:1); $[\alpha]_D$=−45.0 (c 0.3, CHCl$_3$); IR (neat) 2971, 2932, 2872, 2381, 1576, 1453, 1436, 1417, 1271, 1254, 1108, 1065, 1039, 1024, 739, 696 cm$^{-1}$; $^1$H NMR (300 MHz, CDCl$_3$) δ 1.02 (dd, J=7.1, 17.1 Hz, 3H, CH$_3$), 1.32 (dd, J=7.0, 16.4 Hz, 3H, CH$_3$), 3.31-3.45 (m, 1H, CH), 7.23-7.40 (m, 5H, Harom), 7.48 (ddd, J=1.3, 2.5, 7.9 Hz, 1H, Harom), 7.55-7.61 (m, 2H, Harom), 8.08 (ddd, J=1.6, 7.7, 12.5 Hz, 1H, Harom); $^{13}$C NMR (75.5 MHz, CDCl$_3$) δ 17.3 (d, J=2.3 Hz, CH$_3$), 18.0 (d, J=2.1 Hz, CH$_3$), 21.3 (d, J=35.7 Hz, CH), 127.4 (d, J=10.8 Hz, Carom), 127.7 (Carom), 128.3 (d, J=55.2 Hz, Carom), 128.4 (Carom), 128.5 (Carom), 129.6 (d, J=50.6 Hz, Carom), 130.6 (d, J=2.3 Hz, Carom), 132.4 (Carom), 132.6 (Carom), 132.8 (d, J=2.2 Hz, Carom), 134.6 (d, J=4.8 Hz, Carom), 138.1 (d, J=14.6 Hz, Carom); $^{31}$P NMR (121 MHz, CDCl$_3$) δ 35.0-35.6 (m); HRMS calcd for C$_{15}$H$_{19}$PBBrNa (M+Na)$^+$ 343.0396. found 343.0407; Anal calcd for C$_{15}$H$_{19}$PBBr: C, 56.12; H, 5.97. found: C, 56.50; H, 6.16.

C.1.10. (S)-(2-bromophenyl)-cyclohexylphenylphosphine borane (IV-n)

Starting from secondary phosphine borane (R)-(V-i); Purification: column chromatography (elution with 4:1 petroleum ether/ethyl acetate). White solid; Yield: 47%; Enantiomeric excess: 95% by HPLC analysis (chiralcel OD-H, 0.2 mL·min$^{-1}$, hexane-2-propanol 98:2, $t_R$ (S)=26.1 min, $t_R$ (S)=28.1 min; R$_f$ 0.46 (petroleum ether/ethyl acetate 4:1); $[\alpha]_D$=−21.6 (c 0.2, CHCl$_3$); IR (neat) 2936, 2853, 2385, 2348, 1577, 1559, 1489, 1453, 1439, 1421, 1133, 1110, 1057, 1021, 1003, 762, 737 cm$^{-1}$; $^1$H NMR (300 MHz, CDCl$_3$) δ 1.29-1.50 (m, 5H, CH$_2$), 1.74-1.83 (m, 3H, CH$_2$), 1.90-1.92 (m, 1H, CH$_2$), 2.03-2.05 (m, 1H, CH$_2$), 3.18-3.24 (m, 1H, CH), 7.35 (t, J=7.5 Hz, 1H, Harom), 7.41-7.48 (m, 4H, Harom), 7.58 (d, J=7.8 Hz, 1H, Harom), 7.65-7.68 (m, 2H, Harom), 8.17-8.20 (m, 1H, Harom); $^{13}$C NMR (75.5 MHz, CDCl$_3$) δ 25.8 (d, J=1.5 Hz, CH$_2$), 26.7 (CH$_2$), 26.8 (CH$_2$), 27.0 (d, J=12.6 Hz, CH$_2$), 28.1 (CH$_2$), 31.3 (d, J=34.7 Hz, CH), 127.4 (d, J=11.0 Hz, Carom), 128.0 (d, J=12.6 Hz, Carom), 128.4 (d, J=67.3 Hz, Carom), 128.5 (d, J=9.9 Hz, Carom), 129.1 (d, J=51.1 Hz, Carom), 130.6 (d, J=2.4 Hz, Carom), 132.4 (d, J=8.7 Hz, Carom), 132.8 (d, J=2.2 Hz, Carom), 134.5 (d, J=4.7 Hz, Carom), 138.3 (d, J=15.1 Hz, Carom); $^{31}$P NMR (121 MHz, CDCl$_3$) δ 31.3-31.6 (m); HRMS calcd for C$_{18}$H$_{23}$PBBrNa (M+Na)$^+$ 383.0071. found 383.0723; Anal calcd for C$_{18}$H$_{23}$PBBr: C, 59.88; H, 6.42. found: C, 66.10; H, 6.16.

C.2. Synthesis of ortho iodophenyl phosphine borane (IV-g, h, j, l):

General Procedure:

To a solution of secondary phosphine borane (V) (0.83 mmol) in dry THF (2 mL) was added dropwise under argon at −78° C. n-BuLi (0.83 mmol). The resulting solution was stirred at this temperature during one hour and 1,2-diiodobenzene (VI-c) (1.16 mmol) was then added dropwise followed by n-BuLi (0.17 mmol). After one hour at −78° C., the reaction mixture was quenched with water (10 mL) and extracted with methylene chloride (3×10 mL). The organic phases were dried over MgSO$_4$, filtered and the solvent evaporated giving a residue which was purified by column chromatography on silica gel and/or by recristallisation.

C.2.1. (2-iodophenyl)-diphenylphosphine borane (IV-g)

Starting from secondary phosphine borane (V-a); Purification: column chromatography (elution with 1:1 petroleum ether/methylene chloride) and/or recristallisation in ethyl acetate. White solid; Yield: 50%; R$_f$ 0.45 (petroleum ether/methylene chloride 1:1); IR (neat) 3051, 2401, 2342, 2245, 1570, 1555, 1480, 1436, 1420, 1311, 1255, 1188, 1165, 1126, 1101, 1054, 1028, 999, 972, 737, 688 cm; $^1$H NMR (300 MHz, CDCl$_3$) δ 7.13-7.19 (m, 1H, Harom), 7.20-7.27 (m, 1H, Harom), 7.33-7.40 (m, 1H, Harom), 7.46-7.60 (m, 6H, Harom), 7.68-7.75 (m, 4H, Harom), 8.03 (ddd, J=1.1, 3.2, 7.8 Hz, 1H, Harom); $^{13}$C NMR (75.5 MHz, CDCl$_3$) δ 101.2 (d, J=8.4 Hz, Carom), 127.9 (d, J=9.0 Hz, Carom), 128.1 (d, J=58.8 Hz, Carom), 128.9 (d, J=10.2 Hz, Carom), 131.3 (d, J=2.4 Hz, Carom), 132.3 (d, J=2.2 Hz, Carom), 133.3 (d, J=58.6 Hz, Carom), 133.6 (d, J=9.5 Hz, Carom), 136.5 (d, J=10.5 Hz, Carom), 142.7 (d, J=7.1 Hz, Carom); $^{31}$P NMR (121 MHz, CDCl$_3$) δ 30.5; HRMS calcd for C$_{18}$H$_{17}$PIBNa (M+Na)$^+$ 425.0101. found 425.0096; Anal calcd for C$_{18}$H$_{17}$PIB: C, 53.78; H, 4.26. found: C, 53.97; H, 4.36.

C.2.2. (2-iodophenyl)-dicyclohexylphosphine borane (IV-h)

The same procedure as above was used starting from secondary phosphine borane (V-b), except that after adding n-BuLi at −78° C., the resulting solution was stirred 10 minutes at this temperature then 20 minutes at room temperature.

Purification: column chromatography (elution with 2:1 petroleum ether/methylene chloride). White solid; Yield: 56%; R$_f$ 0.33 (petroleum ether/methylene chloride 2:1); IR (neat) 2919, 2851, 2397, 2352, 1573, 1556, 1447, 1414, 1345, 1064, 1040, 1004, 918, 887, 852, 818, 762, 734, 714, 639 cm; $^1$H NMR (300 MHz, CDCl$_3$) δ 1.00-1.17 (m, 10H, Hcy), 1.44-1.56 (m, 6H, Hcy), 1.63-1.67 (m, 2H, Hcy), 1.76-1.80 (m, 2H, Hcy), 2.73-2.85 (m, 2H, Hcy), 6.92 (tt, J=1.5, 7.5 Hz, 1H, Harom), 7.22 (tt, J=1.3, 7.5 Hz, 1H, Harom), 7.77 (dt, J=1.5, 7.9 Hz, 1H, Harom), 7.86 (ddd, J=0.9, 7.7, 12.9 Hz, 1H, Harom); $^{13}$C NMR (75.5 MHz, CDCl$_3$) δ 25.7 (d, J=1.2 Hz, CH$_2$), 26.9 (d, J=3.5 Hz, CH$_2$), 27.1 (d, J=2.7 Hz, CH$_2$), 27.8 (CH$_2$), 28.7 (d, J=1.2 Hz, CH$_2$), 32.5 (d, J=31.8 Hz, CH), 99.8 (d, J=2.3 Hz, Carom), 127.9 (d, J=11.2 Hz, Carom), 131.2 (d, J=47.2 Hz, Carom), 132.2 (d, J=2.2 Hz, Carom), 140.8 (d, J=16.0 Hz, Carom), 141.7 (d, J=5.2 Hz, Carom); $^{31}$P NMR (121 MHz, CDCl$_3$) δ 41.6; HRMS calcd for C$_{18}$H$_{29}$PIBNa (M+Na)$^+$ 437.1040. found 437.1012; Anal calcd for C$_{18}$H$_{29}$PIB: C, 52.21; H, 7.06. found: C, 52.19; H, 6.98.

C.2.3. (R)-(2-iodophenyl)-(2-methoxyphenyl)-phenylphosphine borane (IV-j) and free phosphine (II-j)

To a solution of secondary phosphine borane (S)-(V-f) (0.19 g, 0.83 mmol) in dry THF (2 mL) was added dropwise under argon at −78° C. n-BuLi (0.83 mmol). The resulting solution was stirred at this temperature during one hour and 1,2-diiodobenzene (VI-c (0.15 mL, 1.16 mmol) was then added dropwise followed by n-BuLi (0.17 mmol). After one hour at −78° C., the reaction mixture was quenched with water (10 mL) and extracted with methylene chloride (3×10 mL). The organic phases were dried over MgSO$_4$, filtered and the solvent evaporated giving the crude (IV-j), which was diluted with dry toluol (5 mL) under argon atmosphere. DABCO (0.28 g, 2.49 mmol) was added and the resulting solution was stirred at room temperature overnight. The solvent was evaporated under vacuo and the crude product (II-j) was purified by column chromatography on silica gel using petroleum ether/ethyl acetate 3:1 as eluent. White solid; Yield 42%; Enantiomeric excess: 95% by $^1$H NMR and/or $^{31}$P NMR of the corresponding phosphine oxide with (R)-3,5-dinitro-N-(1-phenyl-ethyl)-benzamide as chiral reagent; R$_f$ 0.45 (petroleum ether/ethyl acetate 3:1); [α]$_D$-24.2 (c 0.4, CHCl$_3$); IR (neat) 3050, 2933, 2835, 1584, 1573, 1554, 1472, 1462, 1431, 1300, 1274, 1241, 1183, 1163, 1130, 1094, 1071, 1043, 1024, 796, 753, 698 cm$^{-1}$; $^1$H NMR (300 MHz, CDCl$_3$) δ 3.67 (s, 3H, OCH$_3$), 6.56 (ddd, J=1.7, 4.4, 7.4 Hz, 1H, Harom), 6.72 (dt, J=1.9, 7.7 Hz, 1H, Harom), 6.77-6.86 (m, 2H, Harom), 6.92 (td, J=1.7, 7.6 Hz, 1H, Harom), 7.13-7.32 (m, 7H, Harom), 7.81 (ddd, J=1.1, 3.1, 7.8 Hz, 1H, Harom); $^{13}$C NMR (75.5 MHz, CDCl$_3$) δ 55.8 (OCH$_3$), 107.2 (d, J=41.4 Hz, Carom), 110.4 (d, J=1.5 Hz, Carom), 121.2 (Carom), 125.0 (d, J=12.7 Hz, Carom), 128.1 (Carom), 128.5 (Carom), 128.6 (Carom), 128.9 (Carom), 130.0 (Carom), 130.6 (Carom), 133.9 (Carom), 134.1 (Carom), 134.2 (Carom), 134.5 (Carom), 135.8 (d, J=10.9 Hz, Carom), 139.6 (d, J=3.8 Hz, Carom), 141.9 (d, J=9.0 Hz, Carom), 161.2 (d, J=15.6 Hz, Carom); $^{31}$P NMR (121 MHz, CDCl$_3$) δ 1.8; HRMS calcd for C$_{19}$H$_{16}$PIONa (M+Na)+ 440.9876. found 440.9891; Anal calcd for C$_{19}$H$_{16}$PIO: C, 54.57; H, 3.86. found: C, 54.55; H, 3.90.

C.2.4. (R)-Ferrocenyl-(2-iodophenyl)-phenylphosphine borane (IV-1)

Starting from secondary phosphine borane (S)-(V-g); Purification: Recristallisation in hexane/methylene chloride. Orange solid; Yield 55%; Enantiomeric excess: 99% by HPLC analysis (chiralcel OD-H, 0.5 mL·min$^{-1}$, hexane-2-propanol 98:2, t$_R$ (R)=19.2 min, t$_R$ (S)=25.2 min; R$_f$ 0.54 (petroleum ether/ethyl acetate 3:1); [α]$_D$ +207.1 (c 0.6, CHCl$_3$); IR (neat) 3124, 3086, 3052, 2407, 2380, 2350, 1553, 1483, 1426, 1387, 1368, 1335, 1100, 1059, 1027, 1010, 821, 739, 716, 693 cm$^{-1}$; $^1$H NMR (300 MHz, CDCl$_3$) δ 4.07-4.08 (m, 1H, Cp), 4.09 (sl, 5H, Cp), 4.51-4.52 (m, 1H, Cp), 4.62-4.63 (m, 1H, Cp), 7.07 (tt, J=1.6, 7.5 Hz, Harom), 7.14 (ddd, J=1.7, 7.8, 11.0 Hz, 1H, Harom), 7.28-7.33 (m, 2H, Harom), 7.50-7.63 (m, 3H, Harom), 7.77-7.83 (m, 2H, Harom), 7.91 (ddd, J=1.0, 3.1, 7.8 Hz, 1H, Harom); $^{13}$C NMR (75.5 MHz, CDCl$_3$) δ 69.8 (d, J=70.0 Hz, Cp), 70.0 (Cp), 71.7 (d, J=3.7 Hz, Cp), 72.1 (d, J=8.4 Hz, Cp), 72.3 (d, J=6.5 Hz, Cp), 74.9 (d, J=14.9 Hz, Cp), 100.2 (d, J=9.8 Hz, Carom), 127.6 (d, J=8.3 Hz, Carom), 128.6 (d, J=10.5 Hz, Carom), 129.2 (d, J=60.8 Hz, Carom), 131.3 (d, J=2.4 Hz, Carom), 131.7 (d, J=2.1 Hz, Carom), 133.4 (d, J=9.5 Hz, Carom), 135.4 (d, J=9.0 Hz, Carom), 136.0 (d, J=58.3 Hz, Carom), 142.2 (d, J=7.1 Hz, Carom); $^{31}$P NMR (121 MHz, CDCl$_3$) δ 27.5; HRMS calcd for C$_{22}$H$_{21}$PIBFeNa (M+Na)+ 532.9764. found 532.9747; Anal calcd for C$_{22}$H$_{21}$PIBFe: C, 51.82; H, 4.15. found: C, 52.03; H, 4.12.

C.3 Synthesis of (S)-o-anisylphenyl-o-tolylphosphine borane by direct alkylation in ortho position:

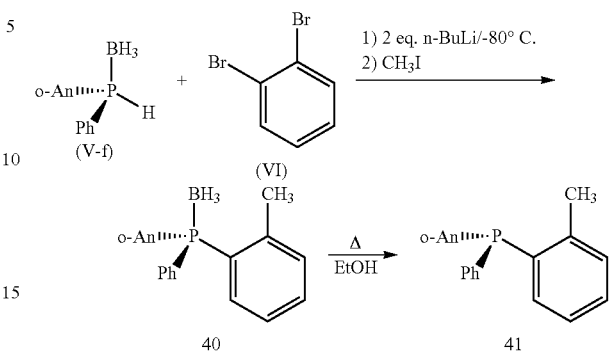

To a solution of secondary phosphine borane (V) (0.5 mmol) in dry THF (3 mL) was added dropwise n-BuLi (1.25 mmol; 2.5 equiv) under argon at −78° C. The resulting solution was stirred at this temperature during 5 min. and 1,2-dibromobenzene (0.75 mmol; 1.5 equiv) was then added dropwise. After 10 min. at −78° C., the reaction mixture was quenched with MeI (0.5 mL) and stirred for 10 min. After hydrolysis (1 mL), the solvent is removed under vacuum, and the residue extracted with methylene chloride (3×10 mL). The organic phases were dried over MgSO$_4$, filtered and the solvent evaporated giving the crude 40 which was purified by short filtration on silica gel.

$^1$H NMR (CDCl$_3$): δ(ppm) 0.80-2.0 (3H, m), 2.30 (3H, s), 3.57 (3H, s), 6.9-8.0 (13H, m); $^{31}$P NMR (121 MHz, CDCl$_3$) δ+18.6 (J$_{PB}$=56 Hz)

However, after work up, a mixture of free phosphine 41 and its borane complex 40 was obtained. This one was taken up in ethanol and stirred overnight to complete the decomplexation. Yield=92%;

(S)-(−)-o-Anisylphenyl-o-tolylphosphine 41

White crystals (EtOH); R$_f$=0.68 (toluene); $^1$H NMR (CDCl$_3$): δ(ppm) 2.33 (3H, s), 3.68 (3H, s), 6.53-6.58 (1H, m), 6.66-6.70 (1H, m), 6.74-6.85 (2H, m), 6.95-7.05 (1H, m), 7.08-7.30 (8H, m); $^{13}$C NMR (CDCl$_3$): δ(ppm) 21.2 (d, $^3$J$_{P-C}$=21.3), 55.7, 110.2 (d, J$_{P-C}$=1.7), 121.1, 124.7 (d, J$_{P-C}$=11.6, 125.9, 128.3-128.6, 129.9 (d, J$_{P-C}$=4.6), 130.3, 132.8, 133.7, 134.0, 134.3, 135.3-136.0, 142.3 (d, J$_{P-C}$=26.0), 161.3 (d, J$_{P-C}$=15.7); $^{31}$P NMR (CDCl$_3$): δ(ppm) −23.1.

The enantiomeric purity of 41 was determined by comparison with a racemic sample, by $^{31}$P NMR in the presence of (+)-di-μ-chlorobis{2-[1-(dimethylamino)ethyl]phenyl-C,N}dipalladium.

D. Decomplexation of Phosphine Boranes (IV) in Phosphines (II)

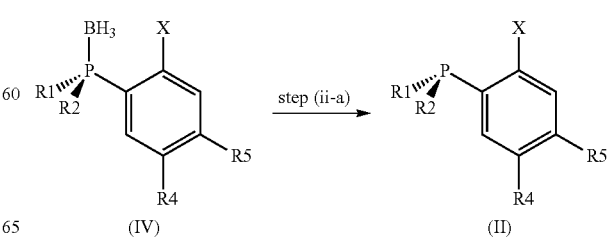

TABLE 2

Synthesis of free o-haloaryl phosphines (II)

| Phosphines borane (IV) | | | | | Phosphines (II) | Rdt (%) | ee (%) |
|---|---|---|---|---|---|---|---|
| | $R^1$ | $R^2$ | $R^4 = R^5$ | X | | | |
| (IV-a) | Ph | Ph | H | Br | (II-a) | 79 | — |
| (IV-e) | o-Tol | o-Tol | H | Br | (II-e) | 40[a] | — |
| (IV-f) | Ph | Ph | Me | Br | (II-f) | 84 | — |
| (IV-g) | Ph | Ph | H | I | (II-g) | 83 | — |
| (R)-(IV-i) | o-An | Ph | H | Br | (R)-(II-i) | 90 | 99 |
| (S)-(IV-i)[b] | Ph | o-An | H | Br | (S)-(II-i) | 55[a] | 99 |
| (R)-(IV-j) | o-An | Ph | H | I | (R)-(II-j) | 42[a] | 95 |
| (R)-(IV-k) | Fc | Ph | H | Br | (R)-(II-k) | 75 | 95 |
| (S)-(IV-m) | i-Pr | Ph | H | Br | (S)-(II-m) | 82 | 94 |
| (R)-(IV-n)[b] | Ph | c-Hex | H | Br | (R)-(II-n) | 80 | 86 |
| (S)-(IV-o)[b] | Ph | o-Tol | H | Br | (S)-(II-o) | 66[a] | 73 |

[a]global yield starting from the corresponding secondary phosphine borane (V).
[b]prepared starting from (+)-ephedrine Typical Procedure To a solution of o-bromophosphine borane (IV) (0.5 mmol) in toluene (3 mL) was added DABCO (1.5 mmol). The resulting solution was stirred under argon at room temperature overnight then the solvent was removed under vacuum. The crude (II) was purified by flash chromatography on silica gel and/or recrystallisation.

D.1. (R)-(2-bromophenyl)-(2-methoxyphenyl)-phenylphosphine (II-i)

Purification: column chromatography (elution with 3:1 petroleum ether/ethyl acetate) and recrystallisation in methylene chloride/methyl alcohol. White solid; yield 90%; Enantiomeric excess 99% by HPLC analysis (chiralpak AD, 0.2 mL·min$^{-1}$, hexane/2-propanol 99:1, $t_R$ (R) 30.8 min, $t_R$ (S) 35.0 min); $R_f$ 0.41 (petroleum ether/ethyl acetate 3:1); $[\alpha]_D$ −20.6 (c 0.5, CHCl$_3$); IR (neat) 3063, 2930, 2833, 1581, 1571, 1553, 1458, 1428, 1298, 1271, 1239, 1162, 1128, 1093, 1069, 1041, 1017, 864, 793, 752 cm$^{-1}$; $^1$H NMR (300 MHz, CDCl$_3$) δ 3.77 (s, 3H, OCH$_3$), 6.78-6.82 (m, 1H, Harom), 6.65-6.70 (m, 1H, Harom), 6.87-6.96 (m, 2H, Harom), 7.18-7.24 (m, 2H, Harom), 7.28-7.43 (m, 6H, Harom), 7.58-7.63 (m, 1H, Harom); $^{13}$C NMR (75.5 MHz, CDCl$_3$) δ 55.7 (OCH$_3$), 110.3 (d, J=1.5 Hz, Carom), 121.2 (Carom), 124.5 (d, J=12.4 Hz, Carom), 127.3 (Carom), 128.5 (d, J=7.4 Hz, Carom), 129.0 (Carom), 130.0 (Carom), 130.1 (d, J=32.0 Hz, Carom), 130.6 (Carom), 132.8 (d, J=2.4 Hz, Carom), 133.9 (Carom), 134.1 (Carom), 134.4 (Carom), 135.4 (d, J=10.5 Hz, Carom), 138.5 (d, J=11.4 Hz, Carom), 161.3 (d, J=15.8 Hz, Carom); $^{31}$P NMR (121 MHz, CDCl$_3$) δ −15.3 (s); HRMS calcd for C$_{19}$H$_{16}$PBrONa [M+Na]$^+$ 393.0014. found 393.0006; Anal calcd for C$_{19}$H$_{16}$PBrO: C, 61.48; H, 4.34. found: C, 61.37; H, 4.59.

D.2. (R)-(2-bromophenyl)-ferrocenyl-phenylphosphine (II-k)

Purification: column chromatography (elution with 3:1 petroleum ether/ethyl acetate). Orange solid; Yield 75%; Enantiomeric excess (after complexation with BH$_3$) 99% by HPLC analysis (chiralcel OD-H, 0.5 mL·min$^{-1}$, hexane/2-propanol 98:2, $t_R$ (R) 19.6 min, $t_R$ (S) 23.2 min); Rf 0.50 (petroleum ether/ethyl acetate 3:1); $[\alpha]_D^{20+207.1}$ (c 0.6; CHCl$_3$) IR (neat) 3104, 3045, 2926, 2855, 1741, 1552, 1481, 1446, 1436, 1420, 1308, 1270, 1248, 1192, 1163, 1108, 1098, 1016, 1003, 890, 821, 748, 698 cm$^{-1}$; $^1$H NMR (300 MHz, CDCl$_3$) δ 3.60-3.61 (m, 1H, Hfer), 3.98 (br.s, 5H, Hfer), 4.21-4.23 (m, 1H, Hfer), 4.29-4.31 (m, 1H, Hfer), 4.36-4.39 (m, 1H, Hfer), 6.84 (dt, J=2.1, 7.4 Hz, 1H, Harom), 7.06-7.19 (m, 2H, Harom), 7.28-7.32 (m, 3H, Harom), 7.34-7.42 (m, 3H, Harom); $^{13}$C NMR (75.5 MHz, CDCl$_3$) δ 69.9 (Cfer), 71.7 (Cfer), 72.3 (Cfer), 72.4 (d, J=7.1 Hz, Cfer), 75.3 (d, J=31.8 Hz, Cfer), 76.5 (d, J=7.6 Hz, Cfer), 128.1 (Carom), 129.0 (d, J=8.0 Hz, Carom), 129.4 (d, J=30.3 Hz, Carom), 129.9 (Carom), 130.9 (Carom), 133.6 (d, J=1.7 Hz, Carom), 134.8 (d, J=1.5 Hz, Carom), 135.2 (d, J=20.6 Hz, Carom), 137.3 (d, J=8.6 Hz, Carom), 142.6 (d, J=14.8 Hz, Carom); $^{31}$P NMR (121 MHz, CDCl$_3$) δ −16.6 (s); HRMS calcd for C$_{22}$H$_{18}$PBrFe [M]$^+$ 447.9675. found 447.9686; Anal calcd for C$_{22}$H$_{18}$PBrFe: C, 58.84; H, 4.04. found: C, 59.19; H, 4.05.

D.3. (S)-(2-bromophenyl)-isopropyl-phenylphosphine (11-m)

Purification: column chromatography (elution with 3:1 petroleum ether/ethyl acetate). Colorless oil; Yield 82%; Enantiomeric excess (after complexation with BH$_3$) 95% by HPLC analysis (lux 5μ Cellulose-2, 0.2 mL·min$^{-1}$, hexane/2-propanol 98:2, $t_R$ (S) 39.6 min, $t_R$ (R) 42.3 min); Rf 0.59 (petroleum ether/ethyl acetate 3:1); $[\alpha]_D^{20}$ −52.9 (c 0.4; CHCl$_3$) IR (neat) 3054, 2952, 2865, 1556, 1449, 1421, 1384, 1365, 1250, 1228, 1155, 1124, 1096, 1018, 878, 746, 697 cm$^{-1}$; $^1$H NMR (300 MHz, CDCl$_3$) δ 1.06 (dd, J=6.8, 15.5 Hz, 3H, CH$_3$), 1.20 (dd, J=6.9, 16.0 Hz, 3H, CH$_3$), 2.41-2.47 (m, 1H, CH), 7.19-7.22 (m, 1H, Harom), 7.32-7.35 (m, 3H, Harom), 7.37 (td, J=1.3, 7.6 Hz, 1H, Harom), 7.46-7.50 (m, 3H, Harom), 7.59 (ddd, J=1.2, 3.4, 8.0 Hz, 1H, Harom); $^{13}$C NMR (75.5 MHz, CDCl$_3$) δ 19.3 (d, J=19.6 Hz, CH$_3$), 19.8 (d, J=19.6 Hz, CH$_3$), 25.3 (d, J=9.1 Hz, CH), 127.3 (Carom), 128.3 (2s, Carom), 128.9 (Carom), 130.0 (Carom), 131.4 (d, J=30.2 Hz, Carom), 132.8 (Carom), 133.3 (d, J=2.6 Hz, Carom), 133.7 (Carom), 133.8 (Carom), 136.6 (d, J=13.0 Hz, Carom), 138.6 (d, J=14.8 Hz, Carom); $^{31}$P NMR (121 MHz, CDCl$_3$) δ −1.4 (s); HRMS calcd for C$_{15}$H$_{16}$PBrNa [M+Na]$^+$ 329.0065. found 329.0057.

E. Synthesis of o-Boronato Phosphine Derivatives (III-42) and (I-43)

E.1. Synthesis of o-boronato phosphine boranes (III-42)

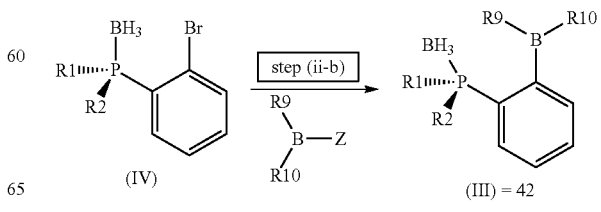

TABLE 3

Synthesis of o-boronatophenylphosphines borane (III-42)

| o-bromophosphines borane (IV) | | | Boron reagents | | Boronato products (III-42) | |
|---|---|---|---|---|---|---|
| | R¹ | R² | Z | R⁹=R¹⁰ | Rdt (%) | ee (%) |
| (IV-a) | Ph | Ph | i-PrO | (CH$_3$)$_2$C—O (cyclic) | 42a / 51 | — |
| (IV-B) | cHex | cHex | i-PrO | (CH$_3$)$_2$C—O (cyclic) | 42b / 66 | — |
| (R)-(IV-k) | Fc | Ph | i-PrO | (CH$_3$)$_2$C—O (cyclic) | (S)-42c / 43 | 99 |
| (IV-a) | Ph | Ph | Cl | cHex | 42d / 71 | — |
| (IV-b) | cHex | cHex | Cl | cHex | 42e / 55 | — |
| (R)-(IV-k) | Fc | Ph | Cl | cHex | (S)-42f / 60 | 99 |

E.1.1. [1,3,2]-dioxaborolan-2-yl derivatives
General Procedure

To a solution of o-bromophosphine borane (IV) (0.50 mmol) in dry THF (2 mL) was added dropwise under argon at −78° C. n-BuLi (0.55 mmol). The resulting solution was stirred at this temperature during one hour and 2-isopropoxy-4,4,5,5-tetramethyl-1,3,2-dioxaborolane (0.80 mmol) was then added dropwise. After 30 minutes at −78° C. and 20 hours at room temperature, the reaction mixture was quenched with water (10 mL) and extracted with methylene chloride (3×10 mL). The organic phases were dried over MgSO$_4$, filtered and the solvent evaporated giving a residue which was purified by column chromatography on silica gel and/or by recristallisation.

E.1.1.1. Diphenyl-[2-(4,4,5,5-tetramethyl-[1,3,2]dioxaborolan-2-yl)-phenyl]phosphine borane 42a Starting from the o-bromophenyl phosphine borane (IV-a); Purification: column chromatography (elution with 1:1 petroleum ether/methylene chloride). White solid; Yield: 51%; R$_f$ 0.28 (petroleum ether/methylene chloride 1:1); IR (neat) 2976, 2415, 2373, 2349, 1584, 1481, 1435, 1356, 1320, 1262, 1215, 1144, 1107, 1059, 964, 861, 733, 697, 667, 650 cm$^{-1}$; $^1$H NMR (300 MHz, CDCl$_3$) δ 0.95 (s, 12H, CH$_3$), 7.15-7.22 (m, 2H, Harom), 7.27-7.42 (m, 8H, Harom), 7.55-7.62 (m, 4H, Harom), 7.84 (ddd, J=1.4, 2.9, 7.2 Hz, 1H, Harom); $^{13}$C NMR (75.5 MHz, CDCl$_3$) δ 24.7 (CH$_3$), 83.9 (C(CH$_3$)$_2$), 128.3 (d, J=10.3 Hz, Carom), 129.9 (d, J=2.5 Hz, Carom), 130.1 (d, J=10.0 Hz, Carom), 130.6 (d, J=2.5 Hz, Carom), 130.7 (d, J=57.7 Hz, Carom), 133.5 (d, J=9.3 Hz, Carom), 134.4 (d, J=10.5 Hz, Carom), 134.5 (d, J=55.4 Hz, Carom), 136.7 (d, J=11.4 Hz, Carom); $^{31}$P NMR (121 MHz, CDCl$_3$) δ 25.0; HRMS calcd for C$_{24}$H$_{21}$PB$_2$O$_2$Na (M+Na)$^+$ 425.1991. found 425.1975; Anal calcd for C$_{24}$H$_{21}$PB$_2$O$_2$: C, 71.69; H, 7.27. found: C, 71.70; H, 7.06.

E.1.1.2. Dicyclohexyl-[2-(4,4,5,5-tetramethyl-[1,3,2]dioxaborolan-2-yl)-phenyl]phosphine borane 42b Starting from the o-bromophenylphosphine borane (IV-b); Purification: column chromatography (elution with 1:1 petroleum ether/methylene chloride) and/or recristallisation in methyl alcohol/methylene chloride. White solid; Yield: 66%; R$_f$ 0.45 (petroleum ether/methylene chloride 1:1); IR (neat) 2986, 2922, 2849, 2371, 2347, 1446, 1373, 1339, 1317, 1266, 1139, 1107, 1053, 960, 855, 823, 764, 749, 674 cm$^{-1}$; $^1$H NMR (300 MHz, CDCl$_3$) δ 0.94-0.99 (m, 10H, cHex), 1.20 (s, 12H, CH$_3$), 1.36-1.42 (m, 6H, cHex), 1.60-1.62 (m, 2H, cHex), 1.72-1.76 (m, 2H, cHex), 2.39-2.52 (m, 2H, cHex), 7.21-7.25 (m, 2H, Harom), 7.66-7.70 (m, 1H, Harom), 7.88 (ddd, J=1.7, 6.9, 13.3 Hz, 1H, Harom); $^{13}$C NMR (75.5 MHz, CDCl$_3$) δ 25.1 (CH$_3$), 25.8 (d, J=1.0 HZ, CH$_2$), 27.0 (d, J=8.3 Hz, CH$_2$), 27.2 (d, J=8.5 Hz, CH$_2$), 27.6 (CH$_2$), 28.6 (CH$_2$), 33.8 (d, J=32.9 Hz, CH), 84.4 (C(CH$_3$)$_2$), 129.6 (d, J=2.4 Hz, Harom), 130.4 (d, J=12.1 Hz, Harom), 133.1 (d, J=47.7 Hz, Harom), 136.7 (d, J=8.1 Hz, Harom), 137.4 (d, J=16.9 Hz, Harom); $^{31}$P NMR (121 MHz, CDCl$_3$) δ 34.0; HRMS calcd for C$_{24}$H$_{41}$PB$_2$O$_2$Na (M+Na)$^+$ 437.2931. found 437.2905; Anal calcd for C$_{24}$H$_{41}$PB$_2$O$_2$: C, 69.60; H, 9.98. found: C, 69.49; H, 10.06.

E.1.1.3. (S)-Ferrocenyl-phenyl-[2-(4,4,5,5-tetramethyl-[1,3,2]dioxaborolan-2-yl)-phenyl]phosphine borane 42c Starting from the o-bromophenyl phosphine borane (R)-(IV-k); Purification: column chromatography (elution with 2:1 petroleum ether/methylene chloride). Orange solid; Yield 43%; Enantiomeric excess: 99% by HPLC analysis (chiralcel OD-H, 0.2 mL·min$^{-1}$, hexane-2-propanol 98:2, t$_R$ (R)=27.2 min, t$_R$ (S)=29.7 min; R$_f$ 0.32 (petroleum ether/methylene chloride 2:1); [α]$_D$ +116.7 (c 0.3, CHCl$_3$); IR (neat) 2979, 2927, 2855, 2396, 1480, 1352, 1320, 1266, 1171, 1145, 1109, 1054, 1028, 860, 824, 740, 697 cm$^{-1}$; $^1$H NMR (300 MHz, CDCl$_3$) δ 0.93-0.1.03 (2s, 12H, CH$_3$), 3.91-3.92 (m, 1H, Cp), 4.06 (sl, 5H, Cp), 4.38-4.39 (m, 1H, Cp), 4.47-4.48 (m, 1H, Cp), 4.69-4.70 (m, 1H, Cp), 7.14-7.40 (m, 6H, Harom), 7.57-7.63 (m, 2H, Harom), 7.73-7.77 (m, 1H, Harom); $^{13}$C NMR (75.5 MHz, CDCl$_3$) δ 24.6-24.7 (2s, CH$_3$), 69.8 (Cp), 71.2 (d, J=68.6 Hz, Cp), 71.6 (d, J=4.0 Hz, Cp), 71.8 (d, J=5.7 Hz, Cp), 72.3 (d, J=4.6 Hz, Cp), 74.4 (d, J=13.6 Hz, Cp), 83.8 (C(CH$_3$)$_2$), 127.8 (d, J=10.4 Hz, Carom), 129.4 (d, J=2.4 Hz, Carom), 129.7 (d, J=9.4 Hz, Carom), 130.2 (d, J=2.4 Hz, Carom), 132.2 (d, J=60.6 Hz, Carom), 133.0 (d, J=9.6 Hz, Carom), 133.6 (d, J=9.2 Hz, Carom), 136.4 (d, J=11.3 Hz, Carom), 137.2 (d, J=54.9 Hz, Carom); $^{31}$P NMR (121 MHz, CDCl$_3$) δ 20.8; HRMS calcd for C$_{28}$H$_{33}$PB$_2$O$_2$FeNa (M+Na)$^+$ 533.1656. found 533.1654; Anal calcd for C$_{28}$H$_{33}$PB$_2$O$_2$Fe: C, 65.94; H, 6.52. found: C, 65.73; H, 6.45.

E.1.2. Dicyclohexylboranyl Derivatives
General Procedure

To a solution of o-bromophosphine borane (IV) (0.50 mmol) in dry THF (2 mL) was added dropwise under argon at −78° C. n-BuLi (0.55 mmol). The resulting solution was stirred at this temperature during one hour and chlorodicyclohexylboran 56b (IM solution in hexane) (0.80 mmol) was then added dropwise. After 30 minutes at −78° C. and 20 hours at room temperature, the reaction mixture was quenched with water (10 mL) and extracted with methylene chloride (3×10 mL). The organic phases were dried over MgSO$_4$, filtered and the solvent evaporated giving a residue which was purified by column chromatography on silica gel.

E.1.2.1. (2-dicyclohexylboranyl-phenyl)-diphenylphosphine borane 42d

Starting from the o-bromophenylphosphine borane (IV-a). Purification: column chromatography (elution with 3:1 petroleum ether/ethyl acetate). White solid; Yield: 71%; R$_f$ 0.57 (petroleum ether/ethyl acetate 3:1); IR (neat) 2914, 2842, 2779, 2494, 2449, 2158, 1437, 1106, 688 cm$^{-1}$; $^1$H NMR (300 MHz, CDCl$_3$) δ 0.78-0.95 (m, 2H, Hcy), 1.05-1.09 (m, 10H, Hcy), 1.50-1.69 (m, 10H, Hcy), 7.14-7.26 (m, 2H, Harom), 7.29-7.32 (m, 1H, Harom), 7.43-7.57 (m, 11H, Harom); $^{13}$C NMR (75.5 MHz, CDCl$_3$) δ 27.4 (CH$_2$), 28.4 (CH$_2$), 28.7 (CH$_2$), 31.0 (CH$_2$), 31.9 (CH$_2$), 33.5 (CH), 125.5 (d, J=8.7 Hz, Carom), 127.8 (Carom), 128.4 (d, J=62.8 Hz, Carom), 128.7 (d, J=10.6 Hz, Carom), 130.3 (d, J=2.9 Hz, Carom), 130.5 (d, J=8.5 Hz, Carom), 131.3 (d, J=2.6 Hz, Carom), 132.8 (d, J=5.8 Hz, Carom), 133.3 (d, J=9.6 Hz, Carom); $^{31}$P NMR (121 MHz, CDCl$_3$) δ 13.6; HRMS calcd for C$_{30}$H$_{39}$PB$_2$Na (M+Na)$^+$ 475.2878. found 475.2869; Anal calcd for C$_{30}$H$_{39}$PB$_2$: C, 79.68; H, 8.69. found: C, 79.80; H, 8.99.

E.1.2.2 Dicyclohexyl-(2-dicyclohexylboranyl-phenyl)phosphine borane 42e

Starting from the o-bromophenyl-dicyclohexylphosphine borane (IV-b). Purification: column chromatography (elution with 3:1 petroleum ether/methylene chloride). White solid; Yield 55%; R$_f$ 0.63 (petroleum ether/methylene chloride 3:1); IR (neat) 2918, 2845, 2455, 2412, 2148, 1442, 1272, 1169, 1128, 1082, 1004, 889, 852, 755 cm$^{-1}$; $^1$H NMR (300 MHz, CDCl$_3$) δ 0.88-1.08 (m, 4H, Hcy), 1.15-1.50 (m, 20H, Hcy), 1.65-1.85 (m, 16H, Hcy), 1.98-2.15 (m, 4H, Hcy), 7.20-7.27 (m, 2H, Harom), 7.31-7.41 (m, 2H, Harom); $^{13}$C NMR (75.5 MHz, CDCl$_3$) δ 25.8 (CH$_2$), 26.7 (CH$_2$), 26.9-27.0 (m, CH$_2$), 27.5 (m, CH$_2$), 28.8 (d, J=25.3 Hz, CH$_2$), 31.7 (d, J=16.8 Hz, CH$_2$), 33.0 (d, J=36.0 Hz, CH), 34.0 (CH), 124.8 (d, J=8.0 Hz, Harom), 126.5 (d, J=60.8 Hz, Harom), 129.7 (d, J=2.8 Hz, Harom), 130.4 (d, J=4.8 Hz, Harom), 130.7 (d, J=14.7 Hz, Harom); $^{31}$P NMR (121 MHz, CDCl$_3$) δ 18.0; HRMS calcd for C$_{30}$H$_{51}$PB$_2$Na (M+Na)$^+$ 487.3817. found 487.3789; Anal calcd for C$_{30}$H$_{51}$PB$_2$: C, 77.60; H, 11.07. found: C, 77.41; H, 11.20.

E.1.2.3. (S)-Ferrocenyl-(2-dicyclohexylboranyl-phenyl) phosphine borane 42f

Starting from the ferrocenyl-(o-bromophenyl)-phenylphosphine borane (R)-(IV-k). Purification: column chromatography (elution with 3:1 petroleum ether/ethyl acetate). Orange solid; Yield 60%; Enantiomeric excess: 99% by HPLC analysis (chiralpak AD, 0.2 mL·min$^{-1}$, hexane-2-propanol 98:2, t$_R$ (R)=21.2 min, t$_R$ (S)=24.7 min; R$_f$ 0.62 (petroleum ether/ethyl acetate 3:1); [C]$_D$ −51.4 (c 0.4, CHCl$_3$); IR (neat) 2915, 2843, 2468, 2418, 2200, 1436, 1179, 1171, 1108, 1027, 1000, 967, 838, 751, 742, 691 cm$^{-1}$; $^1$H NMR (300 MHz, CDCl$_3$) δ 0.77-0.80 (m, 6H, Hcy), 0.98-0.99 (m, 2H, Hcy), 1.10-1.19 (m, 5H, Hcy), 1.32-1.40 (m, 4H, Hcy), 1.46-1.47 (m, 1H, Hcy), 1.59-1.66 (m, 4H, Hcy), 3.80-3.81 (m, 1H, Hfer), 4.20 (s, 5H, Hfer), 4.31-4.32 (m, 1H, Hfer), 4.38-4.39 (m, 1H, Hfer), 4.41-4.42 (m, 1H, Hfer), 7.11-7.14 (m, 3H, Harom), 7.27-7.32 (m, 1H, Harom), 7.36-7.44 (m, 3H, Harom), 7.66-7.72 (m, 2H, Harom); $^{13}$C NMR (75.5 MHz, CDCl$_3$) δ 27.3 (d, J=27.8 Hz, CH$_2$), 28.4 (d, J=24.5 Hz, CH$_2$), 28.8 (d, J=19.5 Hz, CH$_2$), 31.0 (d, J=12.9 Hz, CH$_2$), 31.8 (d, J=15.3 Hz, CH$_2$), 33.4 (CH), 69.7 (Cfer), 70.0 (d, J=75.6 Hz, Cfer), 70.9 (d, J=7.3 Hz, Cfer), 72.2 (d, J=14.8 Hz, Cfer), 72.7 (d, J=8.7 Hz, Cfer), 73.0 (d, J=6.1 Hz, Cfer), 125.2 (d, J=8.5 Hz, Carom), 128.2 (d, J=64.4 Hz, Carom), 128.4 (d, J=10.5 Hz, Carom), 129.9 (d, J=2.7 Hz, Carom), 130.3 (d, J=15.5 Hz, Carom), 130.6 (d, J=68.9 Hz, Carom), 131.0 (d, J=2.4 Hz, Carom), 132.1 (d, J=5.5 Hz, Carom), 132.7 (d, J=9.4 Hz, Carom); $^{31}$P NMR (121 MHz, CDCl$_3$) δ 8.3; HRMS calcd for C$_{34}$H$_{43}$PB$_2$FeNa (M+Na)$^+$ 583.2542. found 583.2550; Anal calcd for C$_{34}$H$_{43}$PB$_2$Fe: C, 72.90; H, 7.74. found: C, 73.20; H, 7.94.

E.2. Synthesis of o-boronato free phosphine (1-43)

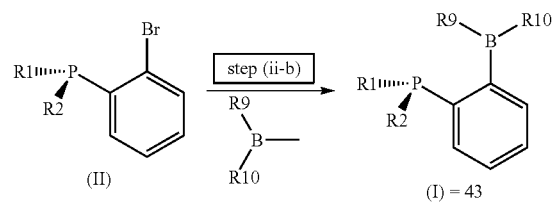

Synthesis of (S)-(2-methoxyphenyl)-phenyl-[2-(4,4,5,5-tetramethyl-[1,3,2]dioxaborolan-2-yl)-phenyl] phosphine 43i

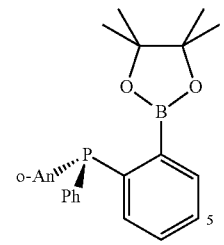

43i

To a solution of o-bromophenylphosphine (R)-(II-i) (0.15 g, 0.41 mmol) in dry THF (2 mL) was added dropwise under argon at −78° C. n-BuLi (0.45 mmol). The resulting solution was stirred at this temperature during 30 minutes and boron derivatives (2-isopropoxy-4,4,5,5-tetramethyl-1,3,2-dioxaborolane) (0.13 mL, 0.66 mmol) was then added dropwise. After 30 minutes at −78° C. and 20 hours at room temperature, the reaction mixture was quenched with water (10 mL) and extracted with methylene chloride (3×10 mL). The organic phases were dried over MgSO$_4$, filtered and the solvent evaporated giving a residue which was purified by column chromatography on silica gel using petroleum ether/ethyl acetate 5:1 as eluent. White solid; Yield 58%; Enantiomeric excess: 99% by HPLC analysis (chiralpak AD, 0.2 mL·min$^{-1}$, hexane-2-propanol 99:1, t$_R$ (R)=26.4 min, t$_R$ (S)=34.1 min; R$_f$ 0.33 (petroleum ether/ethyl acetate 5:1); [α]$_D$=−21.2 (c 0.3, CHCl$_3$); IR (neat) 3053, 2978, 2932, 1583, 1471, 1430, 1379, 1347, 1313, 1271, 1240, 1143, 1101, 1047, 1024, 963, 858, 744, 697 cm$^{-1}$; $^1$H NMR (300

MHz, CDCl$_3$) δ 1.01-1.02 (2s, 12H, CH$_3$), 3.68 (s, 3H, OCH$_3$), 6.60 (ddd, J=1.7, 4.3, 7.4 Hz, 1H, Harom), 6.71-6.82 (m, 3H, Harom), 7.18-7.24 (m, 8H, Harom), 7.72-7.76 (m, 1H, Harom); $^{13}$C NMR (75.5 MHz, CDCl$_3$) δ 24.5-24.6 (2s, CH$_3$), 55.7 (OCH$_3$), 83.8 (C(CH$_3$)$_2$), 110.0 (d, J=1.5 Hz, Carom), 121.0 (Carom), 127.0 (Carom), 127.2 (d, J=13.9 Hz, Carom), 128.3 (d, J=7.3 Hz, Carom), 128.4 (Carom), 130.0 (Carom), 130.4 (Carom), 132.1 (d, J=1.2 Hz, Carom), 134.0 (Carom), 134.4 (Carom), 134.7 (Carom), 135.5 (d, J=9.0 Hz, Carom), 138.0 (d, J=11.7 Hz, Carom), 143.5 (d, J=19.0 Hz, Carom), 161.4 (d, J=15.8 Hz, Carom); 31P NMR (121 MHz, CDCl$_3$) δ −15.4; HRMS calcd for C$_{25}$H$_{28}$PBO$_3$Na (M+Na)$^+$ 419.1946. found 419.1932; Anal calcd for C$_{25}$H$_{28}$PBO$_3$: C, 71.79; H, 6.75. found: C, 71.60; H, 6.56.

F. Synthesis of o-Carbinol Phosphine Derivatives (III-44) and (I-45)

F.1. Synthesis of o-Carbinol Phosphine Boranes (III-44)

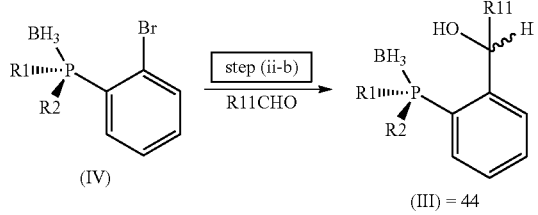

TABLE 4

Synthesis of hydroxyphosphine boranes (III-44)

| o-bromo phosphines borane (IV) | | Aldehyde | hydroxyphosphines borane (III-44) | | |
|---|---|---|---|---|---|
| R$^1$ | R$^2$ | R$^{11}$ | ratio 44:44' | rdt (%) | ee (%) |
| (R)-(IV-k) Fc | Ph | Ph | 44,44'a 45:55 | 71 | 99 |
| (S)-(IV-k) Ph | Fc | Ph | 44,44'b 64:26 | 72 | 99 |
| (S)-(IV-k) Ph | Fc | t-Bu | 44,44'c 60:40 | 66 | 99 |

General Procedure

To a solution of o-bromophosphine borane (IV) (0.4 mmol) in dry THF (2 mL) was added n-butyllithium at −78° C. (0.44 mmol, 1.1 eq.). After stirring during one hour at −78° C., a solution of aldehyde (0.8 mmol, 2 eq (benzaldehyde 57a) or 1.6 mmol, 4 éq (pivaldehyde 57b) in dry THF (0.5 mL) was added dropwise. The reaction mixture was stirred during 1 h30 to room temperature, then hydrolyzed with water (2 mL) and extracted with methylene chloride (3×5 mL). The combined organic phases were dried over MgSO$_4$ and the solvent was removed in vacuo to give a diastereomeric mixture, which was purified and separed by chromatographic column on silica gel using ethyl acetate/petroleum ether as eluent.

F.1.1. (Sp)-[2-(Ferrocenylphenylphosphino borane)-phenyl]phenyl methanol 44a/44a'

185 mg of (R)-ferrocenyl-o-bromophenylphosphine borane (IV-k) and 170 mg of benzaldehyde were used to afford the corresponding hydroxyphosphine borane 44b and 44b', with 71% overall yield and a diastereomeric ratio 44a/44a' 45:55.

(Sp,S)-[2-(Ferrocenylphenylphosphino borane)-phenyl]phenyl methanol 44a

Orange solid—R$_f$: 0.65 (ethyl acetate/petroleum ether 1:9)—mp=70-72° C.
Enantiomeric excess >99%; [α]$_D$=+31.0 (c=0.2; CHCl$_3$).
IR (cm$^{-1}$): 3499 (OH), 3057-2855 (C—H), 2429 (BH), 2053, 1983, 1950, 1886, 1670, 1590, 1570, 1499, 1471, 1453, 1438, 1412, 1381, 1348, 1314, 1264, 1226, 1197, 1185, 1172, 1130, 1107, 1065, 1034, 1019, 1003, 958, 887, 816, 768, 699.
$^1$H NMR (300 MHz, CDCl$_3$): δ(ppm)=1.35-1.91 (m, 3H, BH$_3$), 4.10 (s, 5H, Fc), 4.13 (s, 1H, Fc), 4.20 (s, 1H, Fc), 4.56 (s, 1H, Fc), 6.14 (s, 1H, CHOH), 6.76-6.79 (m, 2H, Harom), 6.78-7.04 (m, 1H, Harom), 7.09-7.15 (m, 3H, Harom), 7.17-7.21 (m, 2H, Harom), 7.33-7.38 (m, 1H, Harom) 7.47-7.65 (m, 2H, Harom).
RMN$^{13}$C NMR (75 MHz, CDCl$_3$): δ(ppm)=69.8 (d, J=3.8 Hz, Fc), 69.9 (Fc), 70.7 (d, J=7.5 Hz, Fc), 71.6 d, J=2.3 Hz, Fc), 72.2 (d, J=2.3 Hz, Fc), 72.3 (d, J=17.3 Hz, Fc), 74.8 (d, J=16.6 Hz, CHOH), 126.0 (Carom), 126.7 (Carom), 127.3 (Carom), 127.8 (Carom), 128.5 (d, J=3.8 Hz, Carom), 129 (d, J=8.3 Hz, Carom), 130.3 (d, J=16.6 Hz, Carom), 130.7 (d, J=8.3 Hz, Carom), 131.0 (d, J=12.0 Hz, Carom), 131.5 (d, J=2.3 Hz, Carom), 131.7 (d, J=2.3 Hz, Carom), 132.4 (d, J=6.0 Hz, Carom), 132.6 (d, J=9.8 Hz, Carom), 133.1 (d, J=9.8 Hz, Carom).
$^{31}$P NMR (121 MHz, CDCl$_3$): δ (ppm)=+13.7 (sl).
Exact mass calculated for C$_{29}$H$_{28}$BFeNaOP [M+Na]$^+$: 513.1218, tr. 513.1214.
Enantiomeric purity was determined by HPLC on chiral column (Chiralcel OD-H, hexane/iPrOH 98:2, 0.8 mL·min$^{-1}$, J=254 nm, 20° C., t$_R$ (Rp, Rc)=21.7 min, t$_R$ (Sp, Rc)=25.9 min, t$_R$ (Sp, Sc)=34.9 min, t$_R$ (Rp, Sc)=49 min.

(Sp,R)-[2-(Ferrocenylphenylphosphino borane)-phenyl]phenyl methanol 44a'

Orange solid—R$_f$: 0.65 (ethyl acetate/petroleum ether 1:9)—mp=172-174° C.
Enantiomeric excess >99%*; [α]$_D$=−85 (c=0.2; CHCl$_3$).
IR (cm$^{-1}$): 3509 (OH), 3088-2907 (C—H), 2394 (BH), 1705, 1606, 1568, 1495, 1472, 1449, 1437, 1371, 1318, 1262, 1232, 1171, 1126, 1107, 1068, 1017, 1003, 935, 919, 897, 839, 817, 768, 749, 735, 700, 654.
$^1$H NMR (300 MHz, CDCl$_3$): δ (ppm)=1.23-1.30 (m, 3H, BH$_3$), 4.10 (s, 5H, Fc), 4.12 (s, 1H, Fc), 4.56 (s, 1H, Fc), 4.66 (s, 1H, Fc), 4.79 (s, 1H, Fc), 6.14 (s, 1H, CHOH), 6.76-6.79 (m, 2H, Harom), 6.98-7.09 (m, 1H, Harom), 7.12-7.18 (m, 3H, Harom), 7.20-7.21 (m, 2H, Harom), 7.33-7.38 (m, 1H, Harom) 7.51-7.63 (m, 3H, Harom), 7.86-7.93 (m, 2H, Harom). $^{13}$C NMR (75 MHz, CDCl$_3$): δ (ppm)=69.8 (d, J=3.8 Hz, Fc), 69.9 (Fc), 70.7 (d, J=7.5 Hz, Fc), 71.6 (d, J=2.3 Hz, Fc), 72.1 (d, J=2.3 Hz, Fc), 72.2 (d, J=17.3 Hz, Fc), 74.8 (d, J=16.5 Hz, CHOH), 126 (Carom), 126.7 (Carom), 127.3 (Carom), 127.8 (Carom), 128.5 (d, J=3.8 Hz, Carom), 129.0 (d, J=8.3 Hz, Carom), 130.3 (d, J=16.6 Hz, Carom), 130.7 (d, J=8.3 Hz, Carom), 131.1 (d, J=12 Hz, Carom), 131.0 (d, J=2.5 Hz, Carom), 131.8 (d, J=2.2 Hz, Carom), 132.1 (d, J=6.1 Hz, Carom), 132.6 (d, J=9.7 Hz, Carom), 133.1 (d, J=9.7 Hz, Carom).
$^{31}$P NMR (121 MHz, CDCl$_3$): δ (ppm)=+14.2 (sl).
Exact mass calculated for C$_{29}$H$_{28}$BFeNaOP [M+Na]$^+$: 513.1218, tr. 513.1214.
Enantiomeric purity was determined by HPLC on chiral column (Chiralcel OD-H, hexane/iPrOH 98:2, 0.8 mL·min, λ=254 nm, 20° C., $t_R$ (Rp, Rc)=21.7 min, $t_R$ (Sp, Rc)=25.9 min, $t_R$ (Sp, Sc)=34.9 min, $t_R$ (Rp, Sc)=49 min.

F.1.2. (Rp)-[2-(Ferrocenyllhenyhlphoshino borane)-phenyl] phenylmethanol 44b and 44b'

185 mg of (S)-ferrocenyl-o-bromophenylphosphine borane (IV-k) and 170 mg of benzaldehyde were used to afford the corresponding hydroxyphosphine borane 44b and 44b', with 72% overall yield and a diastereomeric ratio 44b/44b' 64:26.

(Rp,R)-[2-(Ferrocenylphenylphosphino borane)-phenyl]phenyl methanol 44b'

Orange solid—$R_f$: 0.65 (ethyl acetate/petroleum ether 1:9)—mp=172-174° C. Enantiomeric excess >99%*; $[\alpha]_D$=−30.1 (c=0.2; CHCl$_3$).

IR (cm$^{-1}$): 3572 (OH), 3057-2922 (C—H), 2391 (BH), 1590, 1494, 1436, 1412, 1367, 1313, 1171, 1130, 1108, 1060, 1025, 823, 763, 744, 730, 698.

$^1$H NMR (300 MHz, CDCl$_3$): δ(ppm)=1.23-1.70 (m, 3H, BH$_3$), 4.08 (s, 5H, Fc), 4.17 (s, 1H, Fc), 4.56 (s, 1H, Fc), 4.66 (s, 1H, Fc), 4.90 (s, 1H, Fc), 6.33 (d, J=2.7 Hz, 1H, CHOH), 7.05-7.10 (m, 1H, Harom), 7.17-7.24 (m, 1H, Harom), 7.27-7.30 (m, 2H, Harom), 7.31-7.32 (m, 2H, Harom), 7.33-7.40 (m, 3H, Harom) 7.57-7.64 (m, 3H, Harrom), 7.89-7.96 (m, 2H, Harom).

$^{13}$C NMR (75 MHz, CDCl$_3$): δ(ppm)=69.4 (d, J=70.2 Hz, Fc), 69.9 (Fc), 71.1 (d, J=6.8 Hz, Fc), 71.4 (d, J=3 Hz, Fc), 72.1 (d, J=6.8 Hz, Fc), 72.4 (d, J=8.3 Hz, Fc), 75 (d, J=16.6 Hz, CHOH), 126.2 (Carom), 126.8 (Carom), 127.4 (d, J=51 Hz, Carom), 127.6 (d, J=13.6 Hz, Carom), 127.9 (Carom), 128.6 (Carom), 129.1 (d, J=9.8 Hz, Carom), 130.8 (d, J=8.3 Hz, Carom), 131.0 (d, J=27.9 Hz, Carom), 131.6 (Carom), 131.9 (d, J=2.3 Hz, Carom), 132.0 (Carom), 132.7 (d, J=7.5 Hz, Carom), 132.9 (d, J=2.3 Hz, Carom).

$^{31}$P NMR (121 MHz, CDCl$_3$): δ(ppm)=+16.19 (sl).

Exact mass calculated for C$_{29}$H$_{28}$BFeNaOP [M+Na]$^+$: 513.1218, tr. 513.1221.

Enantiomeric purity was determined by HPLC on chiral column (Chiralcel OD-H, hexane/iPrOH 98:2, 0.8 mL·min$^{-1}$, λ=254 nm, 20° C., $t_R$ (Rp, Rc)=21.7 min, $t_R$ (Sp, Rc)=25.9 min, $t_R$ (Sp, Sc)=34.9 min, $t_R$ (Rp, Sc)=49 min.

(Rp,S)-[2-(Ferrocenylphenylphosphino borane)-phenyl]phenyl methanol 44b

Orange solid—$R_f$: 0.66 (ethyl acetate/petroleum ether 1:9)—mp=92-94° C.

Excès énantiomérique >99%*—$[\alpha]_D$=+62 (c=0.2; CHCl$_3$).

IR (cm$^{-1}$): 3498 (OH), 3055 (C—H), 2424 (BH), 1588, 1470, 1436, 1410, 137, 1312, 1261, 1182, 1170, 1105, 1063, 1031, 1017, 1001, 828, 766, 738, 697, 657, 639.

$^1$H NMR (300 MHz, CDCl$_3$): δ(ppm)=0.86-1.34 (m, 3H, BH$_3$), 4.11 (s, 5H, Fc), 4.14 (s, 1H, Fc), 4.57 (s, 1H, Fc), 4.66 (s, 1H, Fc), 4.80 (s, 1H, Fc), 6.15 (d, J=3 Hz, 1H, CHOH), 6.78-6.99 (m, 2H, Harom), 7.01-7.20 (m, 1H, Harom), 7.14-7.22 (m, 5H, Harom), 7.33-7.42 (m, 1H, Harom), 7.51-7.63 (m, 3H, Harom) 7.87-7.94 (m, 2H, Harom).

$^{13}$C NMR (75 MHz, CDCl$_3$): δ(ppm)=69.0 (d, J=72.4 Hz, Fc), 69.9 (Fc), 70.7 (d, J=7.5 Hz, Fc), 71.6 d, J=2.3 Hz, Fc), 72.2 (d, J=2.3 Hz, Fc), 72.3 (d, J=17.3 Hz, Fc), 74.8 (d, J=17.4 Hz, CHOH), 126.0 (Carom), 126.7 (Carom), 127.3 (d, J=8.3 Hz, Carom), 127.7 (Carom), 128.8 (d, J=10.6 Hz, Carom), 130.3 (d, J=17.3 Hz, Carom), 130.7 (d, J=8.3 Hz, Carom), 131.0 (d, J=12.1 Hz, Carom), 131.5 (d, J=2.3 Hz, Carom), 131.7 (d, J=2.3 Hz, Carom), 132.4 (d, J=6 Hz, Carom), 133.1 (d, J=9.8 Hz, Carom), 141.0 (d, J=11.3 Hz, Carom), 146.6 (d, J=11.3 Hz, Carom).

$^{31}$P NMR (121 MHz, CDCl$_3$): δ(ppm)=+12.8 (sl).

Exact mass calculated for C$_{29}$H$_{28}$BFeNaOP [M+Na]$^+$: 513.1218. found: 513.1233.

The enantiomeric purity was determined by HPLC on chiral column (Chiralcel OD-H, hexane/iPrOH 98:2, 0.8 mL·min$^{-1}$, λ=254 nm, 20° C., $t_R$ (Rp, Rc)=21.7 min, $t_R$ (Sp, Rc)=25.9 min, $t_R$ (Sp, Sc)=34.9 min, $t_R$ (Rp, Sc)=49 min.

F.1.3. Synthesis of (R) t-butyl-(2-ferrocenylphenyphosphino borane)-phenyl methanol 44c and 44c'

185 mg of (S)-ferrocenylphenyl-o-bromophenylphosphine borane (IV-k) and 138 mg of pivaldehyde were used to afford the corresponding hydroxyphosphine borane 44c and 44c', with 66% overall yield and a diastereomeric ration 44c/44c'60:40.

(Rp,Rc) t-Butyl-(2-ferrocenylphenyphosphino borane)-phényl methanol 44c'

Orange solid—Rf: 0.56 (ethyl acetate/petroleum ether 1:9)—mp=170-172° C.

Enantiomeric excess >99%*—$[\alpha]_D$=−214 (c=0.2; CHCl$_3$).

IR (cm$^{-1}$): 3553 (OH), 2957-2900 (CH), 2396 (BH), 1568, 1464, 1438, 1416, 1395, 1362, 1311, 1292, 1235, 1197, 1171 (OCH$_3$), 1108, 1062, 1027, 1001, 829, 741, 699.

$^1$H NMR (300 MHz, CDCl$_3$): δ(ppm)=0.61 (s, 9H, CH$_3$) 1.44-1.72 (m, 3H, BH$_3$), 4.05 (s, 5H, Fc), 4.23 (s, 1H, Fc), 4.55 (s, 1H, Fc), 4.61 (s, 1H, Fc), 4.68 (s, 1H, Fc), 4.86 (d, J=3.9 Hz, 1H, CHOH), 7.0-7.07 (m, 1H, Harom), 7.14-7.20 (m, 1H, Harom), 7.39-7.45 (m, 1H, Harom), 7.55-7.57 (m, 3H, Harom) 7.70-7.77 (m, 1H, Harom), 7.89-7.94 (m, 2H, Harom).

$^{13}$C NMR (75 MHz, CDCl$_3$): δ(ppm)=26.7 (CH$_3$), 69.9 (Fc), 70.1 (d, J=72.4 Hz, Fc), 71.7 (d, J=2.3 Hz, C(CH$_3$)$_3$), 72.0 (d, J=6 Hz, Fc), 72.2 (d, J=9 Hz, Fc), 74.9 (d, J=16.6 Hz, CHOH), 76 (d, J=8.3 Hz, Fc), 127.0 (d, J=8.3 Hz, Carom), 128.4 (d, J=10.6 Hz, Carom), 128.7 (d, J=8.3 Hz, Carom), 130.3 (Carom), 130.8 (d, J=2.3 Hz, Carom), 130.9 (Carom), 131.5 (d, J=2.3 Hz, Carom), 131.6 (d, J=2.3 Hz, Carom), 132.7 (d, J=6.8 Hz, Carom), 133.4 (d, J=9 Hz, Carom).

$^{31}$P NMR (121 MHz, CDCl$_3$): δ(ppm)=+13.3 (m).

Exact mass calculated for C$_{27}$H$_{32}$BFeOPNa [M+Na]$^+$: 493.1531, tr. 493.1547.

Enantiomeric purity was determined by HPLC on chiral column (Chiralpack AD, hexane/iPrOH 99:1.1 mL·min$^{-1}$, λ=254 nm, 20° C., $t_R$((Sp,Rc ou Sc)=13.4 min, $t_R$(Rp, Sc)=14.7 min), $t_R$ ((Sp,Rcou Sc)=34.9 min, $t_R$ (Rp,Rc)=50.9 min).

(Rp,S) t-Butyl-(2-ferrocenylphenyphosphino borane)-phenyl methanol 44c

Orange solid—$R_f$: 0.35 (ethyl acetate/petroleum ether 1:9)—mp=160-162° C.

Enantiomeric excess >99%* −$[\alpha]_D$=−232 (c=0.2; CHCl$_3$).

IR (cm$^{-1}$): 3585 (OH), 2950 (C—H), 2420 (BH), 2364, 2161, 2069, 1587, 1479, 1435, 1261, 1230, 1205, 1171, 107, 1070, 1056, 1026, 1002, 907, 857, 826, 781, 764, 749, 728, 704, 683.

$^1$H NMR (300 MHz, CDCl$_3$): δ(ppm)=0.94 (s, 9H, CH$_3$) 1.33-1.74 (m, 3H, BH$_3$), 4.01 (s, 5H, Fc), 4.04 (s, 1H, Fc), 4.50 (s, 1H, Fc), 4.62 (s, 1H, Fc), 4.73 (s, 1H, Fc), 4.88 (d, J=3.9 Hz, 1H, CHOH), 6.98-7.05 (m, 1H, Harom), 7.16-7.21 (m, 1H, Harom), 7.40-7.45 (m, 1H, Harom), 7.53-7.63 (m, 4H, Harom), 7.73-7.85 (m, 2H, Harom).

$^{13}$C NMR (75 MHz, CDCl$_3$): δ(ppm)=26.7 (CH$_3$), 69.9 (Fc), 70.8 (d, J=70.2 Hz, Fc), 71.3 d, J=9.8 Hz, Fc), 72.1 (d, J=6 Hz, Fc), 75.2 (d, J=16.6 Hz, CHOH), 76.9 (CH$_3$)$_3$), 127.0 (d, J=9 Hz, Fc), 128.5 (d, J=7.5 Hz, Carom), 128.8 (d, J=9.7 Hz, Carom), 131.0 (d, J=78.5 Hz, Carom), 132.0 (d, J=35.5 Hz, Carom), 132.6 (d, J=9 Hz, Carom), 133.4 (d, J=7.5 Hz, Carom), 146.4 (d, J=7.6 Hz, Carom).

RMN$^{31}$P (121 MHz, CDCl$_3$): δ (ppm)=+17.1 (m).

Exact mass calculated for C$_{27}$H$_{32}$BFeNaOP [M+Na]$^+$: 493.1531, tr. 493.1528.

Enantiomeric purity was determined by HPLC on chiral column (Chiralpack AD, hexane/iPrOH 98:2, 0.5 mL·min$^{-1}$, λ=254 nm, 20° C, t$_R$((Sp,Rc ou Sc)=13.4 min, t$_R$(Rp, Sc)=14.7 min) t$_R$ ((Sp,Rcou Sc)=34.9 min, t$_R$ (Rp,Rc)=50.9 min).

F.2. Synthesis of o-carbinol free phosphines (1-45)

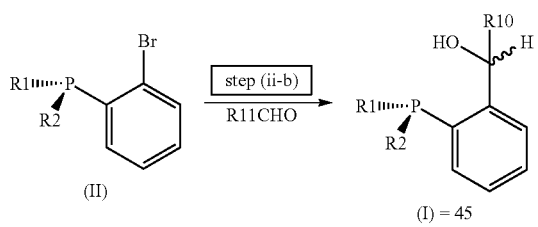

TABLE 5

| Synthesis of o-anisylhydroxyphosphines borane (I-45d,e) | | | | | |
|---|---|---|---|---|---|
| o-bromo phosphines | | | hydroxyphosphines borane (I-45) | | |
| (II) | | Aldehyde | | rdt | ee |
| R$^1$ | R$^2$ | R$^{11}$ | Ratio 45:45' | (%) | (%) |
| (S)-(II-i) | Ph | o-An | Ph | 45,45'd | 78:22 | 45 | 99 |
| (S)-(II-i) | Ph | o-An | t-Bu | 45,45'e | 38:62 | 50 | 99 |

F.2.1. Synthesis of (R)-[2-(o-anisylphenylphosphino)-phenyl]phenyl methanol 45d and 45d'

135 mg of (S)-o-anisyl-o-bromophenylphenylphosphine (II-i) and 170 mg of benzaldehyde 57a were used to afford the corresponding hydroxyphosphines 45d and 45d' in 45% overall yield and with a diastereomeric ratio 45d/45d'78:22.

(R)-[2-(o-anisylphenylphosphino)-phenyl]phenyl methanol 45d

White solid—R$_f$: 0.46 (ethyl acetate/petroleum ether 1:9)—mp=68-70° C.

Enantiomeric excess >99%*—[α]$_D$=+123 (c=0.2; CHCl$_3$).

IR (cm$^{-1}$): 3409 (OH), 3054-2834 (C—H), 2332, 2157, 2037, 1882, 1583, 1573, 1493, 1461, 1430, 1296, 1272, 1240, 1179, 1160, 1128, 1069, 1019, 916, 881, 850, 824, 793, 746, 696.

$^1$H NMR (300 MHz, CDCl$_3$): δ(ppm)=3.71 (s, 3H, OCH$_3$), 6.31 (sl, 1H, CHOH), 6.59-6.64 (m, 1H, Harom), 6.70 (d, J=6.9 Hz, 1H, Harom), 6.78-6.88 (m, 2H, Harom), 6.96-7.0 (m, 1H, Harom), 7.13-7.22 (m, 4H, Harom), 7.32-7.38 (m, 5H, Harom), 7.47-7.50 (m, 2H, Harom), 7.51-7.60 (m, 1H, Harom), 7.67-7.74 (m, 1H, Harom).

$^{13}$C NMR (75 MHz, CDCl$_3$): δ(ppm)=55.7 (OCH$_3$), 73.4 (d, J=24.9 Hz, CHOH), 110.2 (d, J=2.3 Hz, Carom), 111.8 (d, J=6.8 Hz, Carom), 121.0 (Carom), 121.2 (d, J=11.3 Hz, Carom), 124.8 (d, J=9.8 Hz, Carom), 126.7 (d, J=2.3 Hz, Carom), 126.8 (d, J=6.8 Hz, Carom), 127.8 (d, J=15.0 Hz, Carom), 127.9 (Carom), 128.5 (d, J=18.8 Hz, Carom), 128.6 (Carom), 129.5 (Carom), 130.4 (Carom), 131.2 (Carom), 133.9 (d, J=7.5 Hz, Carom), 134.2 (d, J=8.3 Hz, Carom), 136.0 (d, J=9.0 Hz, Carom), 141.8 (Carom), 143.5 (Carom), 148.7 (d, J=24.1 Hz, Carom).

$^{31}$P NMR (121 MHz, CDCl$_3$): δ(ppm)=−28.1 (s).

Exact mass calculated for C$_{24}$H$_{27}$NaO$_2$P [M+Na]$^+$: 421.1328, tr. 421.1345.

Enantiomeric purity was determined by HPLC on chiral column (Lux 5μ cellulose-2, hexane/iPrOH 90:10, 1 mL·min$^{-1}$, λ=254 nm, 20° C, t$_R$((Sp,Rc ou Sc)=8.7 min, t$_R$(Rp,Rc ou Sc)=10.9 min, t$_R$(Sp,Rc ou Sc)=15.7 min, t$_R$(Rp, Rc ou Sc)=21.3 min).

(R)-[2-(o-anisylphenylphosphino)-phenyl]phenyl methanol 45d'

White oil—R$_f$: 0.30 (ethyl acetate/petroleum ether 1:9).

Enantiomeric excess >99%*—[α]$_D$=−47 (c=0.2; CHCl$_3$).

IR (cm$^{-1}$): 3355 (OH), 3058-2836 (C—H), 1952, 1899, 1812, 1584, 1573, 1494, 1471, 1453, 1431, 1296, 1273, 1240, 1179, 1162, 1128, 1107, 1069, 1019, 915, 881, 852, 821, 794, 742, 695, 649.

$^1$H NMR (300 MHz, CDCl$_3$): (ppm)=3.66 (s, 3H, OCH$_3$), 5.52 (d, J=8 Hz, 1H, CHOH), 6.74-6.80 (m, 1H, Harom), 6.81-7.08 (m, 2H, Harom), 7.12-7.24 (m, 6H, Harom), 7.27-7.42 (m, 5H, Harom), 7.47-7.67 (m, 2H, Harom), 7.72-7.78 (m, 2H, Harom). $^{13}$C NMR (75 MHz, CDCl$_3$): δ(ppm)=55.8 (OCH$_3$), 73 (d, J=24.9 Hz, CHOH), 110.4 (d, J=2.4 Hz, Carom), 111.5 (d, J=6.8 Hz, Carom), 121 (Carom), 121.2 (d, J=11.2 Hz, Carom), 124.3 (Carom), 126.8 (d, J=2.3 Hz, Carom), 126.9 (d, J=6.7 Hz, Carom), 127.8 (d, J=15 Hz, Carom), 128 (Carom), 128.5 (d, J=18.8 Hz, Carom), 128.6 (Carom), 129.5 (Carom), 130.2 (Carom), 133.2 (Carom), 133.6 (d, J=18.1 Hz, Carom), 134.1 (d, J=9.8 Hz, Carom), 134.7 (d, J=10.7 Hz, Carom), 141.8 (Carom), 142.8 (Carom), 149 (d, J=23.8 Hz, Carom).

$^{31}$P NMR (121 MHz, CDCl$_3$): δ(ppm)=−26.8 (s).

Exact mass calculated for C$_{24}$H$_{27}$NaO$_2$P [M+Na]$^+$: 421.1328, tr. 421.1346.

Enantiomeric purity was determined by HPLC on chiral column (Lux 5μ cellulose-2, hexane/iPrOH 90:10, 1 mL·min$^{-1}$, λ=254 nm, 20° C, t$_R$((Sp,Rc ou Sc)=8.7 min, t$_R$(Rp,Rc ou Sc)=10.9 min, t$_R$(Sp,Rc ou Sc)=15.7 min, t$_R$(Rp, Rc ou Sc)=21.3 min).

F.2.2. Synthesis of (R)-t-butyl-(2-o-anisylphenyphosphino)-phenyl methanol 45e and 45e'

135 mg of (S)-o-anisyl-o-bromophenylphenylphosphine (IV-i) and 138 mg of pivaldehyde 57b were used to afford the corresponding hydroxyphosphines 45e and 45e' with 50% overall yield and a diatereomeric ratio 45e/45e'38:62.

(R)-t-Butyl-(2-o-anisylphenyphosphino)-phenyl methanol 45e

White solid—R$_f$: 0.46 (ethyl acetate/petroleum ether 1:9)—mp=76-78° C.

Enantiomeric excess >99%*—[α]$_D$=+189 (c=0.2; CHCl$_3$).

IR (cm$^{-1}$): 3594 (OH), 2952-2835 (C—H), 1573, 1462, 1430, 1361, 1273, 1462, 1430, 1361, 1273, 1240, 1161, 1069, 1002, 745, 696.

$^1$H NMR (300 MHz, CDCl$_3$): δ(ppm)=1.04 (s, 9H, CH$_3$) 3.74 (s, 1H, OCH$_3$), 5.5 (d, J=7.5 Hz, 1H, CHOH), 6.69-6.88 (m, 1H, Harom), 6.90-6.97 (m, 3H, Harom), 7.14-7.21 (m, 3H, Harom), 7.31-7.36 (m, 5H, Harom), 7.61-7.63 (m, 1H, Harom).

$^{13}$C NMR (75 MHz, CDCl$_3$): δ(ppm)=26.4 (CH$_3$), 55.8 (OCH$_3$), 78.1 (d, J=25.6 Hz, CHOH), 110.4 (d, J=1.5 Hz, Carom), 112.0 (d, J=6.8 Hz, Carom), 121.1 (Carom), 121.3 (d, J=11.3 Hz, Carom), 126.8 (d, J=12.8 Hz, Carom), 127.4 (Carom), 128.3 (d, J=6.0 Hz, Carom), 128.6 (Carom), 130.1 (Carom), 132.9 (Carom), 133.7 (d, J=20.4 Hz, Carom), 134.7 (d, J=2.3 Hz, Carom), 135.4 (d, J=14.3 Hz, Carom), 136.2 (d, J=11.3 Hz, Carom), 147.8 (d, J=23.4 Hz, Carom) 160.7 (d, J=15.8 Hz, Carom).

$^{31}$P NMR (121 MHz, CDCl$_3$): δ (ppm)=−24.6 (s).

Exact mass calculated for C$_{24}$H$_{27}$NaO$_2$P [M+Na]$^+$: 401.1641, tr. 401.1653.

Enantiomeric purity was determined by HPLC on chiral column (Lux 5μ cellulose-2, hexane/iPrOH 98:2, 1 mL·min$^{-1}$, λ=254 nm, 20° C, $t_R$((Rp, Rcou Sc)=7.3 min, $t_R$((Sp,Rc on Sc)=8.4 min, $t_R$(Sp, Rc ou Sc)=10.2 min, $t_R$(Rp,Rc on Sc)=12.7 min).

(R)-t-Butyl-(2-o-anisylphenyphosphino)-phenyl methanol 45e'

White solid—R$_f$: 0.34 (ethyl acetate/petroleum ether 1:9)—mp=70-72° C.

Enantiomeric excess >99%*—[α]$_D$=+108 (c=0.2; CHCl$_3$).

IR (cm$^{-1}$): 3576-3448 (OH), 3054-2834 (C—H), 2340, 1725, 1583, 1573, 1461, 1430, 1393, 1361, 1271, 1240, 1180, 1161, 1128, 1089, 1068, 1041, 1024, 1001, 935, 903, 879, 850, 824, 794, 746, 732, 697.

$^1$H NMR (300 MHz, CDCl$_3$): δ(ppm)=1.01 (s, 9H, CH$_3$) 3.07 (s, 1H, OCH$_3$), 5.58 (d, J=8.1 Hz, 1H, CHOH), 6.61-6.65 (m, 1H, Harom), 6.84-6.89 (m, 2H, Harom), 6.96-7.19 (m, 1H, Harom), 7.14-7.19 (m, 1H, Harom), 7.32-7.40 (m, 7H, Harom), 7.62-7.64 (m, 1H, Harom).

$^{13}$C NMR (75 MHz, CDCl$_3$): δ(ppm)=27.0 (CH$_3$), 52.4 (C(CH$_3$)$_3$), 54.4 (OCH$_3$), 80.3 (d, J=4.7 Hz, CHOH), 110.4 (d, J=6.8 Hz, Carom), 110.7 (d, J=6.0 Hz, Carom), 119.8 (d, J=12.0 Hz, Carom), 125 (d, J=13.6 Hz, Carom), 128.1 (d, J=12.1 Hz, Carom), 128.2 (d, J=12.8 Hz, Carom), 129.1 (d, J=10.6 Hz, Carom), 129.6 (d, J=8.3 Hz, Carom), 130.2 (d, J=18.9 Hz, Carom), 130.9 (d, J=3.0 Hz, Carom), 131.4 (d, J=2.3 Hz, Carom), 132.0 (d, J=9.8 Hz, Carom), 132.9 (d, J=14.3 Hz, Carom), 133.7 (d, J=16.6 Hz, Carom) 134.2 (d, J=1.5 Hz, Carom), 134.4 (d, J=8.3 Hz, Carom).

$^{31}$P NMR (121 MHz, CDCl$_3$): δ(ppm)=−26.8 (s).

Exact mass calculated for C$_{24}$H$_{27}$NaO$_2$P [M+Na]$^+$: 401.1641, tr. 401.1629.

Enantiomeric purity was determined by HPLC on chiral column (Lux 5 cellulose-2, hexane/iPrOH 98:2, 1 mL·min$^{-1}$, λ=254 nm, 20° C, $t_R$((Rp, Rcou Sc)=7.3 min, $t_R$((Sp,Rc ou Sc)=8.4 min, $t_R$(Sp, Rc ou Sc)=10.2 min, $t_R$(Rp,Rc ou Sc)=12.7 min).

G. Synthesis of O-Acylaryl Phosphine Derivatives (1-46)

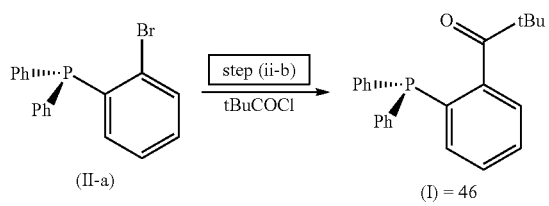

[o-(t-butylcarbonyl)phenyl]diphenylphosphine (1-46)

To a solution of (2-bromophenyl)diphenylphosphine (II-a) (0.50 mmol) in dry THF (2 mL) was added dropwise under argon at −78° C. n-BuLi (0.55 mmol). The resulting solution was stirred at this temperature during one hour and pivaloyl chloride (0.80 mmol) was then added dropwise. After stirring at room temperature overnight, the reaction mixture was quenched with water (10 mL) and extracted with methylene chloride (3×10 mL). The organic phases were dried over MgSO$_4$, filtered and the solvent evaporated giving a residue which was purified by column chromatography on silica gel using petroleum ether/ethyl acetate 3:1 as eluent. White solid; Yield 78%; R$_f$ 0.43 (petroleum ether/ethyl acetate 3:1); IR (neat) 3049, 2967, 2928, 2867, 1686, 1585, 1477, 1458, 1431, 1389, 1361, 1283, 1192, 967, 947, 778, 741, 691 cm$^{-1}$; $^1$H NMR (300 MHz, CDCl$_3$) δ 1.35 (s, 9H, CH$_3$), 7.18-7.22 (m, 1H, Harom), 7.25-7.40 (m, 13H, Harom); $^{13}$C NMR (75.5 MHz, CDCl$_3$) δ 27.7 (d, J=3.3 Hz, CH$_3$), 44.7 (C(CH$_3$)$_3$), 124.8 (d, J=8.6 Hz, Carom), 128.3 (Carom), 128.5 (d, J=4.9 Hz, Carom), 128.7 (Carom), 133.3 (Carom), 133.5 (Carom), 134.6 (d, J=15.8 Hz, Carom), 134.8 (d, J=2.2 Hz, Carom), 137.0 (d, J=10.4 Hz, Carom), 148.0 (d, J=35.8 Hz, Carom); $^{31}$P NMR (121 MHz, CDCl$_3$) δ −10.4; HRMS calcd for C$_{23}$H$_{23}$PONa [M+Na]$^+$ 369.1379. found 369.1382.

H. Synthesis of O-Silano Phosphine Derivatives (1-47)

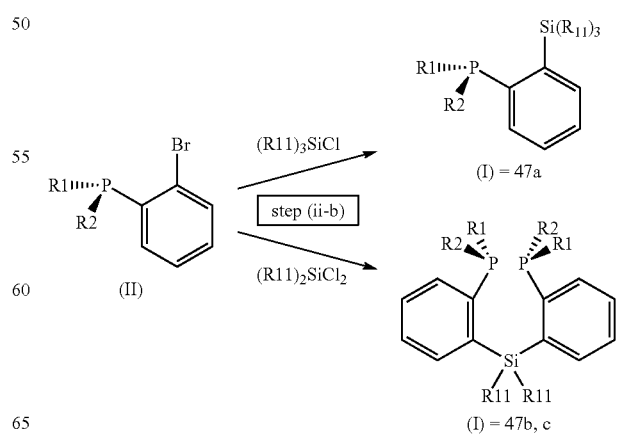

TABLE 6

Preparation of o-silanophosphines (I-47)

| o-bromo phosphines (II) | | | o-silanophosphines (I-47) | | |
|---|---|---|---|---|---|
| | $R^1$ | $R^2$ | $(R^{11})_{4-n}SiCl_n$ | Rdt (%) | e.e. (%) |
| (R)-(II-i) | o-An | Ph | $(Me)_3SiCl$ | 47a | 49 | >95 |
| (IV-g) | Ph | Ph | $(Me)_3SiCl$ | 47d | 25 | — |
| (II-a) | Ph | Ph | $Me_2SiCl_2$ | 47b | 52 | — |
| (S)-(II-i) | Ph | o-An | $Me_2SiCl_2$ | 47c | 61 | 99 |

H.1. Synthesis of o-silano phosphines 47a,d

H1.1. (R)-(2-methoxy-phenyl)-phenyl-(2-trimethylsilyl-phenyl)phosphine 47a

To a solution of (R)-(2-bromophenyl)-(2-methoxyphenyl)-phenylphosphine (II-i) (0.19 g, 0.50 mmol) in dry THF (2 mL) was added dropwise under argon at −78° C n-BuLi (0.55 mmol). The resulting solution was stirred at this temperature during one hour and trimethylsilylchloride (0.10 mL, 0.80 mmol) was then added dropwise. After stirring until room temperature during 20 h, the reaction mixture was quenched with water (10 mL) and extracted with methylene chloride (3×10 mL). The organic phases were dried over $MgSO_4$, filtered and the solvent evaporated giving a residue which was purified by column chromatography on silica gel using petroleum ether/methylene chloride 2:1 as eluent. White solid; Yield 49%; Enantiomeric excess >95% by $^{31}P$ NMR of the corresponding phosphine oxide with (R)-3,5-dinitro-N-(1-phenyl-ethyl)-benzamide as chiral reagent; $R_f$ 0.38 (petroleum ether/methylene chloride 2:1); $[\alpha]_D$ +1.6 (c 0.9, $CHCl_3$); IR (neat) 3057, 2960, 2900, 1583, 1572, 1472, 1431, 1272, 1242, 1182, 1160, 1125, 1114, 1021, 834, 753, 743 cm$^{-1}$; $^1H$ NMR (300 MHz, $CDCl_3$) δ 0.20 (d, J=1.5 Hz, $SiCH_3$), 3.53 (s, 3H, $OCH_3$), 6.48 (ddd, J=1.8, 4.2, 7.5 Hz, 1H, Harom), 6.65-6.71 (m, 2H, Harom), 6.91-6.93 (m, 1H, Harom), 7.00-7.06 (m, 4H, Harom), 7.10-7.17 (m, 4H, Harom), 7.44-7.45 (m, 1H, Harom), $^{13}C$ NMR (75.5 MHz, $CDCl_3$) δ −0.1 (d, J=9.6 Hz, $SiCH_3$), 54.3 ($OCH_3$), 109.0 (d, J=1.4 Hz, Carom), 119.6 (Carom), 125.9 (d, J=13.3 Hz, Carom), 126.7 (Carom), 126.8 (d, J=0.9 Hz, Carom), 126.9 (Carom), 127.0 (Carom), 127.7 (Carom), 128.7 (Carom), 132.1 (Carom), 132.4 (Carom), 133.3 (d, J=16.2 Hz, Carom), 133.7 (d, J=1.2 Hz, Carom), 136.3 (d, J=11.4 Hz, Carom), 141.7 (d, J=11.3 Hz, Carom), 146.3 (d, J=47.2 Hz, Carom), 159.6 (d, J=15.5 Hz, Carom); $^{31}P$ NMR (121 MHz, $CDCl_3$) δ −20.6; HRMS calcd for $C_{22}H_{25}POSiNa$ $(M+Na)^+$ 387.1304. found 387.1296; Anal calcd for $C_{22}H_{25}POSi$: C, 72.49; H, 6.91. found: C, 72.19; H, 7.02.

H.1.2. diphenyl-(2-trimethylsilyl-phenyl)phosphine 47d

To a solution of o-iodophosphine borane (IV-g) (0.19 g, 0.47 mmol) in dry THF (2 mL) was added dropwise under argon at −20° C. i-PrMgCl.LiCl (0.28 mL, 0.52 mmol). The resulting solution was stirred at this temperature during one hour and trimethylsilylchloride (0.09 mL, 0.71 mmol) was then added dropwise. After 30 minutes at −20° C. and 20 hours at room temperature, the reaction mixture was quenched with water (10 mL) and extracted with methylene chloride (3×10 mL). The organic phases were dried over $MgSO_4$, filtered and the solvent evaporated giving a residue which was purified by column chromatography on silica gel using petroleum ether/ethyl acetate (3/1) as eluent to afford the corresponding silylated phosphine. Colorless oil; Yield 25%; $^1H$ NMR (300 MHz, $CDCl_3$) δ 0.26 (d, J=1.5 Hz, 9H, $CH_3Si$), 7.08-7.18 (m, 13H, Harom), 7.50-7.54 (m, 1H, Harom); 31H NMR (121 MHz, CDCl3) δ −10.2 (s).

H.2. Synthesis of diphosphine 47b,c with a silano group as bridge

General Procedure

To a solution of o-bromophosphine (II) (0.50 mmol) in dry THF (3 mL) was added dropwise under argon at −78° C. n-BuLi (0.55 mmol). The resulting solution was stirred at this temperature during one hour and dichlorodimethylsilane (0.23 mmol) was then added dropwise. After stirring at room temperature overnight, the reaction mixture was quenched with water (10 mL) and extracted with methylene chloride (3×10 mL). The organic phases were dried over $MgSO_4$, filtered and the solvent evaporated giving a residue which was purified by column chromatography on silica gel and/or recrystallisation.

H.2.1. Diphosphine 47b

Purification: column chromatography (elution with 3:1 methylene chloride/petroleum ether) and recrystallisation in methyl alcohol/methylene chloride. White solid; Yield: 52%; $R_f$ 0.28 (methylene chloride/petroleum ether 3:1); IR (neat) 3045, 2966, 1583, 1478, 1431, 1251, 1108, 831, 809, 737, 694 cm$^{-1}$; H NMR (300 MHz, $CDCl_3$) δ 0.63 (t, J=1.5 Hz, 6H, $SiCH_3$), 6.90-6.95 (m, 8H, Harom), 7.06-7.21 (m, 18H, Harom), 7.64-7.68 (m, 2H, Harom); $^{13}C$ NMR (75.5 MHz, $CDCl_3$) δ 2.58 (t, J=10.1 Hz, $SiCH_3$), 127.9 (Carom), 128.1 (d, J=6.1 Hz, Carom), 128.2 (Carom), 129.1 (Carom), 133.2 (d, J=18.8 Hz, Carom), 135.2 (Carom), 136.3 (dd, J=2.8, 16.0 Hz, Carom), 138.4 (d, J=13.3 Hz, Carom), 143.0 (d, J=12.0 Hz, Carom), 148.0 (dd, J=3.3, 47.5 Hz, Carom); $^{31}P$ NMR (121 MHz, $CDCl_3$) δ −11.2; HRMS calcd for $C_{38}H_{34}P_2SiNa$ $[M+Na]^+$ 603.1797. found 603.1778.

H.2.2. Diphosphine 47c:

Purification: column chromatography (elution with 3:1 methylene chloride/petroleum ether). White solid; Yield: 61%; $R_f$ 0.10 (methylene chloride/petroleum ether 3:1); $[\alpha]_D$ —34.0 (c 0.3, $CHCl_3$) (ee=99%); IR (neat) 3049, 2954, 2833, 1575, 1467, 1271, 1239, 1110, 1023, 814, 741, 695 cm$^{-1}$; $^1H$ NMR (300 MHz, $CDCl_3$) δ 0.74-0.75 (m, 6H, $SiCH_3$), 3.66 (s, 6H, $OCH_3$), 6.66 (ddd, J=1.7, 4.1, 7.3 Hz, 2H, Harom), 6.82-6.86 (m, 4H, Harom), 7.04-7.07 (m, 6H, Harom), 7.17-7.32 (m, 12H, Harom), 7.64-7.66 (m, 2H, Harom); $^{13}C$ NMR (75.5 MHz, $CDCl_3$) δ 2.62 (dd, J=8.7, 12.6 Hz, $SiCH_3$), 55.5 ($OCH_3$), 110.3 (Carom), 120.8 (Carom), 127.3 (d, J=14.2 Hz, Carom), 127.8 (Carom), 127.9 (d, J=6.2 Hz, Carom), 128.7 (Carom), 129.7 (Carom), 133.5 (Carom), 133.6 (Carom), 133.9 (Carom), 134.9 (Carom), 136.4 (dd, J=2.1, 15.7 Hz, Carom), 137.5 (d, J=11.9 Hz, Carom), 142.7 (d, J=11.3 Hz, Carom), 147.1 (dd, J=2.5, 47.1 Hz, Carom), 160.8 (d, J=17.7 Hz, Carom); $^{31}P$ NMR (121 MHz, $CDCl_3$) δ −20.0.

I. Synthesis of 1,2-Diphosphinobenzenes (I-48)

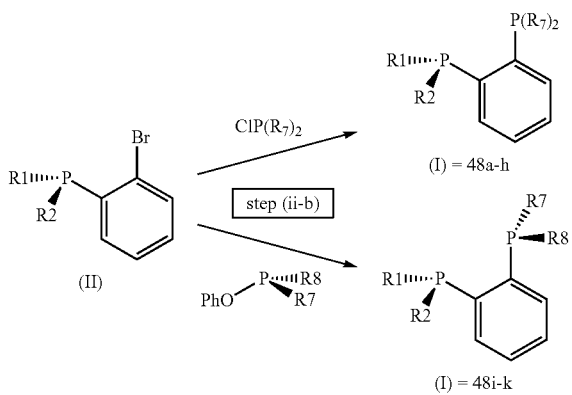

TABLE 7

Synthesis of 1,2-diphosphinobenzenes (I-48)

| o-bromophenylphosphines (II) | | 1,2-diphosphinobenzenes (I-48) | | | Rdt (%) | e.e. (%)[a] |
|---|---|---|---|---|---|---|
| | R[1] | R[2] | R[7] | R[8] | | |
| (S)-(II-i) | Ph | o-An | 48a | Ph | Ph | 70 | 99 |
| (S)-(II-i) | Ph | o-An | 48b | c-Hex | c-Hex | 47 | 99 |
| (S)-(II-i) | Ph | o-An | 48c | i-Pr | i-Pr | 43 | 99 |
| (S)-(II-i) | Ph | o-An | 48d | o-Tol | o-Tol | 37 | 99 |
| (S)-(II-i) | Ph | o-An | 48e | p-Tol | p-Tol | 52 | 99 |
| (S)-(II-i) | Ph | o-An | 48f | p-CF$_3$Ph | p-CF$_3$Ph | 58 | 99 |
| (S)-(II-k) | Ph | Fc | 48g | Ph | Ph | 56 | 99 |
| (R)-(II-m) | Ph | iPr | 48h | Ph | Ph | 54 | 98 |
| (II-a) | Ph | Ph | 48i | o-Tol | Ph | 54 | 99 |
| (S)-(II-i) | Ph | o-An | 48j | o-An | Ph | 52 | 99 |
| (R)-(II-m) | Ph | iPr | 48k | o-An | Ph | 56 | 99 |

[a] determined by HPLC on chiral column

I.1 Synthesis Using Chlorophosphines

General Procedure

To a solution of o-bromoarylphosphine (II) (0.54 mmol) in THF (2 mL) was added at −78° C. under argon n-BuLi (1.6 M in hexane) (0.37 mL, 0.59 mmol) and the resulting solution was stirred at this temperature during one hour. At this time, chlorophosphine (0.65 mmol) was added at −78° C. and the solution was stirred at room temperature overnight. After quenching with water, the mixture was extracted with methylene chloride (3×5 mL) and the organic phases were dried over MgSO$_4$. The solvent was evaporated under vacuum to give a residue which was purified by chromatographic column on silica gel and/or recrystallisation.

I.1.1. (Sp)-1-Diphenylphosphino-2-(o-anisylphenylphosphino)benzene 48a

Purification: column chromatography (elution with 3:1 petroleum ether/methylene chloride). Analytical pure sample was obtained by recrystallisation in methylene chloride/methyl alcohol. White solid; Yield 70%; Enantiomeric excess 99% by HPLC analysis (chiralpak AD, 0.2 mL·min$^{-1}$, hexane/2-propanol 99:1, $t_R$ (S) 44.5 min, $t_R$ (R) 61.9 min); R$_f$ 0.18 (petroleum ether/methylene chloride 3:1); $[\alpha]_D$ +58.6 (c 0.3, CHCl$_3$); IR (neat) 3048, 1581, 1571, 1469, 1431, 1299, 1272, 1240, 1180, 1160, 1129, 1090, 1069, 1022, 793, 743, 719 cm$^{-1}$; $^1$H NMR (300 MHz, CDCl$_3$) δ 3.57 (s, 3H, OCH$_3$), 6.56 (ddd, J=1.7, 4.4, 7.4 Hz, 1H, Harom), 6.67-6.75 (m, 2H, Harom), 6.90-7.00 (m, 2H, Harom), 7.04-7.22 (m, 18H, Harom); $^{13}$C NMR (75.5 MHz, CDCl$_3$) δ 55.6 (OCH$_3$), 110.2 (d, J=1.5 Hz, Carom), 120.8 (Carom), 125.9 (dd, J=6.7, 13.9 Hz, Carom), 128.1 (Carom), 128.2 (Carom), 128.3 (Carom), 129.0 (Carom), 130.0 (Carom), 133.6 (Carom), 133.7 (Carom), 133.8 (Carom), 133.9 (Carom), 134.0 (Carom), 134.1 (Carom), 134.2 (Carom), 134.3 (Carom), 136.5 (dd, J=4.9, 11.0 Hz, Carom), 137.4 (dd, J=5.1, 12.1 Hz, Carom), 143.3 (dd, J=10.7, 21.7 Hz, Carom), 143.6 (dd, J=9.5, 32.5 Hz, Carom), 161.0 (d, J=15.3 Hz, Carom); $^{31}$P NMR (121 MHz, CDCl$_3$) δ −14.0 (d, J=164.8 Hz), −23.6 (d, J=164.8 Hz); HRMS calcd for C$_{31}$H$_{26}$OP$_2$Na [M+Na]$^+$ 499.1351. found 499.1375.

I.1.2. (Sp)-1-dicyclohexylphosphino-2-(o-anisylphenylphosphino)-benzene 48b

Purification: column chromatography (elution with 3:1 petroleum ether/ethyl acetate). White solid; Yield 47%; Enantiomeric excess 99% by HPLC analysis (Lux 5µ Cellulose 2, 0.5 mL·min$^{-1}$, hexane/2-propanol 98:2, $t_R$ (S) 7.6 min, $t_R$ (R) 10.7 min); R$_f$ 0.62 (petroleum ether/ethyl acetate 3:1); $[\alpha]_D$ +57.1 (c 0.3, CHCl$_3$); IR (neat) 2922, 2847, 1582, 1571, 1471, 1445, 1430, 1241, 1041, 836, 752, 695 cm$^{-1}$; $^1$H NMR (300 MHz, CDCl$_3$) δ 1.00-1.20 (m, 10H, Hcy), 1.48-1.79 (m, 12H, Hcy), 3.62 (s, 3H, OCH$_3$), 6.54 (ddd, J=1.5, 3.6, 7.2 Hz, 1H, Harom), 6.73-6.85 (m, 3H, Harom), 7.09-7.7.27 (m, 9H, Harom), 7.43-7.47 (m, 1H, Harom); $^{13}$C NMR (75.5 MHz, CDCl$_3$) δ 26.4 (d, J=8.6 Hz, CH$_2$), 27.0-27.5 (m, CH$_2$), 28.8 (d, J=7.8 Hz, CH$_2$), 29.1 (d, J=10.5 Hz, CH$_2$), 34.0 (dd, J=5.4, 14.7 Hz, CH), 34.9 (dd, J=4.3, 15.4 Hz, CH), 55.6 (OCH$_3$), 110.1 (Carom), 120.8 (Carom), 127.5 (dd, J=9.1, 17.7 Hz, Carom), 127.8 (Carom), 128.0-128.1 (m, Carom), 128.6 (Carom), 129.7 (Carom), 132.4 (dd, J=2.2, 6.2 Hz, Carom), 133.4 (d, J=7.5 Hz, Carom), 134.2 (Carom), 134.3 (Carom), 134.6 (Carom), 137.3 (dd, J=3.8, 15.2 Hz, Carom), 141.7 (dd, J=17.0, 31.2 Hz, Carom), 146.2 (dd, J=8.2, 32.4 Hz, Carom), 160.8 (d, J=15.8 Hz, Carom); $^{31}$P NMR (121 MHz, CDCl$_3$) δ −12.2 (d, J=167.8 Hz), −23.2 (d, J=167.8 Hz); HRMS calcd for C$_{31}$H$_{38}$OP$_2$Na [M+Na]$^+$ 511.2290. found 511.2295.

I.1.3. (Sp)-1-di-i-propylphosphino-2-(o-anisylphenylphosphino)benzene 48c

Purification: column chromatography (elution with 3:1 petroleum ether/ethyl acetate). Colorless sticky oil; Yield 43%; Enantiomeric excess 99% by HPLC analysis (Lux 5µ Cellulose 2, 0.3 mL·min$^{-1}$, hexane/2-propanol 98:2, $t_R$ (S) 12.8 min, $t_R$ (R) 14.7 min); R$_f$ 0.63 (petroleum ether/ethyl acetate 3:1); $[\alpha]_D$ +85.0 (c 0.5 CHCl$_3$); IR (neat) 2948, 2864, 1572, 1461, 1429, 1271, 1240, 1180, 1104, 1070, 1025, 879, 746 cm$^{-1}$; $^1$H NMR (300 MHz, C$_6$D$_6$) δ 0.90 (dd, J=7.2, 12.0 Hz, 3H, CH$_3$), 1.12 (dd, J=7.2, 10.8 Hz, 3H, CH$_3$), 1.24 (dd, J=7.2, 13.8 Hz, 3H, CH$_3$), 1.36 (dd, J=7.2, 14.4 Hz, 3H, CH$_3$), 2.12-2.18 (m, 2H, CH), 3.30 (s, 3H, OCH$_3$), 6.61 (dd, J=4.4, 8.1 Hz, 1H, Harom), 6.86 (t, J=7.4 Hz, 1H, Harom), 7.06-7.11 (m, 2H, Harom), 7.18-7.24 (m, 5H, Harom), 7.31-7.33 (m, 1H, Harom), 7.46-7.48 (m, 1H, Harom), 7.57-7.60 (m, 2H, Harom); $^{13}$C NMR (75.5 MHz, C$_6$D$_6$) δ 19.2 (d, J=9.3 Hz, CH$_3$), 19.5 (d, J=12.5 Hz, CH$_3$), 20.1 (d, J=18.7 CH$_3$), 20.2 (dd, J=1.9, 18.6 Hz, CH$_3$), 24.3 (dd, J=5.6, 15.7 Hz, CH), 25.0 (dd, J=4.5, 16.6 Hz, CH), 54.9 (OCH$_3$), 110.1 (Carom), 121.0 (Carom), 128.1 (Carom), 128.2 (Carom), 128.3 (Carom), 128.8 (Carom), 129.7 (Carom), 132.2 (d, J=2.3 Hz, Carom), 132.3 (d, J=2.8 Hz, Carom), 133.4 (d, J=7.8 Hz, Carom), 134.6 (Carom), 134.9 (Carom), 135.0 (Carom), 138.2 (dd, J=4.9, 14.7 Hz, Carom), 142.1 (d, J=19.4 Hz, Carom), 142.3 (d, J=18.8 Hz, Carom), 147.1 (dd, J=11.2, 32.7 Hz, Carom), 161.2 (d, J=15.1 Hz, Carom); $^{31}$P NMR (121 MHz, C$_6$D$_6$) δ −3.7 (d, J=165.0 Hz), −20.7 (d, J=165.0 Hz); HRMS calcd for C$_{25}$H$_{30}$OP$_2$Na [M+Na]$^+$ 431.1664. found 431.1682.

I.1.4. (Sp)-1-di(o-tolyl)phosphino-2-(o-anisyl-phenylphosphino)benzene 48d

Purification: column chromatography (elution with 3:1 toluene/petroleum ether) and recrystallisation in methylene chloride/methyl alcohol. White solid; Yield 37%; Enantiomeric excess 99% by HPLC analysis (Lux 5µ Cellulose 2, 0.5 mL·min$^{-1}$, hexane/2-propanol 98:2, $t_R$ (S) 8.2 min, $t_R$ (R) 9.6 min); R$_f$ 0.39 (toluene/petroleum ether 3:1); $[\alpha]_D$ +73.0 (c 0.2, CHCl$_3$); IR (neat) 3050, 2929, 2834, 1573, 1469, 1429, 1272, 1241, 1130, 1108, 1070, 1025, 745 cm$^{-1}$; $^1$H NMR (300 MHz, C$_6$D$_6$) δ 2.38 (s, 3H, CH$_3$), 2.54 (s, 3H, CH$_3$), 3.23 (s, 3H, OCH$_3$), 6.56 (dd, J=4.2, 7.8 Hz, 1H, Harom), 6.82-6.85 (m, 1H, Harom), 7.01-7.26 (m, 14H, Harom), 7.27-7.30 (m, 2H, Harom), 7.38-7.39 (m, 1H, Harom), 7.53-7.55 (m, 1H, Harom); $^{13}$C NMR (75.5 MHz, C$_6$D$_6$) δ 21.1 (d, J=21.1 Hz, CH$_3$), 21.3 (d, J=21.1 Hz, CH$_3$), 54.9 (OCH$_3$), 126.0 (d, J=5.7 Hz, Carom), 126.9 (dd, J=6.9, 16.0 Hz, Carom), 128.1 (Carom), 128.2 (Carom), 128.3 (d, J=3.1 Hz, Carom), 128.5 (d, J=6.9 Hz, Carom), 129.1 (d, 4.6 Hz, Carom), 129.8 (Carom), 130.2 (2d, J=5.1 Hz; J=4.7 Hz, 2Carom), 133.7 (Carom), 133.9 (Carom), 134.0 (d, J=6.9 Hz, Carom), 134.1 (d, J=7.0 Hz, Carom), 134.2 (Carom), 134.4 (Carom), 134.6 (Carom), 136.1-136.3 (m, Carom), 137.5 (dd, J=4.7, 13.6 Hz, Carom), 142.7 (2dd, J=9.9, 34.0 Hz; J=15.2, 26.7 Hz, 2Carom), 155.7 (dd, J=11.1, 32.8 Hz, Carom), 162.2 (d, J=15.3 Hz, Carom); $^{31}$P NMR (121 MHz, $C_6D_6$) δ −22.0 (d, J=172.5 Hz), −26.3 (d, J=172.5 Hz); HRMS calcd for $C_{33}H_{31}OP_2$ [M+H]$^+$ 505.1845. found 505.1841.

I.1.5. (Sp)-1-di(p-tolyl)phosphino-2-(o-anisyl-phenylphosphino)benzene 48e

Purification: column chromatography (elution with 2:1 toluene/petroleum ether). White solid; Yield 52%; Enantiomeric excess 99% by HPLC analysis (Lux 5μ Cellulose 2, 0.5 mL·min$^{-1}$, hexane/2-propanol 90:10, $t_R$ (S) 8.0 min, $t_R$ (R) 10.9 min); $R_f$ 0.17 (toluene/petroleum ether 2:1); $[\alpha]_D$ +58.0 (c 0.3, CHCl$_3$); IR (neat) 3046, 2963, 2919, 1572, 1496, 1470, 1429, 1396, 1260, 1240, 1184, 1090, 1020, 803, 750, 696 cm$^{-1}$; $^1$H NMR (300 MHz, CDCl$_3$) δ 2.32-2.33 (2s, 6H, CH$_3$), 3.67 (s, 3H, OCH$_3$), 6.62 (ddd, J=1.7, 4.3, 7.4 Hz, 1H, Harom), 6.76-6.84 (m, 2H, Harom), 6.99-7.31 (m, 18H, Harom); $^{13}$C NMR (75.5 MHz, CDCl$_3$) δ 20.2 (CH$_3$), 20.3 (CH$_3$), 54.5 (OCH$_3$), 109.1 (d, J=1.3 Hz, 5 Carom), 119.7 (Carom), 125.0 (dd, J=6.5, 13.9 Hz, Carom), 127.0 (Carom), 127.1 (Carom), 127.6 (Carom), 127.8 (Carom), 127.9 (d, J=3.0 Hz, Carom), 128.0 (d, J=2.7 Hz, Carom), 128.8 (Carom), 132.6 (d, J=7.6 Hz, Carom), 132.7-133.2 (m, Carom), 135.6 (dd, J=4.8, 11.5 Hz, Carom), 136.9 5carom), 137.0 (Carom), 142.2 (dd, J=10.1, 31.6 Hz, Carom), 143.2 (dd, J=11.2, 32.4 Hz, Carom), 160.0 (d, J=15.4 Hz, Carom); $^{31}$P NMR (121 MHz, CDCl$_3$) δ −15.4 (d, J=162.8 Hz), −24.1 (d, J=162.8 Hz); HRMS calcd for $C_{33}H_{30}OP_2Na$ [M+Na]$^+$ 527.1664. found 527.1687.

I.1.6. (Sp)-1-di(p-trifluoromethylphenyl)phosphino-2-(o-anisylphenylphosphino)benzene 48f Purification: column chromatography (elution with 2:1 toluene/petroleum ether). White solid; Yield 58%; Enantiomeric excess 99% by HPLC analysis (Lux 5μ Cellulose 2, 0.3 mL·min, hexane/2-propanol 90:10, $t_R$ (S) 11.3 min, $t_R$ (R) 13.1 min); $R_f$ 0.56 (toluene/petroleum ether 2:1); $[\alpha]_D$ +52.9 (c 0.3, CHCl$_3$); IR (neat) 3050, 2933, 1431, 1397, 1320, 1242, 1163, 1120, 1105, 1059, 1015, 830, 750, 696 cm$^{-1}$; $^1$H NMR (300 MHz, CDCl$_3$) δ 3.57 (s, 3H, OCH$_3$), 6.48-6.52 (m, 1H, Harom), 6.65-6.74 (m, 2H, Harom), 6.90-7.01 (m, 2H, Harom), 7.06-7.25 (m, 12H, Harom), 7.35 (d, J=7.8 Hz, 2H, Harom), 7.41 (d, J=7.8 Hz, 2H, Harom); $^{13}$C NMR (75.5 MHz, CDCl$_3$) δ 55.6 (OCH$_3$), 120.9 (Carom), 124.0 (2q, J=272.4 Hz, 2CF$_3$), 124.9-125.1 (m, Carom), 128.2 (Carom), 128.4 (d, J=7.3 Hz, Carom), 128.7 (Carom), 129.1 (Carom), 129.3 (Carom), 129.6 (Carom), 130.4 (Carom), 130.5 (q, J=32.4 Hz, Carom), 133.9-134.2 (m, Carom), 134.5 (Carom), 135.6 (dd, J=4.5, 10.1 Hz, Carom), 140.8 (d, J=9.8 Hz, Carom), 141.3-141.8 (m, Carom), 144.2 (dd, J=10.5, 32.8 Hz, Carom), 161.0 (d, J=15.4 Hz, Carom); $^{31}$P NMR (121 MHz, CDCl$_3$) δ −14.5 (d, J=164.5 Hz), −24.0 (d, J=164.5 Hz); $^{19}$F NMR (282 MHz, CDCl$_3$) δ −62.8 (2s, CF$_3$); HRMS calcd for $C_{33}H_{24}OF_6P_2Na$ [M+Na]$^+$ 635.1099. found 635.1103.

I.1.7. (Rp)-1-diphenylphosphino-2-(ferrocenylphenylphosphino)benzene 48 g

To a solution of (S)-ferrocenyl-(2-bromophenyl)-phenylphosphine (II-k) (0.20 g, 0.45 mmol) in THF (2 mL) was added at −78° C. under argon n-BuLi (1.6 M in hexane) (0.37 mL, 0.50 mmol) and the resulting solution was stirred at this temperature during one hour. At this time, chlorodiphenylphosphine (0.09 mL, 0.54 mmol) was added at −78° C. and the solution was stirred at room temperature overnight. After quenching with water, the mixture was extracted with methylene chloride (3×5 mL) and the organic phases were dried over MgSO$_4$. The solvent was evaporated under vacuo to give a residue which was purified by chromatographic column on silica gel using toluene/petroleum ether (1/1) as eluent and recrystallisation in methylene chloride/acetone.

Purification: column chromatography (elution with 1:1 toluene/petroleum ether) and recrystallisation in methylene chloride/acetone. Orange solid; Yield: 56%; Enantiomeric excess 99% by HPLC analysis (Lux 5μ Cellulose 2, 1.0 mL·min$^{-1}$, hexane/2-propanol 98:2, $t_R$ (S) 5.5 min, $t_R$ (R) 7.9 min); $R_f$ 0.34 (toluene/petroleum ether 1:1); $[\alpha]_D$ −55.5 (c 0.2, CHCl$_3$); IR (neat) 3048, 1585, 1567, 1478, 1433, 1307, 1193, 1158, 1106, 1069, 1025, 1000, 888 cm; $^1$H NMR (300 MHz, $C_6D_6$) δ 4.04 (sl, 1H, Cp), 4.19 (sl, 5H, Cp), 4.22 (sl, 1H, Cp), 4.26 (sl, Cp), 4.37 (sl, 1H, Cp), 7.04-7.18 (m, 11H, Harom), 7.30-7.34 (m, 3H, Harom), 7.54-7.56 (m, 5H, Harom); $^{13}$C NMR (75.5 MHz, $C_6D_6$) δ 69.4 (Cfer), 70.6 (Cfer), 71.2 (d, J=5.3 Hz, Cfer), 72.7 (d, J=5.4 Hz, Cfer), 73.8 (d, J=24.1 Hz, Cfer), 77.4 (d, J=11.1 Hz, Cfer), 128.1 (Carom), 128.2 (2s, 2Carom), 128.3 (Carom), 128.5 (d, J=5.8 Hz, Carom), 128.8 (d, J=6.3 Hz, Carom), 133.6 (Carom), 133.7 (Carom), 133.8 (Carom), 134.2 (Carom), 134.4 (2s, 2Carom), 134.5 (Carom), 137.4 (dd, J=4.0, 12.5 Hz, Carom), 138.6 (dd, J=7.9, 14.0 Hz, Carom), 139.1 (d, J=9.8 Hz, Carom), 142.9 (dd, J=12.3, 30.8 Hz, Carom), 146.9 (dd, J=13.7, 32.3 Hz, Carom); $^{31}$P NMR (121 MHz, $C_6D_6$) δ −13.6 (d, J=155.5 Hz), −24.6 (d, J=155.5 Hz); HRMS calcd for $C_{34}H_{28}FeP_2Na$ [M+Na]+ 577.0908. found 577.0935.

I.1.8. (Rp)-1-diphenylphosphino-2-(isopropylphenylphosphino)benzene 48h

To a solution of (R)-(2-bromophenyl)-isopropylphenylphosphine (II-m) (0.14 g, 0.45 mmol) in THF (2 mL) was added at −78° C. under argon n-BuLi (1.6 M in hexane) (0.37 mL, 0.50 mmol) and the resulting solution was stirred at this temperature during one hour. At this time, chlorodiphenylphosphine (0.09 mL, 0.54 mmol) was added at −78° C. and the solution was stirred at room temperature overnight. After quenching with water, the mixture was extracted with methylene chloride (3×5 mL) and the organic phases were dried over MgSO$_4$. The solvent was evaporated under vacuo to give a residue which was purified by chromatographic column on silica gel using petroleum ether/toluene (2/1) as eluent.

White solid; Yield: 54%; Enantiomeric excess: 98% by HPLC analysis after transformation to the corresponding dithiophosphine (Lux 5μ Cellulose 2, 0.8 mL·min, hexane/2-propanol 80:20, $t_R$ (R)=16.2 min, $t_R$ (S)=18.2 min; $R_f$ 0.39 (petroleum ether/toluene 2:1); $[\alpha]_D$ +61.7 (c 0.3, CHCl$_3$); IR (neat) 3050, 2962, 2923, 2864, 1477, 1433, 1381, 1363, 1305, 1270, 1229, 1181, 1155, 1091, 1069, 1025, 999, 745, 695, 648 cm$^{-1}$; H NMR (300 MHz, CDCl$_3$) δ 1.07 (ddd, J=2.6, 6.8, 13.6 Hz, 3H, CH$_3$), 1.11 (ddd, J=2.9, 6.8, 12.8 Hz, 3H, CH$_3$), 2.48-2.55 (m, 1H, CH), 6.94-6.97 (m, 1H, Harom), 7.07-7.35 (m, 16H, Harom), 7.38 (td, J=1.3, 7.5 Hz, 1H, Harom), 7.66-7.68 (m, 1H, Harom); $^{13}$C NMR (75.5 MHz, CDCl$_3$) δ 19.5 (dd, J=3.4, 18.4 Hz, CH$_3$), 19.7 (dd, J=3.4, 16.2 Hz, CH$_3$), 25.9 (dd, J=4.6, 7.1 Hz, CH), 127.9 (Carom), 128.0 (Carom), 128.1 (Carom), 128.2 (2s, Carom), 128.3 (Carom), 128.4 (Carom), 128.7 (Carom), 128.9 (Carom), 131.9 (d, J=5.1 Hz, Carom), 133.3 (d, J=3.4 Hz, Carom), 133.4 (d, J=3.7 Hz, Carom), 133.9 (d, J=6.1 Hz, Carom), 134.0 (t, J=4.1 Hz, Carom), 134.2 (t, J=4.4 Hz, Carom), 136.9 (d, J=9.5 Hz, Carom), 137.7 (d, J=11.8 Hz, Carom), 138.0 (dd, J=5.3, 10.2 Hz, Carom), 143.5 (dd, J=6.5, 22.8 Hz, Carom), 144.8 (dd, J=3.9, 25.0 Hz, Carom); $^{31}$P NMR (121 MHz, CDCl$_3$) δ −13.1 (d, J=155.8 Hz), −14.2 (d, J=155.8 Hz); HRMS calcd for $C_{27}H_{27}P_2$ [M+H]$^+$ 413.1582. found 413.1586.

I.2. Synthesis using phenyl phosphinites

I.2.1. (Sp)-1-diphenylphosphino-2-(o-tolylphenylphosphino)benzene 48i

To a solution of o-bromodiphenylphosphine (II-a) (0.20 g, 0.59 mmol) in THF (3 mL) was added at −78° C. under argon n-BuLi (1.6 M in hexane) (0.41 mL, 0.65 mmol) and the resulting solution was stirred at this temperature during one hour. At this time, a solution of (R)-phenyl-o-tolylphenylphosphinite (0.17 g, 0.59 mmol) in THF (2 mL) was added dropwise at −78° C. and the mixture was stirred at room temperature overnight. After quenching with water, the mixture was extracted with methylene chloride (3×5 mL) and the organic phases were dried over MgSO$_4$. The solvent was evaporated under vacuo to give a residue which was purified by chromatographic column on silica gel using toluene/petroleum ether (1/1) as eluent.

Colorless sticky solid; Yield: 54%; Enantiomeric excess: 99% by HPLC analysis (Lux 5µ Cellulose 2, 0.2 mL·min$^{-1}$, hexane/2-propanol 98:2, $t_R$ (S)=19.5 min, $t_R$ (R)=20.8 min; $R_f$ 0.43 (petroleum ether/toluene 1:1); [α]$_D$ +33.0 (c 0.3 CHCl$_3$); IR (neat) 3051, 1584, 1477, 1433, 1269, 1068, 998, 739, 693 cm$^{-1}$; $^1$H NMR (300 MHz, C$_6$D$_6$) δ 2.45 (d, J=0.8 Hz, 3H, CH$_3$), 7.00-7.07 (m, 3H, Harom), 7.08-7.19 (m, 12H, Harom), 7.30-7.32 (m, 1H, Harom), 7.36-7.38 (m, 1H, Harom), 7.43-7.48 m, 6H, Harom); $^{13}$C NMR (75.5 MHz, C$_6$D$_6$) δ 21.2 (d, J=22.6 Hz, CH$_3$), 126.0 (Carom), 128.3 (Carom), 128.4 (m, Carom), 128.5 (Carom), 128.6 (d, J=7.3 Hz, Carom), 129.2 (d, J=6.2 Hz, Carom), 130.2 (d, J=4.5 Hz, Carom), 133.7 (Carom), 133.8 (Carom), 134.0 (Carom), 134.1 (Carom), 134.2 (d, J=18.7 Hz, Carom), 134.3 (Carom), 134.4 (Carom), 134.5 (Carom), 136.7 (dd, J=5.6, 13.3 Hz, Carom), 137.0 (dd, J=5.6, 13.3 Hz, Carom), 137.7 (dd, J=6.1, 12.8 Hz, Carom), 138.0 (dd, J=6.1, 12.8 Hz, Carom), 142.4 (d, J=26.2 Hz, Carom), 143.8 (dd, J=11.7, 32.9 Hz, Carom), 144.4 (dd, J=12.2, 33.2 Hz, Carom); $^{31}$P NMR (121 MHz, C$_6$D$_6$) δ −12.7 (d, J=154.0 Hz), −19.8 (d, J=154.0 Hz); HRMS calcd for $C_{31}H_{26}P_2Na$ [M+Na]$^+$ 483.1402. found 483.1423.

I.2.2. (S,S)-Bis[1,2-(o-anisyl-phenyl)phosphino]benzene 48j

To a solution of (S)-o-anisyl-(o-bromo)phenylphosphine (II-i) (0.22 g, 0.59 mmol) in THF (3 mL) was added at −78° C. under argon n-BuLi (1.6 M in hexane) (0.41 mL, 0.65 mmol) and the resulting solution was stirred at this temperature during one hour. At this time, a solution of (R)-phenyl-o-anisylphenylphosphinite (0.18 g, 0.59 mmol) in THF (2 mL) was added dropwise at −78° C. and the mixture was stirred at room temperature overnight. After quenching with water, the mixture was extracted with methylene chloride (3×5 mL) and the organic phases were dried over MgSO$_4$. The solvent was evaporated under vacuo to give a residue which was purified by chromatographic column on silica gel using methylene chloride/petroleum ether (2/1) as eluent and recristallisation in methylene chloride/methyl alcohol.

White solid; Yield: 52%; Enantiomeric excess: 99% by $^{31}$P NMR in the presence of (+)-di-µ-chlorobis{2-[1-(dimethylamino)ethyl]phenyl-C,N}dipalladium; $R_f$ 0.39 (methylene chloride/petroleum ether 2:1); [α]$_D$+116.2 (c 0.4, CHCl$_3$); IR (neat) 3055, 2937, 2832, 1571, 1469, 1429, 1295, 1270, 1239, 1178, 1157, 1130, 1093, 1069, 1039, 1023, 1012, 792, 745, 730, 690 cm$^{-1}$; $^1$H NMR (300 MHz, CDCl$_3$) δ 3.57 (s, 6H, OCH$_3$), 6.69-6.72 (m, 2H, Harom), 6.80-6.84 (m, 4H, Harom), 6.99-7.02 (m, 2H, Harom), 7.24-7.32 (m, 14H, Harom); $^{13}$C NMR (75.5 MHz, CDCl$_3$) δ 55.5 (OCH$_3$), 110.2 (Carom), 120.8 (Carom), 126.6 (t, J=3.6 Hz, Carom), 128.1 (3s, Carom), 128.9 (Carom), 129.8 (Carom), 133.5 (t, J=3.2 Hz, Carom), 133.9 (Carom), 134.0 (Carom), 134.1 (Carom), 134.2 (Carom), 136.9 (t, J=3.9 Hz, Carom), 143.3 (t, J=11.9 Hz, Carom), 161.0 (d, J=6.9 Hz, Carom); $^{31}$P NMR (121 MHz, CDCl$_3$) δ −23.4 (s); HRMS calcd for $C_{32}H_{38}O_2P_2Na$[M+Na]$^+$ 507.1637. found 507.1637.

I.2.3. (1R,2S)-(+)-1-(i-Propylphenylphosphino)-2-(o-anisylphenylphosphino)-benzene 48k To a solution of (R)-isopropyl-(2-bromophenyl)-phenylphosphine (II-m) (0.18 g, 0.59 mmol) in THF (3 mL) was added at −78° C. under argon n-BuLi (1.6 M in hexane) (0.41 mL, 0.65 mmol) and the resulting solution was stirred at this temperature during one hour. At this time, a solution of (R)-phenyl-o-anisylphenylphosphinite (0.18 g, 0.59 mmol) in THF (2 mL) was added dropwise at −78° C. and the mixture was stirred at room temperature overnight. After quenching with water, the mixture was extracted with methylene chloride (3×5 mL) and the organic phases were dried over MgSO$_4$. The solvent was evaporated under vacuo to give a residue which was purified by chromatographic column on silica gel using methylene chloride/petroleum ether (2/1) as eluent.

White sticky solid; Yield: 56%; Enantiomeric excess: 99% by HPLC analysis (Chiralpak AD, 0.2 mL·min$^{-1}$, hexane/2-propanol 98:2, $t_R$ (RS)=24.5 min, $t_R$ (SS)=27.5 min; $R_f$ 0.44 (petroleum ether/methylene chloride 1:2); [α]D+85.0 (c 0.2 CHCl$_3$); IR (neat) 2954, 1575, 1461, 1429, 1271, 1239, 1179, 1129, 1070, 1023, 745, 695 cm$^{-1}$; $^1$H NMR (300 MHz, CDCl$_3$) δ 6.81 (td, J=6.8, 15.4 Hz, 6H, CH$_3$), 2.47-2.57 (m, 1H, CH), 3.61 (s, 3H, OCH$_3$), 6.47 (ddd, J=1.5, 3.8, 7.2 Hz, 1H, Harom), 6.65 (t, J=7.4 Hz, 1H, Harom), 6.79 (ddd, J=0.7, 4.7, 8.2 Hz, 1H, Harom), 6.89-6.92 (m, 1H, Harom), 7.14-7.24 (m, 5H, Harom), 7.30-7.39 (m, 8H, Harom), 7.61-7.64 (m, 1H, Harom); $^{13}$C NMR (75.5 MHz, CDCl$_3$) δ 19.5 (CH$_3$), 19.7 (CH$_3$), 25.6 (dd, J=8.1, 10.7 Hz, CH), 55.6 (OCH$_3$), 110.1 (d, J=1.4 Hz, Carom), 120.7 (Carom), 126.0 (dd, J=5.2, 13.7 Hz, Carom), 127.8 (d, J=7.2 Hz, Carom), 128.0 (Carom), 128.2 (2s, Carom), 128.8 (d, J=17.2 Hz, Carom), 129.8 (Carom), 131.7 (d, J=6.4 Hz, Carom), 133.3 (d, J=19.2 Hz, Carom), 134.0 (Carom), 134.0 (d, J=7.2 Hz, Carom), 134.2 (Carom), 134.4 (Carom), 137.3 (dd, J=7.3, 13.8 Hz, Carom), 138.3 (d, J=2.9 Hz, Carom), 143.8 (dd, J=13.9, 31.6 Hz, Carom), 144.9 (d, J=10.1 Hz, Carom), 160.9 (d, J=13.5 Hz, Carom); $^{31}$P NMR (121 MHz, CDCl$_3$) δ −13.5 (d, J=163.2 Hz), −24.6 (d, J=163.2 Hz); HRMS calcd for $C_{28}H_{29}OP_2$[M+H]$^+$ 443.1688. found 443.1667.

J. Synthesis of Diphosphines with a Biphenyl Bridge (I-49)

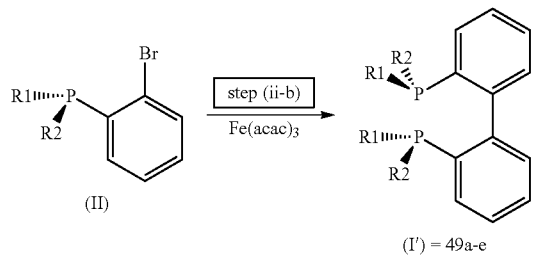

TABLE 8

Synthesis of diphosphines with a biphenyl bridge (I'-49)

| o-Bromophenylphosphine (II) | | | Diphosphine (I'-49) | Rdt (%) | e.e. (%) |
|---|---|---|---|---|---|
| | $R^1$ | $R^2$ | | | |
| (II-a) | Ph | Ph | 49a | 46 | — |
| (II-e) | o-Tol | o-Tol | 49b | 36 | — |
| (R)-(II-k) | Fc | Ph | (S,S)-49c | 35[a] | 99 |
| (R)-(II-n) | Ph | c-Hex | (R,R)-49d | 27 | — |
| (S)-(II-o) | Ph | o-Tol | (S,S)-49e | 45 | — |

[a]isolated as a diborane complex

J.1. bis-2,2'-(Diphenylphosphino)biphenyle 49a

To a solution of (2-bromophenyl)-diphenylphosphine (II-a) (0.41 g, 1.20 mmol) in THF (5 mL) was added at −78° C. under argon n-BuLi (1.6 M in hexane) (0.75 mL, 1.20 mmol) and the resulting solution was stirred at this temperature during one hour. A solution of Fe(acac)$_3$ (0.52 g, 1.44 mmol) in THF (7 mL) was then added and the stirring was maintained during one hour at −78° C. The solution was quenched with water (2 mL) and extracted with methylene chloride (3×10 mL). The organic phases were dried over MgSO$_4$ and the solvent evaporated under vacuo to give a residue which was purified by chromatographic column on silica gel using petroleum ether/methylene chloride (2/1) as eluent. The titled compound was obtained as white solid. Yield: 46%; Rf 0.32 (petroleum ether/CH$_2$Cl$_2$ 2/1); $^1$H NMR (300 MHz, CDCl$_3$) δ 6.80-6.84 (m, 2H, Harom), 6.98-7.01 (m, 2H, Harom), 7.04-7.22 (m, 24H, H arom); $^{31}$P NMR (121 MHz, CDCl$_3$) δ −14.4. Noteworthy, the coupling of (II-a) was also carried out with FeCl$_3$ or Cu(OAc)$_2$ and the diphosphine 49a was obtained in satisfactory yields (30-45%).

J.2. bis-2,2'-(di-o-tolylphosphino)biphenyle 49b

To a solution of (2-bromophenyl)-di(o-tolyl)phosphine (II-e) (0.44 g, 1.20 mmol) in THF (5 mL) was added at −78° C. under argon n-BuLi (1.6 M in hexane) (0.82 mL, 1.32 mmol) and the resulting solution was stirred at this temperature during one hour. A solution of Fe(acac)$_3$ (0.52 g, 1.44 mmol) in THF (7 mL) was then added and the stirring was maintained during one hour at −78° C. The solution was quenched with water (2 mL) and extracted with methylene chloride (3×10 mL). The organic phases were dried over MgSO$_4$ and the solvent evaporated under vacuo to give a residue which was purified by chromatographic column on silica gel using petroleum ether/toluene (20/1) as eluent. The titled compound was obtained as white solid. Yield: 36%; Rf 0.41 (petroleum ether/toluene 20/1); IR (neat) 3050, 3002, 1450, 1428, 1380, 1267, 1201, 1129, 1034, 951, 877, 801, 751, 717 cm$^{-1}$; $^1$H NMR (300 MHz, CDCl$_3$) δ 2.11 (s, 6H, CH$_3$), 2.44 (sl, 6H, CH$_3$), 6.77-6.78 (m, 2H, Harom), 6.92-6.93 (m, 2H, Harom), 6.97-7.01 (m, 4H, Harom), 7.06-7.09 (m, 2H, Harom), 7.12-7.15 (m, 4H, Harom), 7.19 (td, J=1.4, 7.5 Hz, 2H, Harom), 7.23-7.29 (m, 6H, Harom); $^{13}$C NMR (75.5 MHz, CDCl$_3$) δ 20.9 (d, J=24.1 Hz, CH$_3$), 21.5 (t, J=12.1 Hz, CH$_3$), 125.7 (d, J=6.6 Hz, Carom), 127.2 (Carom), 127.4 (Carom), 128.2 (Carom), 128.6 (Carom), 129.6 (t, J=3.0 Hz, Carom), 129.9 (t, J=2.0 Hz, Carom), 131.2 (dd, J=4.2, 3.7 Hz, Carom), 132.6 (Carom), 133.1 (Carom), 135.2 (Carom), 135.6 (d, J=14.4 Hz, Carom), 135.7 (Carom), 136.1 (d, J=24.1 Hz, Carom), 143.0 (d, J=25.7 Hz, Carom), 143.3 (d, J=28.3 Hz, Carom); $^{31}$P NMR (121 MHz, CDCl$_3$) δ −28.5. HRMS calcd for C$_{40}$H$_{36}$P$_2$Na (M+Na)$^+$ 601.2185. found 601.2164.

J.3. Synthesis of (S,S)-bis-2,2'-(ferrocenylphenylphosphino)biphenyl diborane and free diphosphine 49c To a solution of (S)-Ferrocenyl-(2-bromophenyl)-phenylphosphine (II-k) (0.20 g, 0.44 mmol) in THF (4 mL) was added at −78° C. under argon n-BuLi (1.6 M in hexane) (0.30 mL, 0.48 mmol) and the resulting solution was stirred at this temperature during one hour. A solution of Fe(acac)$_3$ (0.19 g, 0.53 mmol) in THF (5 mL) was then added and the stirring was maintained during one hour at −78° C. The solution was quenched with water (2 mL) and extracted with methylene chloride (3×10 mL). The organic phases were dried over MgSO$_4$ and the solvent evaporated under vacuo to give a residue which was purified by chromatographic column on silica gel using petroleum ether/ethyl acetate (20/1) as eluent. The orange powder obtained was dissolved in THF and BH$_3$.DMS was added. After stirring overnight, water was added (1 mL) and the solution was extracted with methylene chloride (3×5 mL). The organic phases were dried over MgSO$_4$ and the solvent evaporated to give an orange solid which was recristallised in a mixture of hexane and methylene chloride. The titled diborane compound was obtained as orange crystals. Yield: 35%; Enantiomeric excess: 99% by HPLC analysis (chiralcel OD-H, 0.5 mL·min$^{-1}$, hexane-2-propanol 98:2, t$_R$ (S,S)=27.2 min, t$_R$ (R,R)=30.9 min; R$_f$ 0.42 (petroleum ether/ethyl acetate 3:1); [α]$_D$ −58.3 (c 0.3, CHCl$_3$); IR (neat) 3053, 2435, 2371, 2338, 1459, 1435, 1171, 1106, 1057, 1026, 1001, 823, 742, 697 cm$^{-1}$; $^1$H NMR (300 MHz, CDCl$_3$) δ 3.89 (s, 10H, Cp), 4.16 (sl, 2H, Cp), 4.21 (sl, 2H, Cp), 4.32-4.34 (m, 4H, Cp), 6.67-6.68 (m, 2H, Harom), 6.97-7.14 (m, 6H, Harom), 7.52-7.57 (m, 6H, Harom), 7.91-7.97 (m, 4H, Harom); $^{13}$C NMR (75.5 MHz, CDCl$_3$) δ 69.7 (Cp), 69.8 (d, J=68.1 Hz, Cp), 70.9 (d, J=5.3 Hz, Cp), 71.0 (d, J=7.9 Hz, Cp), 72.7 (d, J=1.6 Hz, Cp), 75.0 (d, J=18.2 Hz, Cp), 127.2 (d, J=9.0 Hz, Carom), 128.3 (d, J=10.2 Hz, Carom), 129.2 (d, J=2.1 Hz, Carom), 130.3 (d, J=54.0 Hz, Carom), 131.0 (d, J=2.2 Hz, Carom), 132.2 (d, J=61.5 Hz, Carom), 132.6 (d, J=7.7 Hz, Carom), 133.5 (d, J=9.2 Hz, Carom), 134.0 (d, J=8.3 Hz, Carom), 143.6 (dd, J=3.2, 9.7 Hz, Carom); $^{31}$P NMR (121 MHz, CDCl$_3$) δ 17.2; HRMS calcd for C$_{44}$H$_{42}$P$_2$B$_2$Fe$_2$Na (M+Na)$^+$ 789.1539. found 789.1549; Anal calcd for C$_{44}$H$_{42}$P$_2$B$_2$Fe$_2$: C, 68.99; H, 5.53. found: C, 69.27; H, 5.43.

(S,S)-bis-2,2'-(Ferrocenylphenylphosphino)biphenyl 49c

A solution of the diphosphine diborane (0.06 g, 0.08 mmol) and DABCO (0.05 g, 0.48 mmol) in dry toluene (4 mL) was stirred at room temperature overnight. After evaporation of the solvent in vacuo, the residue was purified by chromatographic column on silica gel using petroleum ether/ethyl acetate (3/1) as eluent to give the titled compound as an orange solid. Yield: 90%; Enantiomeric excess: 99% by HPLC analysis (chiralcel OD-H, 0.3 mL·min$^{-1}$, hexane-2-propanol 98:2, t$_R$ (R,R)=19.6 min, t$_R$ (S,S)=22.3 min; R$_f$ 0.21 (petroleum ether/ethyl acetate 20:1); [α]$_D$ −129.3 (c 0.2, CHCl$_3$); IR (neat) 3069, 2925, 1477, 1454, 1431, 1411, 1306, 1260, 1192, 1158, 1107, 1019, 1000, 815, 747, 699 cm; $^1$H NMR (300 MHz, CDCl$_3$) δ 3.82 (sl, 2H, Cp), 4.20 (s, 10H, Cp), 4.43-4.44 (m, 2H, Cp), 4.55 (sl, 2H, Cp), 4.82-4.83 (m, 2H, Cp), 6.53-6.54 (m, 2H, Harom), 7.05 (td, J=1.3, 7.4 Hz, 2H, Harom), 7.20-7.22 (m, 2H, Harom), 7.27 (td, J=1.2, 7.4 Hz, 2H, Harom), 7.28-7.34 (m, 10H, Harom); $^{13}$C NMR (75.5 MHz, CDCl$_3$) δ 69.2 (Cp), 69.8 (Cp), 71.0 (t, J=3.5 Hz, Cp), 71.5 (Cp), 74.5 (t, J=17.1 Hz, Cp), 127.1 (Carom), 127.5 (Carom), 127.7 (t, J=3.7 Hz, Carom), 128.3 (Carom), 130.2 (t, J=3.8 Hz, Carom), 132.4 (Carom), 134.4

(t, J=10.7 Hz, Carom), 137.9 (dd, J=4.0, 4.7 Hz, Carom), 138.9 (t, J=4.7 Hz, Carom), 145.6 (t, J=17.1 Hz, Carom); $^{31}$P NMR (121 MHz, CDCl3) δ −23.6; HRMS calcd for $C_{44}H_{36}P_2Fe_2Na$ (M+Na)$^+$761.0883. found 761.0846; Anal calcd for $C_{44}H_{36}P_2Fe_2$: C, 71.57; H, 4.91. found: C, 71.12; H, 5.06.

J.4. (R,R)-bis-2,2'-(cyclohexylphenylphosphino)biphenyl 49d

The same procedure as described for 49a was used starting from (R)-(2-bromophenyl)-cyclohexyl-phenylphosphine (II-o). The product was purified by column chromatography on silica gel with a mixture hexane/CH$_2$Cl$_2$ as eluent.

$^{31}$P NMR (CDCl$_3$): δ=−17.1

J.5. (S,S)-bis-2,2'-(phenyl-o-tolylphosphino)biphenyl 49e

The same procedure as described for 49a was used starting from (S)-(2-bromophenyl)-phenyl-(o-tolyl)phosphine (II-o). The product was purified by column chromatography on silica gel with a mixture Hexane/EtOAc 50:1 as eluent.

$^{31}$P NMR (CDCl$_3$): δ=−18.7 and −23.0

K. Catalysis of Asymmetric Hydrogenation by Chiral Rhodium Complexes

Chiral diphosphines (1-48) and (I'-49c) were tested in catalyzed asymmetric hydrogenation reactions as rhodium complexes. Substrates used are methyl α-aceamidocinnamate 63, dimethyl itaconate 65, precursor 67 of Levetiracetam 69 and dehydroesters 70 and 72:

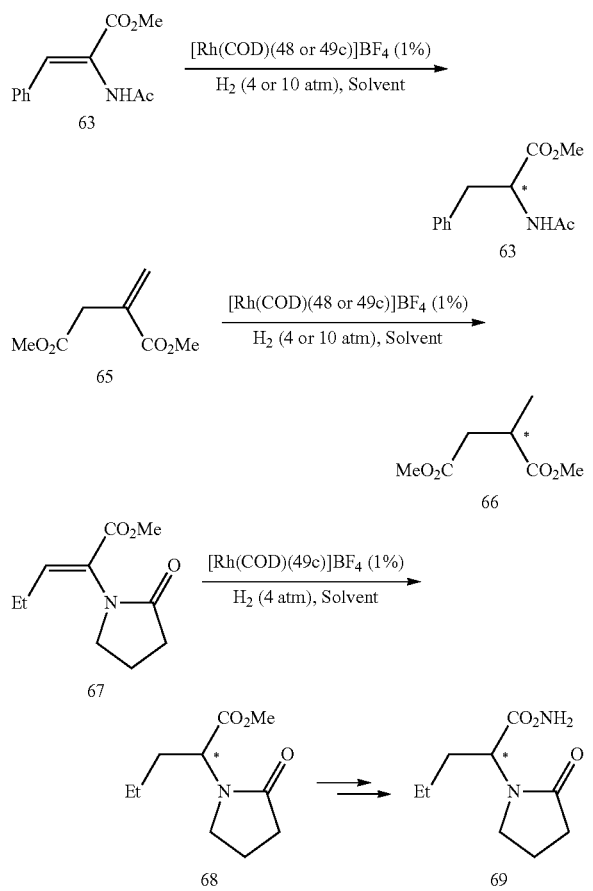

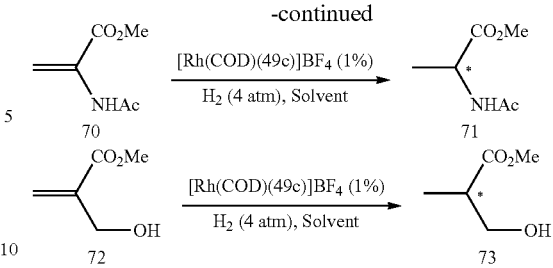

K.1. Preparation of rhodium complexes with 1,2-diphosphino benzene ligands (I-48)

General procedure

To a solution of [Rh(COD)$_2$]BF$_4$ (0.09 mmol) in methylene chloride (2.5 mL) was added dropwise under argon a solution of diphosphine (0.1 mmol) in methylene chloride (3.5 mL). The resulting solution was stirred at this temperature during one hour and then diethyl ether (10 mL) was added. The precipitate was filtered and washed with diethyl ether (3×5 mL) to afford the rhodium complexes.

(Cycloocta-1,5-diene)-(Sp)-[1-diphenylphosphino-2-(o-anisyl-phenylphosphino)-benzene 48a]rhodium tetrafuoroborate General procedure; Orange solid; Yield 80%; $^1$H NMR (300 MHz, CDCl$_3$) δ 2.35-2.45 (m, 8H, CH$_2$), 3.66 (s, 3H, OCH$_3$), 4.83-5.21 (m, 4H, CH), 6.99-7.00 (m, 2H, Harom), 7.12-7.14 (m, 1H, Harom), 7.45-7.60 (m, 20H, Harom); $^{31}$P NMR (121 MHz, CDCl$_3$) δ 49.9 (dd, J=27.6, 150.7 Hz), 57.0 (dd, J=27.6, 150.7 Hz); HRMS calcd for $C_{39}H_{38}OP_2Rh$ [M-BF$_4$]$^+$ 687.1447. found 687.1436.

(Cycloocta-1,5-diene)-(Sp)-[1-dicyclohexylphosphino-2-(o-anisyl-phenylphosphino)-benzene 48b] rhodium tetrafitoroborate General procedure; Orange solid; Yield 63%; $^1$H NMR (300 MHz, CDCl$_3$) δ 0.85-1.40 (m, 12, Hcy), 1.66-1.76 (m, 6H, Hcy), 1.93-1.97 (m, 1H, Hcy), 2.17-2.51 (m, 11H, Hcy/CH$_2$), 3.55 (s, 3H, OCH$_3$), 4.66-4.73 (m, 2H, CH), 5.57 (sl, 1H, CH), 5.92 (sl, 1H, CH), 6.93-7.02 (m, 3H, Harom), 7.36-7.62 (m, 9H, Harom), 7.71-7.75 (m, 1H, Harom); $^{31}$P NMR (121 MHz, CDCl$_3$) δ 53.2 (dd, J=24.9, 150.6 Hz), 62.5 (dd, J=24.9, 145.4 Hz); HRMS calcd for $C_{39}H_{50}OP_2Rh$ [M-BF$_4$]$^+$ 699.2386. found 699.2362.

(Cycloocta-1,5-diene)-(Sp)-[1-diisopropylphosphino-2-(o-anisyl-phenylphosphino)-benzene 48c] rhodium tetrafuoroborate General procedure; Orange solid; Yield 53%; 1H NMR (300 MHz, CDCl$_3$) δ 0.89 (dd, J=7.0, 16.3 Hz, 3H, CH$_3$), 1.18 (dd, J=7.2, 16.4 Hz, 3H, CH$_3$), 1.25-1.29 (m, 6H, CH$_3$), 2.29-2.46 (m, 6H, CH$_2$/CH), 2.53-2.60 (m, 2H, CH$_2$), 2.66-2.82 (m, 2H, CH$_2$), 3.60 (s, 3H, OCH$_3$), 4.75-4.79 (2sl, 2H, CH$_{COD}$), 5.67 (sl, 1H, CH$_{COD}$), 6.05 (sl, 1H, CH$_{COD}$), 6.98-7.07 (m, 3H, Harom), 7.41-7.47 (m, 3H, Harom), 7.51-7.69 (m, 3H, Harom), 7.64-7.67 (m, 3H, Harom), 7.78-7.80 (m, 1H, Harom); $^{31}$P NMR (121 MHz, CDCl$_3$) δ 52.5 (dd, J=23.9, 152.3 Hz), 69.5 (dd, J=23.9, 146.3 Hz); HRMS calcd for $C_{33}H_{42}OP_2Rh$ [M-BF$_4$]+ 619.1760. found 619.1758.

(Cycloocta-1,5-diene)-(Sp)-[1-di(p-tolyl)phosphino-2-(o-anisyl-phenylphosphino)-benzene 48e]rhodium tetrafuoroborate General procedure; Orange solid; Yield 54%; $^1$H NMR (300 MHz, CDCl$_3$) δ 2.31-2.43 (m, 8H, CH$_2$), 2.42 (s, 3H, CH$_3$), 2.44 (s, 3H, CH$_3$), 3.66 (s, 3H, OCH$_3$), 4.83-5.21 (m, 4H, CH), 6.97-7.02 (m, 2H, Harom), 7.12-7.15 (m, 1H, Harom), 7.25-7.26 (m, 2H, Harom), 7.31-7.35 (m, 4H, Harom), 7.42-7.54 (m, 5H, Harom), 7.55-7.61 (m, 7H, Harom); $^{31}$P NMR (121 MHz, CDCl$_3$) δ 49.8 (dd, J=26.7, 148.2 Hz), 56.2 (dd, J=26.7, 150.7 Hz); HRMS calcd for C$_{41}$H$_{42}$OP$_2$Rh [M-BF$_4$]$^+$ 715.1760. found 715.1733.

(Cycloocta-1,5-diene)-(Sp)-[1-di(p-trifluoromethyl-phenyl)phosphino-2-(o-anisyl-phenylphosphino)-benzene 48f]rhodium tetrafuoroborate General procedure; Yellow solid, Yield 66%; $^1$H NMR (300 MHz, CDCl$_3$) δ 2.38-2.50 (m, 8H, CH$_2$), 3.70 (s, 3H, OCH$_3$), 4.90-5.31 (m, 4H, CH), 6.96-6.98 (m, 2H, Harom), 7.12 (dd, J=5.1, 8.4 Hz, 1H, Harom), 7.47-7.63 (m, 12H, Harom), 7.69-7.72 (m, 4H, Harom), 7.81-7.82 (m, 2H, Harom); $^{31}$P NMR (121 MHz, CDCl$_3$) δ 49.7 (dd, J=29.2, 148.2 Hz), 56.0 (dd, J=29.2, 153.0 Hz); HRMS calcd for C$_{41}$H$_{36}$OF$_6$P$_2$Rh [M-BF$_4$]$^+$ 823.1195. found 823.1192.

(Cycloocta-1,5-diene)-(Rp)-[1-diphenylphosphino-2-(ferrocenyl-phenylphosphino)-benzene 48 g]rhodium tetrafuoroborate General procedure; Dark orange solid; Yield 73%; $^1$H NMR (300 MHz, CDCl$_3$) δ 1.91-2.00 (m, 2H, CH$_2$), 2.23-2.25 (m, 2H, CH$_2$), 2.51-2.64 (m, 4H, CH$_2$), 3.61 (s, 5H, Cp), 4.42 (sl, 1H, Cp), 4.51 (sl, 1H, Cp), 4.62-4.65 (m, 4H, Cp/CH), 5.22-5.23 (m, 1H, CH), 5.61-5.62 (m, 1H, CH), 7.35-7.42 (m, 4H, Harom), 7.45-7.47 (m, 3H, Harom), 7.52-7.55 (m, 3H, Harom), 7.61-7.69 (m, 6H, Harom), 7.74-7.76 (m, 1H, Harom), 7.90-7.93 (m, 2H, Harom); $^{31}$P NMR (121 MHz, CDCl$_3$) δ 51.0 (dd, J=29.1, 148.2 Hz), 58.2 (dd, J=29.1, 153.0 Hz); HRMS calcd for C$_{42}$H$_{40}$FeP$_2$Rh [M-BF$_4$]$^+$ 765.1005. found 765.0987.

(Cyclocta-1,5-diene)-(Rp)-[1-diphenylphosphino-2-(isopropyl-phenylsphino)-benzene 48h]rhodium tetrafuoroborate General procedure; Orange solid; Yield 60%; $^1$H NMR (300 MHz, CDCl$_3$) δ 1.22 (dd, J=7.0, 14.7 Hz, 3H, CH$_3$), 1.28 (dd, J=7.0, 19.5 Hz, 3H, CH$_3$), 2.13-2.16 (m, 2H, CH$_2$), 2.32-2.58 (m, 6H, CH$_2$), 3.29-3.33 (m, 1H, CH), 4.84-4.85 (m, 1H, CH), 4.92-4.93 (m, 1H, CH), 5.04-5.05 (m, 1H, CH), 5.69-5.70 (m, 1H, CH), 7.49-7.71 (m, 19H, Harom); $^{31}$P NMR (121 MHz, CDCl$_3$) δ 57.8 (dd, J=28.5, 154.9 Hz), 67.8 (dd, J=28.5, 148.6 Hz); HRMS calcd for C$_{35}$H$_{38}$P$_2$Rh [M-BF$_4$]$^+$ 623.1498. found 623.1500.

(Cycloocta-1,5-diene)-(1S,2S)-[1,2-(o-anisyl-phenylphosphino)-benzene 48j]rhodium tetrafuioroborate To a suspension of [Rh(COD)$_2$]BF$_4$ (0.055 mmol) in THF (1.2 mL) was added dropwise under argon a solution of diphosphine 48j (0.059 mmol) in THF (1.7 mL). The resulting solution was stirred at this temperature during one hour and the solvent was evaporated to about 1 mL. Diethyl ether (5 mL) was added and the resulting precipitate was filtered then washed with diethyl ether (3×5 mL) to afford the corresponding rhodium complex.

Orange solid; Yield 64%; $^1$H NMR (300 MHz, CDCl$_3$) δ 2.33-2.51 (m, 8H, CH$_2$), 3.60 (s, 6H, OCH$_3$), 5.07 (sl, 4H, CH), 6.89-6.93 (m, 4H, Harom), 7.09-7.11 (m, 2H, Harom), 7.42-7.58 (m, 12H, Harom), 7.67-7.70 (m, 4H, Harom); $^{31}$P NMR (121 MHz, CDCl$_3$) δ 50.7 (d, J=149.8 Hz); HRMS calcd for C$_{40}$H$_{40}$O$_2$P$_2$Rh [M-BF$_4$]$^+$ 717.1553. found 717.1522.

(Cycloocta-1,5-diene)-(1S,2R)-[2-(isopropyl-phenylphosphino)-1-(o-anisyl-phenyl phosphino)-benzene 48k]rhodium tetrafuoroborate To a suspension of [Rh(COD)$_2$]BF$_4$ (0.055 mmol) in THF (1.2 mL) was added dropwise under argon a solution of diphosphine 48k (0.059 mmol) in THF (1.7 mL). The resulting solution was stirred at this temperature during one hour and the solvent was evaporated to about 1 mL. Diethyl ether (5 mL) was added and the resulting precipitate was filtered then washed with diethyl ether (3×5 mL) to afford the corresponding rhodium complex.

Orange solid; Yield 70%; $^1$H NMR (300 MHz, CDCl$_3$) δ 1.07 (dd, J=6.8, 15.0 Hz, 3H, CH$_3$), 1.17 (dd, J=6.8, 19.1 Hz, 3H, CH$_3$), 2.05-2.17 (m, 2H, CH$_2$), 2.28-2.30 (m, 2H, CH$_2$), 2.45-2.47 (m, 2H, CH$_2$), 2.56-2.58 (m, 2H, CH$_2$), 3.10-3.14 (m, 1H, CH), 3.60 (s, 3H, OCH$_3$), 4.70 (sl, 2H, CH), 5.00 (sl, 1H, CH), 5.70 (sl, 1H, CH), 7.04-7.13 (m, 3H, Harom), 7.52-7.61 (m, 13H, Harom), 7.76-7.79 (m, 2H, Harom); $^{31}$P NMR (121 MHz, CDCl$_3$) δ 50.4 (dd, J=26.9, 150.1 Hz), 64.0 (dd, J=26.9, 146.3 Hz); HRMS calcd for C$_{36}$H$_{40}$OP$_2$Rh [M-BF$_4$]$^+$ 653.1604. found 653.1591.

K.2. Preparation of rhodium complexes with diphosphine ligand (I'-49c)

(Cycloocta-1,5-diene)-[(S,S)-2,2'-bis(ferrocenyl-phenylphosphino)-1,1'-biphenyl 49c]rhodium tetrafuoroborate To a solution of [Rh(COD)$_2$]BF$_4$ (0.036 g, 0.09 mmol) in methylene chloride (2.5 mL) was added dropwise under argon a solution of diphosphine 49c (0.074 g, 0.1 mmol) in methylene chloride (3.5 mL). The resulting solution was stirred at this temperature during one hour and then diethyl ether (10 mL) was added. The precipitate was filtered and washed with diethyl ether (3×5 mL) to afford the rhodium complex 5 as an orange powder.

Yield 65%; $^1$H NMR (300 MHz, CDCl$_3$) δ 2.00-2.02 (m, 2H, CH$_2$), 2.17-2.22 (m, 2H, CH$_2$), 2.47-2.51 (m, 2H, CH$_2$), 2.59-2.64 (m, 2H, CH$_2$), 3.08 (sl, 2H, Hfer), 4.09 (sl, 10H, Hfer), 4.30 (br.s, 2H, Hfer), 4.64-4.72 (m, 8H, Hfer/CH), 6.63 (d, J=7.1 Hz, 2H, Harom), 7.11 (t, J=7.5 Hz, 2H, Harom), 7.25-7.27 (m, 10H, Harom), 7.37 (t, J=7.3 Hz, Harom), 8.18 (br.s, 2H, Harom); $^{31}$P NMR (121 MHz, CDCl$_3$) δ 21.0 (d, J=145.6 Hz); HRMS calcd for C$_{52}$H$_{48}$Fe$_2$P$_2$Rh [M-BF$_4$]$^+$ 949.0982. found 949.0999.

K.3. Asymmetric Catalyzed Hydrogenation

Typical procedure

A solution of [Rh(COD)L*]BF$_4$ (0.005 mmol, 1 mol %) and substrate (0.5 mmol) in dry solvent (7.5 mL) was introduced in a stainless steel autoclave. The autoclave was closed, purged with hydrogen and then pressurized with hydrogen. After 16 h of stirring at room temperature, the pressure was released to atmospheric pressure and the solution was transferred to a round bottom flask. The solvent was removed on a rotary evaporator to give a residue which was purified by column chromatography on silica gel to afford the hydrogenated product. The enantiomeric excess was determined by HPLC on chiral column.

Results of aymmetric catalyzed hydrogenations by rhodium complexes of ligands (I-48) or (I-49) are presented in table 9 and 10.

TABLE 9

Asymmetric catalyzed hydrogenation by rhodium complexes of ligands (I-48)

| Substrate | Diphosphine 48 | | | | Cond. (RT°/16 h) | | Product | |
|---|---|---|---|---|---|---|---|---|
| | | R¹ | R² | R⁷ | R⁸ | Solvent | P (H₂) | Conv (%) | ee (%) |

| Substrate | | R¹ | R² | R⁷ | R⁸ | Solvent | P(H₂) | Conv (%) | ee (%) |
|---|---|---|---|---|---|---|---|---|---|
| 63 | 48a | Ph | o-An | Ph | Ph | MeOH | 4 | 64 | 93 | 61 (R) |
| " | " | " | " | " | " | " | 10 | " | 100 | 63 (R) |
| " | " | " | " | " | " | " | 20 | " | 100 | 60 (R) |
| " | " | " | " | " | " | THF | 10 | " | 6 | nd |
| " | " | " | " | " | " | CH₂Cl₂ | " | " | 7 | nd |
| " | " | " | " | " | " | EtOH | " | " | 100 | 55 (R) |
| " | " | " | " | " | " | i-PrOH | " | " | 81 | 38 (R) |
| " | " | " | " | " | " | Toluene | " | " | 2 | nd |
| " | 48b | " | o-An | cHex | cHex | MeOH | 10 | " | 100 | 32 (R) |
| " | " | " | " | " | " | THF | " | " | 100 | 20 (R) |
| " | " | " | " | " | " | CH₂Cl₂ | " | " | 23 | nd |
| " | 48c | " | o-An | i-Pr | i-Pr | MeOH | " | " | 100 | 42 (R) |
| " | 48e | " | o-An | p-Tol | p-Tol | MeOH | 10 | " | 100 | 49 (R) |
| " | 48f | " | o-An | p-CF₃Ph | p-CF₃Ph | MeOH | 10 | " | 100 | 45 (R) |
| " | 48g | " | Fc | Ph | Ph | MeOH | 10 | " | 100 | 6 (R) |
| " | 48h | " | i-Pr | Ph | Ph | MeOH | 10 | " | 100 | 58 (S) |
| " | 48i | " | Ph | o-Tol | Ph | MeOH | 10 | " | 100 | 54 (R) |
| " | 48j | " | o-An | o-An | Ph | MeOH | 10 | " | 100 | 19 (R) |
| " | 48k | " | i-Pr | o-An | Ph | MeOH | 10 | " | 100 | 22 (S) |
| 65 | 48a | " | o-An | Ph | Ph | MeOH | 10 | 66 | 100 | 32 (R) |
| " | " | " | " | " | " | THF | " | " | 100 | 0 |
| " | " | " | " | " | " | CH₂Cl₂ | " | " | 100 | 2 (R) |
| " | 48b | " | o-An | cHex | cHex | MeOH | 10 | " | 100 | 45 (R) |
| " | " | " | " | " | " | THF | " | " | 100 | 57 (R) |
| " | " | " | " | " | " | CH₂Cl₂ | " | " | 100 | 57 (R) |
| " | 48c | " | o-An | i-Pr | i-Pr | MeOH | " | " | 100 | 12 (R) |
| " | " | " | " | " | " | CH₂Cl₂ | " | " | 100 | 48 (R) |
| " | 48e | " | o-An | p-Tol | p-Tol | MeOH | | " | 100 | 0 |
| " | " | " | " | " | " | CH₂Cl₂ | " | " | 100 | 2 (R) |
| " | 48f | " | o-An | p-CF₃Ph | p-CF₃Ph | MeOH | 10 | " | 100 | 3 (R) |
| " | " | " | " | " | " | CH₂Cl₂ | " | " | 100 | 0 |
| " | 48g | " | Fc | Ph | Ph | CH₂Cl₂ | 10 | " | 100 | 56 (R) |
| " | 48h | " | i-Pr | Ph | Ph | CH₂Cl₂ | 10 | " | 100 | 44 (R) |
| " | 48i | " | Ph | o-Tol | Ph | CH₂Cl₂ | 10 | " | 100 | 0 |
| " | 48j | " | o-An | o-An | Ph | CH₂Cl₂ | 10 | " | 100 | 46 (R) |
| " | 48k | " | i-Pr | o-An | Ph | MeOH | 10 | " | 100 | 57 (R) |
| " | 48k | " | i-Pr | o-An | Ph | CH₂Cl₂ | 10 | " | 100 | 76 (R) |

TABLE 10

Asymmetric catalyzed hydrogenation by rhodium complex of ligand (I'-49c)

| Substrate | Conditions (RT ° C./16 h) | | | Product | |
|---|---|---|---|---|---|
| | Solvent | P(H₂) | | Conv (%) | ee (%) |
| Ph−C(CO₂Me)=C(NHAc) 63 | MeOH | 4 | 64 | 100 | 85 (R) |
| | " | 10 | " | 100 | 80 (R) |
| | THF | 4 | " | 100 | 68 (R) |
| | CH₂Cl₂ | " | " | 100 | 70 (R) |
| | PC | " | " | 100 | 66 (R) |
| | toluene | " | " | 100 | 46 (R) |
| MeO₂C−CH₂−C(=CH₂)−CO₂Me 65 | MeOH | 4 | 66 | 100 | 32 (S) |
| | THF | " | " | 100 | 72 (S) |
| | CH₂Cl₂ | " | " | 100 | 96 (S) |

TABLE 10-continued

Asymmetric catalyzed hydrogenation by rhodium complex of ligand (I'-49c)

| Substrate | Conditions (RT ° C./16 h) | | Product | |
|---|---|---|---|---|
| | Solvent | P(H₂) | Conv (%) | ee (%) |
| 67 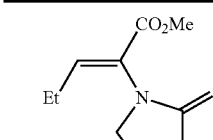 | MeOH<br>THF<br>CH₂Cl₂ | 4<br>"<br>" | 68<br>"<br>" | 100<br>100<br>100 | 38 (R)<br>43 (R)<br>38 (R) |
| 70 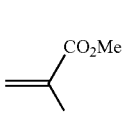 | MeOH<br>THF<br>CH₂Cl₂ | 4<br>"<br>" | 71<br>"<br>" | 100<br>100<br>100 | 90 (R)<br>16 (R)<br>40 (R) |
| 72 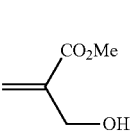 | MeOH<br>THF<br>CH₂Cl₂<br>toluene | 4<br>"<br>"<br>" | 73<br>"<br>"<br>" | 100<br>100<br>100<br>100 | 36 (S)<br>43 (S)<br>58 (S)<br>6 (S) |

Methyl 2-acetamido-3-phenylpropionate 64

The enantiomeric excess of 64 was determined by HPLC on Chiralcel OD-H hexane/2-propanol 95:5, 1 mL·min⁻¹, $t_R$ (R) 21.4 min, $t_R$ (S) 34.7 min. H NMR (300 MHz, CDCl₃) δ 1.97 (s, 3H, CH₃), 3.06-3.08 (m, 2H, CH₂Ph), 3.64 (s, 3H, CH₃), 4.86-4.88 (m, 1H, CH), 6.11 (br s, 1H, NH), 7.19-7.22 (m, 5H, Harom).

Dimethyl 3-methylsuccinate 66

The enantiomeric excess of 66 was determined by HPLC on Chiralcel OD-H hexane/2-propanol 95:5, 0.5 mL·min⁻¹, $t_R$ (R) 13.0 min, $t_R$ (S) 21.8 min. ¹H NMR (300 MHz, CDCl₃) δ 1.14 (d, J=7.1 Hz, 3H, CH₃), 2.31 (dd, J=3.0, 16.5 Hz, 1H, CH₂), 2.66 (dd, J=8.1, 16.5 Hz, 1H, CH₂), 2.84-2.86 (m, 1H, CH), 3.60 (s, 3H, CH₃), 3.62 (s, 3H, CH₃).

L. Catalysis of Asymmetric Allylation by Chiral Palladium Complexes

Chiral diphosphines (I-48) were tested in catalyzed asymmetric allylation reactions of dimethyl malonate 74 in its derivative 76, in presence of chiral palladium complexes. Reactions were carried out at ambiant temperature and results obtained after 18 h of reaction are presented in Table 11.

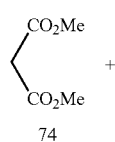

74

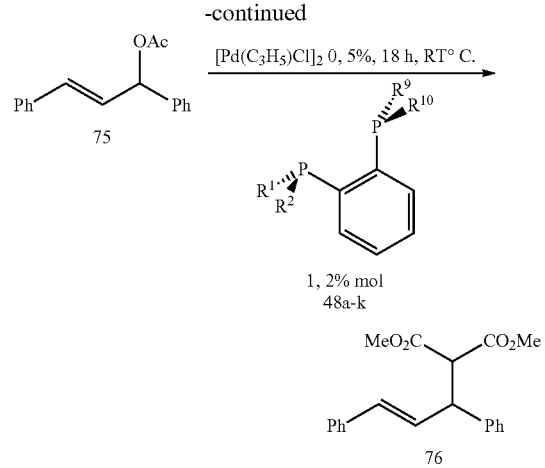

TABLE 11

Asymmetric catalyzed allylation by palladium complexes and diphosphine (I-48).

| Diphosphine 48 (R¹ = Ph) | | | | | Conditions (RT ° C./18 h)⁽ᵃ⁾ | | Product 76 | | |
|---|---|---|---|---|---|---|---|---|---|
| | R² | R⁹ | R¹⁰ | Base⁽ᵇ⁾ | Solvent | Conv (%) | Rdt (%) | e.e. (%) |
| 48a | o-An | Ph | Ph | A | THF | 100 | 80 | 21 (S) |
| " | " | " | " | B | " | 100 | 86 | 19 (S) |
| " | " | " | " | " | CH₂Cl₂ | 100 | 83 | 24 (S) |
| " | " | " | " | " | Toluene | 100 | nd | 14 (S) |

TABLE 11-continued

Asymmetric catalyzed allylation by palladium complexes and diphosphine (I-48).

| | | | | | Conditions (RT ° C./18 h)[a] | | Product 76 | |
|---|---|---|---|---|---|---|---|---|
| Diphosphine 48 (R¹ = Ph) | | | | | | Conv | Rdt | e.e. |
| R² | R⁹ | R¹⁰ | Base[b] | Solvent | (%) | (%) | (%) | |
| 48b " | cHex | cHex | A | THF | 100 | nd | 13 (S) | |
| " " | " | " | B | " | 100 | 85 | 13 (S) | |
| " " | " | " | " | CH₂Cl₂ | 100 | nd | 45 (S) | |
| 48c " | i-Pr | i-Pr | A | THF | 100 | nd | 49 (S) | |
| " " | " | " | B | CH₂Cl₂ | 100 | nd | 56 (S) | |
| 48d " | o-Tol | o-Tol | A | THF | 100 | 84 | 58 (R) | |
| " " | " | " | B | CH₂Cl₂ | n.d. | 72ᵃ | 52 (R) | |
| 48e " | p-Tol | p-Tol | A | THF | 100 | nd | 6 (R) | |
| " " | " | " | B | CH₂Cl₂ | 100 | nd | 30 (S) | |
| 48f " | p-CF₃Ar | p-CF₃Ar | A | THF | 100 | nd | 6 (S) | |
| " " | " | " | B | CH₂Cl₂ | 100 | n.d | 14 (S) | |
| 48j | o-An | o-An | Ph | B | CH₂Cl₂ | 100ᵃ | n.d. | 53 (S) |
| 48k | i-Pr | o-An | Ph | B | CH₂Cl₂ | 100 | n.d. | 15 (S) |

[a] 1% [Pd(C₃H₅)Cl]₂.
[b] conditions A: NaH and B: BSA/KOAc

Typical Procedure for the Allylic Alkylation of 1,3-Diphenylpropenyl Acetate 75 with Dimethylmalonate 74

In a Schlenk tube, ligand (12 μmol, 1.2 mol %) and [Pd(η³-C₃H₅)Cl]₂ (5 μmol, 0.5 mol %) were dissolved in dichloromethane (2 mL) under argon atmosphere. The reaction mixture was stirred 1 h at room temperature and (E)-1,3-diphenylprop-2-en-1-yl acetate 75 (0.25 g, 1 mmol) in dichloromethane (1 mL) was transferred to this Schlenk tube. After 20 minutes, this solution was transferred into another reaction vessel containing N,O-bis(trimethylsilyl)acetamide (0.49 mL, 2 mmol), a catalytic amount of KOAc and dimethyl malonate 74 (0.23 mL, 2 mmol) in CH₂Cl₂ (4 mL). The reaction mixture was stirred at room temperature during 18 h. The reaction mixture was then diluted with diethyl ether and the organic layer was washed with a saturated aqueous NH₄Cl solution (2×5 mL) and then dried over MgSO₄. Evaporation under reduced pressure gave a residue which was purified by chromatography on silica gel with petroleum ether/ethyl acetate (10/1) as eluent affording the alkylated product.

Methyl 2-carboxymethoxy-3,5-diphenylpent-4-enoate 76

The enantiomeric excess of 76 was determined by HPLC on Chiralpak AD hexane/2-propanol 90:10, 0.5 mL·min⁻¹, $t_R$ (R) 15.8 min, $t_R$ (S) 22.7 min. H NMR (CDCl₃) S (ppm), 3.56 (s, 3H, CH₃), 3.75 (s, 3H, CH₃), 4.02 (d, J=10.9 Hz, 1H, CH), 4.27 (dd, J=8.8, J=10.8 Hz, 1H, CH), 6.40 (dd, J=8.6, 15.7 Hz, 1H, CH=), 6.54 (d, J=15.7 Hz, 1H, CH=), 7.10-7.40 (10H, m, Harom).

The invention claimed is:

1. A process for producing a compound of formula (I)

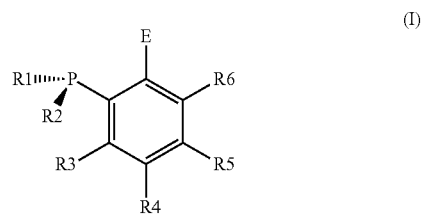

(I)

wherein

R1 and R2 may be the same or different and represent each a substituted or unsubstituted group selected from alkyl, cycloalkyl, aryl, alkyloxy, cycloalkyloxy, aryloxy, alkylamino, cycloalkylamino, arylamino, and metallocenyl;

R3, R4, R5, R6 may be the same or different and represent each a hydrogen atom or a substituted or unsubstituted group selected from the group consisting of alkyloxy, cycloalkyloxy, aryloxy, alkylamino, cycloalkylamino, and arylamino;

E represents a substituted or unsubstituted group —BR9R10;

wherein

R9 and R10 may be the same or different and represent each an halogen, an hydroxyl, a substituted or unsubstituted group selected from the group consisting of alkyloxy, aryloxy, cycloalkyloxy, alkyl cycloalkyl and aryl;

comprising (i) reacting chlorophosphine borane (VII)

(VII)

wherein R1 and R2 are as defined above, with a reagent RM, in which M is Li and R is an alkyl or an aryl group; and further reacting the product of this halogen-metal exchange with an aromatic compound of formula (VI)

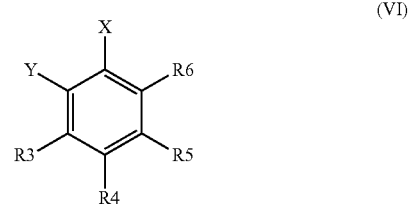

(VI)

wherein X and Y may be the same or different and each represent F, Cl, Br, or I, and R3, R4, R5 and R6 are as defined above, resulting in the corresponding P-chirogenic phosphine borane of formula (IV)

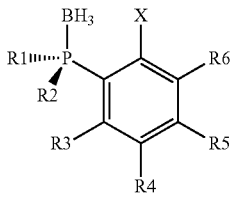
(IV)

wherein X, R1, R2, R3, R4, R5 and R6 are as defined above;

wherein step (i) is carried out under cooling condition, at a temperature ranging from −110° C. to −10° C.; and (ii) performing two chemical transformations on compound (IV) leading to compound (I): a step (ii-a) of removing of the borane group and a step (ii-b) of coupling of an electrophilic reagent, which is a boronate reagent, on the ortho position; steps (ii-a) and (ii-b) being carried out in any order.

2. The process according to claim 1, wherein compound (VII) is chiral.

3. The process according to claim 1, wherein compound (IV) first reacts under conditions of step (ii-a) leading to intermediate compound of formula (II),

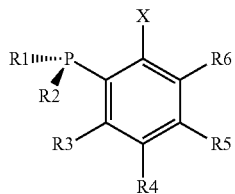
(II)

wherein R1, R2, R3, R4, R5, R6 and X are as previously defined.

4. The process according to claim 1, wherein compound (IV) first reacts under conditions of step (ii-b) leading to intermediate compound of formula (III),

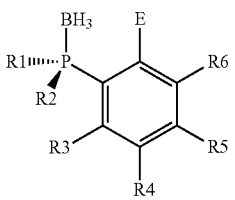
(III)

wherein R1, R2, R3, R4, R5, R6 and E are as previously defined.

* * * * *